United States Patent
Benson et al.

(10) Patent No.: US 8,008,505 B2
(45) Date of Patent: Aug. 30, 2011

(54) INDAZOLE OR 4,5,6,7-TETRAHYDRO-INDAZOLE DERIVATIVES

(75) Inventors: Gregory Martin Benson, Therwil (CH); Konrad Bleicher, Freiburg (DE); Uwe Grether, Efringen-Kirchen (DE); Bernd Kuhn, Reinach BL (CH); Hans Richter, Grenzach-Wyhlen (DE); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/563,193

(22) Filed: Sep. 21, 2009

(65) Prior Publication Data
US 2010/0076027 A1    Mar. 25, 2010

(30) Foreign Application Priority Data
Sep. 25, 2008   (EP) .................... 08165145

(51) Int. Cl.
| C07D 487/00 | (2006.01) |
| C07D 403/06 | (2006.01) |
| C07D 401/06 | (2006.01) |
| A61K 31/415 | (2006.01) |
| A61K 31/44  | (2006.01) |

(52) U.S. Cl. ............... 548/360.1; 548/250; 546/275.7; 514/406; 514/381; 514/338

(58) Field of Classification Search .............. None
See application file for complete search history.

(56) References Cited

U.S. PATENT DOCUMENTS
| 2007/0093540 A1 | 4/2007 | Allegrini et al. |
| 2009/0197886 A1* | 8/2009 | Liotta et al. ............ 514/236.5 |
| 2010/0076026 A1* | 3/2010 | Benson et al. ............ 514/338 |

FOREIGN PATENT DOCUMENTS
| WO | WO 2007/052843 | 5/2007 |
| WO | WO 2007/140174 | 12/2007 |

OTHER PUBLICATIONS

Domazon, R et al, *Jour of Heterocylic Chemistry*, 19:117-121 (1982) XP002560056.
Zhang et al., Tetrahedron Lett.., 47, pp. 7641-7644 (2006).
Corey et al., J. Am. Chem. Soc., 109, pp. 5551-5553 (1987).
Ramachandran et al., Tetrahedron: Asymmetry, 5, pp. 1061-1074 (1994).
Liu et al., Heterocycles, 71, pp. 1755-1763 (2007).
Grieder et al., Synthesis, 11, pp. 1707-1711 (2003).
Lyga et al., Pesticide Science, 42, pp. 29-36 (1994).
Hazeldine et al., Bioorganic & Medicinal Chem., 13, pp. 3910-3920 (2005).
Shirtcliff et al., J. Org. Chem., 71, pp. 6619-6622 (2006).

* cited by examiner

*Primary Examiner* — Kamal Saeed
*Assistant Examiner* — Nyeemah Grazier
(74) *Attorney, Agent, or Firm* — George W. Johnston; Dennis P. Tramaloni

(57) ABSTRACT

This invention relates to novel indazole or 4,5,6,7-tetrahydro-indazole derivatives of formula I

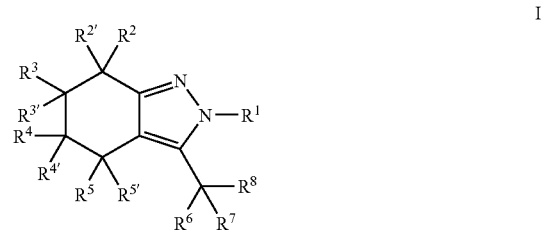

wherein $R^1$ to $R^8$ are as defined in the description and in the claims, as well as physiologically acceptable salts thereof. These compounds are FXR modulators and can be used as medicaments.

30 Claims, No Drawings

INDAZOLE OR 4,5,6,7-TETRAHYDRO-INDAZOLE DERIVATIVES

PRIORITY TO RELATED APPLICATION(S)

This application claims the benefit of European Patent Application No. 08165145.7, filed Sep. 25, 2008, which is hereby incorporated by reference in its entirety.

FIELD OF THE INVENTION

The present invention is concerned with indazole or 4,5,6,7-tetrahydro-indazole derivatives, their manufacture, pharmaceutical compositions containing them and their use as medicaments.

BACKGROUND OF THE INVENTION

The farnesoid-X-receptor (FXR) is a member of the nuclear hormone receptor superfamily of transcription factors. FXR was originally identified as a receptor activated by farnesol, and subsequent studies revealed a major role of FXR as a bile acid receptor [Makishima, M., Okamoto, A. Y., Repa, J. J., Tu, H., Learned, R. M., Luk, A., Hull, M. V., Lustig, K. D., Mangelsdorf, D. J. and Shan, B. (1999) Identification of a nuclear receptor for bile acids. Science 284, 1362-5]. FXR is expressed in liver, intestine, kidney, and the adrenal gland. Four splice isoforms have been cloned in humans.

Among the major bile acids, chenodeoxycholic acid is the most potent FXR agonist. Binding of bile acids or synthetic ligands to FXR induces the transcriptional expression of small heterodimer partner (SHP), an atypical nuclear receptor family member that binds to several other nuclear hormone receptors, including LRH-1 and LXR alpha and blocks their transcriptional functions [Lu, T. T., Makishima, M., Repa, J. J., Schoonjans, K., Kerr, T. A., Auwerx, J. and Mangelsdorf, D. J. (2000) Molecular basis for feedback regulation of bile acid synthesis by nuclear receptors. Mol Cell 6, 507-15]. CYP7A1 and CYP8B are enzymes involved in hepatic bile acid synthesis. FXR represses their expression via activation of the SHP pathway. FXR directly induces the expression of bile acid-exporting transporters for the ABC family in hepatocytes, including the bile salt export pump (ABCB11) and the multidrug resistance associated protein 2 (ABCC2) [Kast, H. R., Goodwin, B., Tarr, P. T., Jones, S. A., Anisfeld, A. M., Stoltz, C. M., Tontonoz, P., Kliewer, S., Willson, T. M. and Edwards, P. A. (2002) Regulation of multidrug resistance-associated protein 2 (ABCC2) by the nuclear receptors pregnane X receptor, farnesoid X-activated receptor, and constitutive androstane receptor. J Biol Chem 277, 2908-15; Ananthanarayanan, M., Balasubramanian, N., Makishima, M., Mangelsdorf, D. J. and Suchy, F. J. (2001) Human bile salt export pump promoter is transactivated by the farnesoid X receptor/bile acid receptor. J Biol Chem 276, 28857-65]. FXR knockout mice have impaired resistance to bile acid-induced hepatotoxicity and synthetic FXR agonists have been shown to be hepatoprotective in animal models of cholestasis [Liu, Y., Binz, J., Numerick, M. J., Dennis, S., Luo, G., Desai, B., MacKenzie, K. I., Mansfield, T. A., Kliewer, S. A., Goodwin, B. and Jones, S. A. (2003) Hepatoprotection by the farnesoid X receptor agonist GW4064 in rat models of intra- and extra-hepatic cholestasis. J Clin Invest 112, 1678-87; Sinal, C. J., Tohkin, M., Miyata, M., Ward, J. M., Lambert, G. and Gonzalez, F. J. (2000) Targeted disruption of the nuclear receptor FXR/BAR impairs bile acid and lipid homeostasis. Cell 102, 731-44]. These data show that FXR protects hepatocytes from bile acid toxicity by suppressing both cellular synthesis and import of bile acids and stimulating their biliary excretion.

The process of enterohepatic circulation of bile acids is also a major regulator of serum cholesterol homeostasis. After biosynthesis from cholesterol in the liver, bile acids are secreted with bile into the lumen of the small intestine to aid in the digestion and absorption of fat and fat-soluble vitamins. The ratio of different bile acids determines the hydrophilicity of the bile acid pool and its ability to solubilize cholesterol. FXR activation increases the hydrophilicity of the pool, decreasing the intestinal solubilization of cholesterol, effectively blocking its absorption. Decrease absorption would be expected to result in lowering of plasma cholesterol levels. Indeed direct inhibitors of cholesterol absorption such as ezetimibe decrease plasma cholesterol, providing some evidence to support this hypothesis. However ezetimibe has limited efficacy which appears due to feedback upregulation of cholesterol synthesis in cells attempting to compensate for depletion of cholesterol. Recent data have shown that FXR opposes this effect in part by directly repressing the expression of HMGCoA reductase via a pathway involving SHP and LRH1 [Datta, S., Wang, L., Moore, D. D. and Osborne, T. F. (2006) Regulation of 3-hydroxy-3-methylglutaryl coenzyme A reductase promoter by nuclear receptors liver receptor homologue-1 and small heterodimer partner: a mechanism for differential regulation of cholesterol synthesis and uptake. J Biol Chem 281, 807-12]. FXR also decreases hepatic synthesis of triglycerides by repressing SREBP1-c expression by an alternate pathway involving SHP and LXRalpha. Thus compounds which modulate FXR activity may show superior therapeutic efficacy on plasma cholesterol and triglyceride lowering than current therapies.

Most patients with coronary artery disease have high plasma levels of atherogenic LDL. The HMGCoA reductase inhibitors (statins) are effective at normalizing LDL-C levels but reduce the risk for cardiovascular events such as stroke and myocardial infarction by only about 30%. Additional therapies targeting further lowering of atherogenic LDL as well as other lipid risk factors such as high plasma triglyceride levels and low HDL-C levels are needed.

A high proportion of type 2 diabetic patients in the United States have abnormal concentrations of plasma lipoproteins. The prevalence of total cholesterol>240 mg/dl is 37% in diabetic men and 44% in diabetic women and the prevalence for LDL-C>160 mg/dl are 31% and 44%, respectively in these populations. Diabetes is a disease in which a patient's ability to control glucose levels in blood is decreased because of partial impairment in the response to insulin. Type II diabetes (T2D), also called non-insulin dependent diabetes mellitus (NIDDM), accounts for 80-90% of all diabetes cases in developed countries. In T2D, the pancreatic Islets of Langerhans produce insulin but the primary target tissues (muscle, liver and adipose tissue) develop a profound resistance to its effects. The body compensates by producing more insulin ultimately resulting in failure of pancreatic insulin-producing capacity. Thus T2D is a cardiovascular-metabolic syndrome associated with multiple co-morbidities including dyslipidemia and insulin resistance, as well as hypertension, endothelial dysfunction and inflammatory atherosclerosis.

The first line treatment for dyslipidemia and diabetes is a low-fat and low-glucose diet, exercise and weight loss. Compliance can be moderate and treatment of the various metabolic deficiencies that develop becomes necessary with, for example, lipid-modulating agents such as statins and fibrates, hypoglycemic drugs such as sulfonylureas and metformin, or insulin sensitizers of the thiazolidinedione (TZD) class of PPARgamma-agonists. Recent studies provide evidence that modulators of FXR may have enhanced therapeutic potential by providing superior normalization of both LDL-C and triglyceride levels, currently achieved only with combinations of existing drugs and, in addition, may avoid feedback effects on cellular cholesterol homeostasis.

The compounds of the present invention bind to and selectively modulate FXR very efficiently, resulting in reducing cholesterol absorption lowering LDL cholesterol and triglycerides and reducing inflammatory atherosclerosis. Since multiple facets of combined dyslipidemia and cholesterol homeostasis are addressed by FXR modulators, they are expected to have an enhanced therapeutic potential compared to the compounds already known in the art.

SUMMARY OF THE INVENTION

The present invention is concerned with indazole or 4,5,6, 7-tetrahydro-indazole derivatives, their manufacture, pharmaceutical compositions containing them and their use as medicaments.

In particular, the present invention relates to compounds of the formula

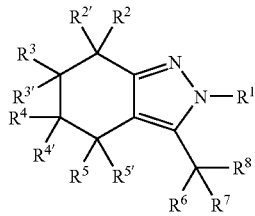

I wherein
$R^1$ is a ring selected from the group consisting of phenyl, naphthyl and heteroaryl, said ring being unsubstituted or substituted with 1 to 3 substituents independently selected from the group consisting of lower alkyl, halogen, lower halogenalkyl, hydroxy, lower alkoxy, lower halogenalkoxy and cyano;
$R^2$, $R^3$, $R^4$ and $R^5$ independently from each other are selected from the group consisting of hydrogen, halogen or lower alkyl;
$R^{2'}$ and $R^{3'}$ together as well as $R^{4'}$ and $R^{5'}$ together are replaced by a double bond, or $R^{2'}$, $R^{3'}$, $R^{4'}$ and $R^{5'}$ are hydrogen;
$R^6$ is selected from the group consisting of hydrogen, methyl, ethyl, hydroxy, methoxy, fluoro, fluoromethyl, difluoromethyl and trifluoromethyl;
$R^7$ is selected from the group consisting of lower alkyl, cycloalkyl, lower cycloalkylalkyl, lower alkoxyalkyl, unsubstituted phenyl or phenyl substituted with 1 to 3 substituents independently selected from the group consisting of lower alkyl, halogen, lower halogenalkyl, hydroxy, lower alkoxy, lower halogenalkoxy and cyano, lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy and cyano,
unsubstituted heteroaryl or heteroaryl substituted with 1 to 3 substituents independently selected from the group consisting of lower alkyl, halogen, lower halogenalkyl, hydroxy, lower alkoxy, lower halogenalkoxy and cyano, and
heterocyclyl; and
$R^8$ is selected from the group consisting of —C(O)—NH—$R^9$,
—$CR^{11}R^{12}$—$OR^{10}$, —O—$(CR^{11}R^{12})_n$—$R^{10}$;
—$CR^{11}R^{12}$—$SR^{10}$, —$CR^{11}R^{12}$—$SO_2$—$R^{10}$,
—$CR^{11}R^{12}$—$NR^{13}$—$R^{10}$; —CH=CH—$R^{10}$ and
—$(CH_2)_p$—$R^{10}$,
wherein
n is 0 or 1, p is 2,
$R^9$ is selected from the group consisting of
lower alkyl, cycloalkyl, lower cycloalkylalkyl,
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl,
unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl;
$R^{10}$ is selected from the group consisting of
lower alkyl, cycloalkyl, lower cycloalkylalkyl, cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl,
unsubstituted pyridyl and pyridyl substituted by carboxyl, lower alkoxycarbonyl or tetrazolyl,
unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl, and lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl;
$R^{11}$ and $R^{12}$ independently are selected from the group consisting of hydrogen, lower alkyl and lower halogenalkyl, or $R^{11}$ and $R^{12}$ together with the carbon atom to which they are attached form a cycloalkyl or alkoxycycloalkyl ring; and
$R^{13}$ is selected from the group consisting of hydrogen, lower alkyl and lower halogenalkyl;
or pharmaceutically acceptable salts thereof.

The compounds are selective modulators of the farnesoid-X-receptor, preferably agonists of the farnesoid-X-receptor. The compounds of the present invention bind to and selectively modulate FXR very efficiently, resulting in reducing cholesterol absorption lowering LDL cholesterol and triglycerides and reducing inflammatory atherosclerosis. Since multiple facets of combined dyslipidemia and cholesterol homeostasis are addressed by FXR modulators, they are expected to have an enhanced therapeutic potential compared to the compounds already known in the art.

DETAILED DESCRIPTION OF THE INVENTION

A. Definitive

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term "$C_{1-10}$-alkyl" refers to a branched or straight-chain monovalent saturated aliphatic hydrocarbon radical of one to ten carbon atoms, such as e.g. methyl, ethyl, n-propyl, isopropyl, n-butyl, s-butyl, t-butyl, pentyl, 1,1,3,3-tetramethyl-butyl and the like. Lower alkyl groups as described below also are preferred alkyl groups.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_{1-7}$ alkyl groups are methyl, ethyl, propyl, isopropyl, butyl, isobutyl, tert.-butyl, the isomeric pentyls, the isomeric hexyls and the isomeric heptyls, preferably methyl and ethyl and most preferred methyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclobutyl and cyclopentyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by cycloalkyl. A preferred example is cyclopropylmethyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, preferably methoxy and ethoxy.

The term "cycloalkyloxy" or "$C_{3-7}$-cycloalkyloxy" refers to the group R"—O—, wherein R" is cycloalkyl. Examples of cycloalkyloxy groups are cyclopropyloxy, cyclobutyloxy, cyclopentyloxy, cyclohexyloxy and cycloheptyloxy. Most preferred is cyclopropyloxy.

The term "alkoxycycloalkyl" denotes the saturated $C_{3-7}$-cycloalkyl group as defined above, however one of 3 to 7 carbon atoms is replaced by an O atom. Examples of "alkoxycycloalkyl" groups are oxirane, oxetane, tetrahydrofuran and tetrahydropyrane. A preferred example is oxirane.

The term "lower halogenalkyl" or "halogen-$C_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, trifluoroethyl, 2,2-difluoroethyl, fluoromethyl and chloromethyl, with trifluoromethyl or 2,2-difluoroethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkoxy groups are trifluoromethoxy, difluoromethoxy, fluoromethoxy and chloromethoxy, with trifluoromethoxy being especially preferred.

The term "carboxyl" means the group —COOH.

The term "lower alkoxycarbonyl" or "$C_{1-7}$-alkoxycarbonyl" refers to the group —CO—OR' wherein R' is lower alkyl and the term "lower alkyl" has the previously given significance. Preferred lower alkoxycarbonyl groups are methoxycarbonyl or ethoxycarbonyl.

The term "lower alkoxycarbonylalkyl" or "$C_{1-7}$-alkoxycarbonyl-$C_{1-7}$-alkyl" means lower alkyl groups as defined above wherein one of the hydrogen atoms of the lower alkyl group is replaced by $C_{1-7}$-alkoxycarbonyl. A preferred lower alkoxycarbonylalkyl group is —CH$_2$—COOCH$_3$.

The term "lower alkoxycarbonylalkoxy" or "$C_{1-7}$-alkoxycarbonyl-$C_{1-7}$-alkoxy" refers to lower alkoxy groups as defined above wherein one of the hydrogen atoms of the lower alkoxy group is replaced by $C_{1-7}$-alkoxycarbonyl. A preferred lower alkoxycarbonylalkoxy group is t-butoxycarbonylmethoxy (—O—CH$_2$—COO—C(CH$_3$)$_3$).

The term "lower carboxylalkyl" or "carboxyl-$C_{1-7}$-alkyl" refers to lower alkyl groups as defined above wherein at least one of the hydrogen atoms of the lower alkyl group is replaced by a carboxyl group. Among the preferred lower carboxyl alkyl groups are carboxylmethyl (—CH$_2$—COOH) and carboxylethyl (—CH$_2$—CH$_2$—COOH), with carboxylmethyl being especially preferred.

The term "lower carboxylalkoxy" or "carboxyl-$C_{1-7}$-alkoxy" refers to lower alkoxy groups as defined above wherein at least one of the hydrogen atoms of the lower alkoxy group is replaced by a carboxyl group. Preferred lower carboxylalkoxy group is carboxylmethoxy (—O—CH$_2$—COOH).

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furyl, pyridyl, 2-oxo-1,2-dihydro-pyridyl, pyridazinyl, pyrimidinyl, pyrazinyl, thiophenyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzoimidazolyl, indolyl, isoindolyl, 1,3-dioxo-isoindolyl, quinolinyl, indazolyl, benzoisothiazolyl, benzoxazolyl, benzoisoxazolyl, benzothiophenyl, benzothiazolyl, benzofuranyl and quinoxalinyl. Preferred heteroaryl groups are pyridyl, pyrimidinyl, oxazolyl, benzodioxolyl, thiophenyl, pyrrolyl, 2-oxo-1,2-dihydro-pyridinyl, indolyl, quinolinyl, 1,3-dioxo-isoindolyl, imidazolyl, benzothiophenyl, benzothiazolyl, benzofuranyl, quinoxalinyl, pyrazolyl, isoxazolyl, benzimidazolyl and furyl, with pyridyl being most preferred.

The term "heterocyclyl" refers to 5 to 6 membered monocyclic ring or 8 to 10 membered bi- or tricyclic ring which can comprise 1, 2 or 3 atoms selected from nitrogen, oxygen and/or sulphur, such as morpholinyl, thiomorpholinyl, 1,1-dioxo-thiomorpholinyl, piperidinyl, 2-oxo-piperidinyl, pyrrolidinyl, 2-oxo-pyrrolidinyl, piperazin-2-one, 8-oxa-3-aza-bicyclo[3.2.1]octyl, piperazinyl, tetrahydrofuranyl and tetrahydropyranyl. Preferred heterocyclyl groups are tetrahydrofuranyl and tetrahydropyranyl.

The term "protecting group" refers to groups which are used to protect functional groups, particularly hydroxy groups, temporarily. Examples of protecting groups are benzyl, p-methoxybenzyl, t-butyl-dimethylsilyl, t-butyl-diphenylsilyl and (for protection of amino groups) Boc and benzyloxycarbonyl.

Compounds of formula I can form pharmaceutically acceptable salts. Examples of such pharmaceutically acceptable salts are acid addition salts of compounds of formula I with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula I in which a COOH group is present can further form salts with bases. Examples of such salts are alkaline, earth-alkaline and ammonium salts such as e.g. Na—, K—, Ca— and trimethylammoniumsalt. The term "pharmaceutically acceptable salts" also refers to such salts.

B. Detailed Description

In detail, the present invention relates to compounds of the formula

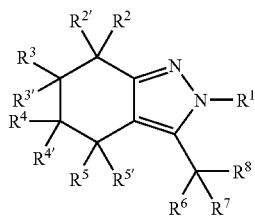

I wherein
$R^1$ is a ring selected from the group consisting of phenyl, naphthyl and heteroaryl, said ring being unsubstituted or substituted with 1 to 3 substituents independently selected from the group consisting of lower alkyl, halogen, lower halogenalkyl, hydroxy, lower alkoxy, lower halogenalkoxy and cyano;
$R^2$, $R^3$, $R^4$ and $R^5$ independently from each other are selected from the group consisting of hydrogen, halogen or lower alkyl;
$R^{2'}$ and $R^{3'}$ together as well as $R^{4'}$ and $R^{5'}$ together are replaced by a double bond, or $R^{2'}$, $R^{3'}$, $R^{4'}$ and $R^{5'}$ are hydrogen;
$R^6$ is selected from the group consisting of hydrogen, methyl, ethyl, hydroxy, methoxy, fluoro, fluoromethyl, difluoromethyl and trifluoromethyl;
$R^7$ is selected from the group consisting of lower alkyl, cycloalkyl, lower cycloalkylalkyl, lower alkoxyalkyl,
unsubstituted phenyl or phenyl substituted with 1 to 3 substituents independently selected from the group consisting of lower alkyl, halogen, lower halogenalkyl, hydroxy, lower alkoxy, lower halogenalkoxy and cyano,
lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy and cyano, unsubstituted heteroaryl or heteroaryl substituted with 1 to 3 substituents independently selected from the group consisting of lower alkyl, halogen, lower halogenalkyl, hydroxy, lower alkoxy, lower halogenalkoxy and cyano, and heterocyclyl; and
$R^8$ is selected from the group consisting of —C(O)—NH—$R^9$,
—$CR^{11}R^{12}$—$OR^{10}$, —O—$(CR^{11}R^{12})_n$—$R^{10}$;
—$CR^{11}R^{12}$—$SR^{10}$, —$CR^{11}R^{12}$—$SO_2$—$R^{10}$,
—$CR^{11}R^{12}$—$NR^{13}$—$R^{10}$; —CH=CH—$R^{10}$ and
—$(CH_2)_p$—$R^{10}$,
wherein
n is 0 or 1, p is 2,
$R^9$ is selected from the group consisting of lower alkyl, cycloalkyl, lower cycloalkylalkyl, cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl,
unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl;
$R^{10}$ is selected from the group consisting of
lower alkyl, cycloalkyl, lower cycloalkylalkyl,
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl,
unsubstituted pyridyl and pyridyl substituted by carboxyl, lower alkoxycarbonyl or tetrazolyl,
unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl, and
lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl;
$R^{11}$ and $R^{12}$ independently are selected from the group consisting of hydrogen, lower alkyl and lower halogenalkyl,
or $R^{11}$ and $R^{12}$ together with the carbon atom to which they are attached form a cycloalkyl or alkoxycycloalkyl ring; and
$R^{13}$ is selected from the group consisting of hydrogen, lower alkyl and lower halogenalkyl;
or pharmaceutically acceptable salts thereof.

Compounds of formula I are individually preferred and physiologically acceptable salts thereof are individually preferred, with the compounds of formula I being particularly preferred.

Preferred are further compounds of formula I according to the present invention, wherein $R^1$ is a phenyl ring, said ring being unsubstituted or substituted with 1 to 3 substituents independently selected from the group consisting of lower alkyl, halogen, lower halogenalkyl, hydroxy, lower alkoxy, lower halogenalkoxy and cyano. Especially preferred are the compounds of formula I according to the invention, wherein $R^1$ is phenyl or phenyl substituted with halogen.

Further preferred compounds of formula I according to the invention are those, wherein $R^2$, $R^3$, $R^4$ and $R^5$ independently from each other are selected from hydrogen or halogen. Especially preferred are compounds of formula I, wherein $R^2$, $R^3$, $R^4$ and $R^5$ are hydrogen.

Preferred are further compounds of formula I of the present invention, wherein $R^{2'}$ and $R^{3'}$ together as well as $R^{4'}$ and $R^{5'}$ together are replaced by a double bond, meaning these are compounds having the formula

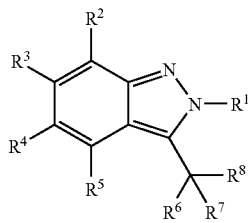

Ia wherein $R^1$ to $R^8$ are as defined herein before.

Within this group, compounds of formula Ia are preferred, wherein $R^2$ and $R^5$ are hydrogen and $R^3$ and $R^4$ are halogen, preferably fluoro.

Another group of preferred compounds of formula I of the present invention are those, wherein $R^{2'}$, $R^{3'}$, $R^{4'}$ and $R^{5'}$ are hydrogen, with those compounds being especially preferred, wherein also $R^2$, $R^3$, $R^4$ and $R^5$ are hydrogen, meaning compounds having the formula

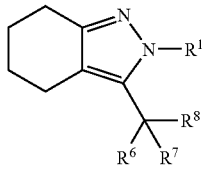

Ib wherein $R^1$, $R^6$, $R^7$ and $R^8$ are as defined herein before.

Furthermore, compounds of formula I according to the invention are preferred, wherein $R^6$ is selected from the group consisting of hydrogen, methyl, ethyl, hydroxy, methoxy, fluoro, fluoromethyl, difluoromethyl and trifluoromethyl, with those compounds of formula I being more preferred, wherein $R^6$ is selected from the group consisting of hydrogen, hydroxy and fluoro, and those compounds of formula I being most preferred, wherein $R^6$ is hydrogen or hydroxy. Especially preferred are compounds of formula I, wherein $R^6$ is hydrogen.

Also preferred are compounds of formula I, wherein $R^7$ is selected from the group consisting of cycloalkyl, unsubstituted phenyl and phenyl substituted with 1 to 3 substituents independently selected from the group consisting of lower alkyl, halogen, lower halogenalkyl, hydroxy, lower alkoxy, lower halogenalkoxy and cyano. Especially preferred are compounds of formula I, wherein $R^7$ is cycloalkyl, most preferably cyclohexyl. Further especially preferred compounds of formula I are those, wherein $R^7$ is phenyl substituted by lower alkoxy.

In addition, compounds of formula I according to the invention are preferred, wherein $R^8$ is selected from the group consisting of —C(O)—NH—$R^9$, —$CR^{11}R^{12}$—$OR^{10}$, —O—$(CR^{11}R^{12})_n$—$R^{10}$; —$CR^{11}R^{12}$—$SR^{10}$, —$CR^{11}R^{12}$—$SO_2$—$R^{10}$ and —$CR^{11}R^{12}$—$NR^{13}$—$R^{10}$.

Especially preferred are compounds of formula I, wherein $R^8$ is —C(O)—NH—$R^9$ and $R^9$ is selected from the group consisting of lower alkyl, cycloalkyl, lower cycloalkylalkyl, cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl, unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl.

Within this group, compounds of formula I are more preferred, wherein $R^9$ is selected from the group consisting of cycloalkyl, cycloalkyl substituted by hydroxy, unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl, with those compounds of formula I being more preferred, wherein $R^9$ is selected from the group consisting of cycloalkyl, cycloalkyl substituted by hydroxy and phenyl substituted with 1 to 3 substituents independently selected from halogen and carboxyl, and those compounds of formula I being most preferred, wherein $R^9$ is cycloalkyl, most preferably cyclopentyl or cyclohexyl.

In addition, compounds of formula I are also very preferred, wherein $R^9$ is phenyl substituted with 1 to 3 substituents independently selected from halogen, lower halogenalkyl, lower alkyl, carboxyl, tetrazolyl, cyano and cycloalkyloxy wherein the cycloalkyl group is substituted by carboxyl or lower alkoxycarbonyl.

Another group of preferred compounds of formula I according to the present invention are those, wherein $R^8$ is —$CR^{11}R^{12})_n$—$R^{10}$ wherein n is 0 or 1, $R^{10}$ is selected from the group consisting of
  lower alkyl, cycloalkyl, lower cycloalkylalkyl,
  cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl,
  unsubstituted pyridyl and pyridyl substituted by carboxyl, lower alkoxycarbonyl or tetrazolyl,
  unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl, and lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl; and $R^{11}$ and $R^{12}$ independently are selected from the group consisting of hydrogen, lower alkyl and lower halogenalkyl, or $R^{11}$ and $R^{12}$ together with the carbon atom to which they are attached form a cycloalkyl or alkoxycycloalkyl ring.

Preferably, $R^{10}$ is selected from the group consisting of unsubstituted pyridyl, pyridyl substituted by carboxyl, lower alkoxycarbonyl or tetrazolyl, unsubstituted phenyl, and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl.

More preferably, $R^{10}$ is pyridyl substituted by carboxyl or phenyl substituted with 1 to 3 substituents independently selected from the group consisting of lower alkyl, halogen, carboxyl, tetrazolyl, lower alkoxycarbonyl, cyano and cycloalkyloxy wherein the cycloalkyl group is substituted by carboxyl or lower alkoxycarbonyl.

Preferably, $R^{11}$ and $R^{12}$ are hydrogen.

Another group of preferred compounds of formula I according to the present invention are those, wherein $R^8$ is selected from the group consisting of —$CR^{11}R^{12}$—$SR^{10}$, —$CR^{11}R^{12}$—$SO_2$—$R^{10}$ and $CR^{11}R^{12}$—$NR^{13}$—$R^{10}$ and wherein $R^{10}$ is selected from the group consisting of lower alkyl, cycloalkyl, lower cycloalkylalkyl, cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl, unsubstituted pyridyl and pyridyl substituted by carboxyl, lower alkoxycarbonyl or tetrazolyl, unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl, and lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl;

$R^{11}$ and $R^{12}$ independently are selected from the group consisting of hydrogen, lower alkyl and lower halogenalkyl, or $R^{11}$ and $R^{12}$ together with the carbon atom to which they are attached form a cycloalkyl or alkoxycycloalkyl ring; and $R^{13}$ is selected from the group consisting of hydrogen, lower alkyl and lower halogenalkyl.

Preferably, $R^{13}$ is hydrogen.

A further group of preferred compounds of formula I are those, wherein $R^8$ is —CH=CH—$R^{10}$ or —$(CH_2)_p$—$R^{10}$, wherein p is 2, and wherein $R^{10}$ is selected from the group consisting of lower alkyl, cycloalkyl, lower cycloalkylalkyl, cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl, unsubstituted pyridyl and pyridyl substituted by carboxyl, lower alkoxycarbonyl or tetrazolyl, unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl, and lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl.

In addition, preferred compounds of the formula I are those having the formula

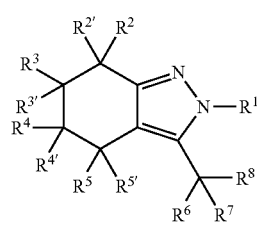

I-A wherein $R^1$ is a ring selected from phenyl, naphthyl and heteroaryl, said ring being unsubstituted or substituted with 1 to 3 substituents independently selected from the group consisting of lower alkyl, halogen, lower halogenalkyl, hydroxy, lower alkoxy, lower halogenalkoxy and cyano;

$R^2$, $R^3$, $R^4$ and $R^5$ independently from each other are selected from the group consisting of hydrogen, halogen or lower alkyl;

$R^{2'}$ and $R^{3'}$ together as well as $R^{4'}$ and $R^{5'}$ together are replaced by a double bond, or $R^{2'}$, $R^{3'}$, $R^{4'}$ and $R^{5'}$ are hydrogen;

R⁶ is selected from the group consisting of hydrogen, methyl, ethyl, hydroxy, methoxy, fluoro, fluoromethyl, difluoromethyl and trifluoromethyl;

R⁷ is selected from the group consisting of lower alkyl, cycloalkyl, lower cycloalkylalkyl, lower alkoxyalkyl,
unsubstituted phenyl or phenyl substituted with 1 to 3 substituents independently selected from the group consisting of lower alkyl, halogen, lower halogenalkyl, hydroxy, lower alkoxy, lower halogenalkoxy and cyano,
lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy and cyano,
unsubstituted heteroaryl or heteroaryl substituted with 1 to 3 substituents independently selected from the group consisting of lower alkyl, halogen, lower halogenalkyl, hydroxy, lower alkoxy, lower halogenalkoxy and cyano, and heterocyclyl; and R⁸ is selected from the group consisting of —C(O)—NH—R⁹, —CR¹¹R¹²—OR¹⁰ and —O—CR¹¹R¹²—R¹⁰; wherein R⁹ is selected from the group consisting of
lower alkyl, cycloalkyl, lower cycloalkylalkyl, cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl,
unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl or tetrazolyl;

R¹⁰ is selected from the group consisting of
lower alkyl, cycloalkyl, lower cycloalkylalkyl, cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl,
unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl or tetrazolyl, and
lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl or tetrazolyl; and R¹¹ and R¹² independently are selected from the group consisting of hydrogen, lower alkyl and lower halogenalkyl, or R¹¹ and R¹² together with the carbon atom to which they are attached form a cycloalkyl or alkoxycycloalkyl ring;
or pharmaceutically acceptable salts thereof.

Particularly preferred compounds of formula I of the invention are selected from the group consisting of
2,N-dicyclohexyl-2-(2-phenyl-2H-indazol-3-yl)-acetamide,
N-cyclohexyl-2-(3-methoxy-phenyl)-2-(2-phenyl-2H-indazol-3-yl)-acetamide,
N-cyclohexyl-2-phenyl-2-(2-phenyl-2H-indazol-3-yl)-acetamide,
2-[2-(4-chloro-phenyl)-2H-indazol-3-yl]-2,N-dicyclohexyl-acetamide,
4-{2-[2-(4-chloro-phenyl)-4,5,6,7-tetrahydro-2H-indazol-3-yl]-2-cyclohexyl-2-hydroxy-acetylamino}-3-fluoro-benzoic acid,
2-[2-(4-chloro-phenyl)-4,5,6,7-tetrahydro-2H-indazol-3-yl]-2,N-dicyclohexyl-acetamide,
4-{2-[2-(4-chloro-phenyl)-4,5,6,7-tetrahydro-2H-indazol-3-yl]-2-cyclohexyl-acetylamino}-benzoic acid,
2-[2-(4-chloro-phenyl)-4,5,6,7-tetrahydro-2H-indazol-3-yl]-2-cyclohexyl-N-cyclopentyl-acetamide,
2-[2-(4-chloro-phenyl)-4,5,6,7-tetrahydro-2H-indazol-3-yl]-2-cyclohexyl-N-cyclopentyl-2-hydroxy-acetamide,
2-[2-(4-chloro-phenyl)-2H-indazol-3-yl]-2-cyclohexyl-(trans)-N-(4-hydroxy-cyclohexyl)-acetamide,
4-{2-[2-(4-chloro-phenyl)-4,5,6,7-tetrahydro-2H-indazol-3-yl]-2-cyclohexyl-acetylamino}-3-fluoro-benzoic acid,
4-{2-[2-(4-chloro-phenyl)-2H-indazol-3-yl]-2-cyclohexyl-acetylamino}-benzoic acid,
4-{2-[2-(4-chloro-phenyl)-2H-indazol-3-yl]-2-cyclohexyl-acetylamino}-3-fluoro-benzoic acid,
2-[2-(4-chloro-phenyl)-4,5,6,7-tetrahydro-2H-indazol-3-yl]-2-cyclohexyl-N-(2,4-difluoro-phenyl)-acetamide,
1-(4-{2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid methyl ester,
1-(4-{2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid,
4-{[2-(4-chloro-phenyl)-2H-indazol-3-yl]-cyclohexyl-methoxymethyl}-benzoic acid methyl ester,
4-{[2-(4-chloro-phenyl)-2H-indazol-3-yl]-cyclohexyl-methoxymethyl}-benzoic acid,
4-{2-[2-(4-chloro-phenyl)-4,5,6,7-tetrahydro-2H-indazol-3-yl]-2-cyclohexyl-acetylamino}-3-trifluoromethyl-benzoic acid methyl ester,
4-{2-[2-(4-chloro-phenyl)-4,5,6,7-tetrahydro-2H-indazol-3-yl]-2-cyclohexyl-acetylamino}-3-trifluoromethyl-benzoic acid,
1-(4-{(S)-2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid tert-butyl ester,
1-(4-{(R)-2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid,
1-(4-{(S)-2-([2-(4-chloro-phenyl)-4,5,6,7-tetrahydro-2H-indazol-3-yl]-2-cyclohexyl-acetylamino}-3-fluoro-phenoxy)-cyclopropanecarboxylic acid,
2-[2-(4-chloro-phenyl)-5,6-difluoro-2H-indazol-3-yl]-2,N-dicyclohexyl-acetamide,
2-(4-{2-[2-(4-chloro-phenyl)-5,6-difluoro-2H-indazol-3-yl]-2-cyclohexyl-acetylamino}-3-fluoro-phenoxy)-2-methyl-propionic acid ethyl ester,
2-(4-{2-[2-(4-chloro-phenyl)-5,6-difluoro-2H-indazol-3-yl]-2-cyclohexyl-acetylamino}-3-fluoro-phenoxy)-2-methyl-propionic acid, 4-{[2-(4-chloro-phenyl)-5,6-difluoro-2H-indazol-3-yl]-cyclohexyl-methoxymethyl}-benzoic acid,
4-{[2-(4-chloro-phenyl)-4,5,6,7-tetrahydro-2H-indazol-3-yl]-cyclohexyl-methoxymethyl}-benzoic acid,
4-{2-[2-(4-chloro-phenyl)-2H-indazol-3-yl]-2-cyclohexyl-ethoxy}-3,5-dimethyl-benzoic acid,
4-{2-[2-(4-chloro-phenyl)-2H-indazol-3-yl]-2-cyclohexyl-ethoxy}-3-fluoro-benzonitrile,
2-(4-chloro-phenyl)-3-{1-cyclohexyl-2-[2-fluoro-4-(2H-tetrazol-5-yl)-phenoxy]ethyl}-2H-indazole,
4-{2-[2-(4-chloro-phenyl)-5,6-difluoro-2H-indazol-3-yl]-2-cyclohexyl-acetylamino}-3-fluoro-benzoic acid,
4-{[2-(4-chloro-phenyl)-5,6-difluoro-2H-indazol-3-yl]-cyclohexyl-methoxy}-3,5-dimethyl-benzoic acid methyl ester,
4-{[2-(4-chloro-phenyl)-5,6-difluoro-2H-indazol-3-yl]-cyclohexyl-methoxy}-3,5-dimethyl-benzoic acid,
4-{[2-(4-chloro-phenyl)-5,6-difluoro-2H-indazol-3-yl]-cyclohexyl-methoxy}-3-fluoro-benzonitrile,
2-(4-chloro-phenyl)-3-{1-cyclohexyl-2-[2-fluoro-4-(2H-tetrazol-5-yl)-phenoxy]-ethyl}-5,6-difluoro-2H-indazole,
4-{2-[2-(4-chloro-phenyl)-4,5,6,7-tetrahydro-2H-indazol-3-yl]-2-cyclohexyl-ethoxy}-3-fluoro-benzonitrile,
2-(4-chloro-phenyl)-3-{1-cyclohexyl-2-[2-fluoro-4-(1H-tetrazol-5-yl)-phenoxy]-ethyl}-4,5,6,7-tetrahydro-2H-indazole,
4-{2-[2-(4-chloro-phenyl)-4,5,6,7-tetrahydro-2H-indazol-3-yl]-2-cyclohexyl-ethoxy}-3,5-dimethyl-benzoic acid methyl ester,
4-{2-[2-(4-chloro-phenyl)-4,5,6,7-tetrahydro-2H-indazol-3-yl]-2-cyclohexyl-ethoxy}-3,5-dimethyl-benzoic acid,
4-{[2-(4-chloro-phenyl)-5,6-difluoro-2H-indazol-3-yl]-cyclohexyl-methoxymethyl}-3-fluoro-benzonitrile,
2-(4-chloro-phenyl)-3-{cyclohexyl-[2-fluoro-4-(2H-tetrazol-5-yl)-benzyloxy]-methyl}-5,6-difluoro-2H-indazole,
4-{2-[2-(4-chloro-phenyl)-5,6-difluoro-2H-indazol-3-yl]-2-cyclohexyl-ethoxy}-3,5-dimethyl-benzoic acid,
4-{[2-(4-chloro-phenyl)-4,5,6,7-tetrahydro-2H-indazol-3-yl]-cyclohexyl-methoxymethyl}-benzonitrile,
4-{[2-(4-chloro-phenyl)-2H-indazol-3-yl]-cyclohexyl-methoxymethyl}-3-fluoro-benzonitrile,
4-{[2-(4-chloro-phenyl)-2H-indazol-3-yl]-cyclohexyl-methoxymethyl}-benzonitrile,
2-(4-chloro-phenyl)-3-{cyclohexyl-[4-(2H-tetrazol-5-yl)-benzyloxy]-methyl}-2H-indazole,
4-{[2-(4-chloro-phenyl)-5,6-difluoro-2,1-indazol-3-yl]-cyclohexyl-methoxymethyl}-benzonitrile,
2-(4-chloro-phenyl)-3-{cyclohexyl-[4-(2H-tetrazol-5-yl)-benzyloxy]-methyl}-5,6-difluoro-2H-indazole,
2-(4-chloro-phenyl)-3-{cyclohexyl-[2-fluoro-4-(1H-tetrazol-5-yl)-phenoxy]-methyl}-5,6-difluoro-2H-indazole,
4-{2-[2-(4-chloro-phenyl)-2H-indazol-3-yl]-2-cyclohexyl-ethoxy}-3,5-dimethyl-benzonitrile,
2-(4-chloro-phenyl)-3-{1-cyclohexyl-2-[2,6-dimethyl-4-(2H-tetrazol-5-yl)-phenoxy]-ethyl}-2H-indazole,
6-{2-[2-(4-chloro-phenyl)-2H-indazol-3-yl]-2-cyclohexyl-ethoxy}-nicotinic acid,
1-(4-{2-[2-(4-chloro-phenyl)-2H-indazol-3-yl]-2-cyclohexyl-ethoxy}-phenoxy)-cyclopropanecarboxylic acid methyl ester,
1-(4-{2-[2-(4-chloro-phenyl)-4,5,6,7-tetrahydro-2H-indazol-3-yl]-2-cyclohexyl-ethoxy}-phenoxy)-cyclopropanecarboxylic acid,
1-(4-{[2-(4-chloro-phenyl)-5,6-difluoro-2H-indazol-3-yl]-cyclohexyl-methoxy}-phenoxy)-cyclopropanecarboxylic acid,
2-[2-(4-chloro-phenyl)-4,5,6,7-tetrahydro-2H-indazol-3-yl]-2-cyclohexyl-N-[4-(1H-tetrazol-5-yl)-phenyl]-acetamide,
2-[2-(4-chloro-phenyl)-4,5,6,7-tetrahydro-2H-indazol-3-yl]-2-cyclohexyl-N-[2-fluoro-4-(1H-tetrazol-5-yl)-phenyl]-acetamide,
2-[2-(4-chloro-phenyl)-4,5,6,7-tetrahydro-2H-indazol-3-yl]-2-cyclohexyl-(trans)-N-(4-hydroxy-cyclohexyl)-acetamide,
(4-{2-[2-(4-chloro-phenyl)-4,5,6,7-tetrahydro-2H-indazol-3-yl]-2-cyclohexyl-(trans)-acetylamino}-cyclohexyl)-acetic acid,
3-(4-{2-[2-(4-chloro-phenyl)-4,5,6,7-tetrahydro-2H-indazol-3-yl]-2-cyclohexyl-acetylamino}-3-fluoro-phenyl)-propionic acid,
3-chloro-4-{2-[2-(4-chloro-phenyl)-4,5,6,7-tetrahydro-2H-indazol-3-yl]-2-cyclohexyl-acetylamino}-benzoic acid,
4-{2-[2-(4-chloro-phenyl)-4,5,6,7-tetrahydro-2H-indazol-3-yl]-2-cyclohexyl-ethylsulfanyl}-benzoic acid,
6-{2-[2-(4-chloro-phenyl)-4,5,6,7-tetrahydro-2H-indazol-3-yl]-2-cyclohexyl-ethoxy}-nicotinic acid,
{2-[2-(4-chloro-phenyl)-4,5,6,7-tetrahydro-2H-indazol-3-yl]-2-cyclohexyl-ethyl}-[4-(1H-tetrazol-5-yl)-phenyl]-amine,
4-{2-[2-(4-chloro-phenyl)-4,5,6,7-tetrahydro-2H-indazol-3-yl]-2-cyclohexyl-ethanesulfonyl}-benzoic acid,
4-{(E)-3-[2-(4-chloro-phenyl)-4,5,6,7-tetrahydro-2H-indazol-3-yl]-3-cyclohexyl-propenyl}-benzoic acid,
4-[3-cyclohexyl-3-(2-phenyl-4,5,6,7-tetrahydro-2H-indazol-3-yl)-propyl]-benzoic acid,
and pharmaceutically acceptable salts thereof.

Especially preferred compounds of formula I are those selected from the group consisting of
2,N-dicyclohexyl-2-(2-phenyl-2H-indazol-3-yl)-acetamide,
N-cyclohexyl-2-phenyl-2-(2-phenyl-2H-indazol-3-yl)-acetamide,
4-{2-[2-(4-chloro-phenyl)-4,5,6,7-tetrahydro-2H-indazol-3-yl]-2-cyclohexyl-2-hydroxy-acetylamino}-3-fluoro-benzoic acid,
2-[2-(4-chloro-phenyl)-4,5,6,7-tetrahydro-2H-indazol-3-yl]-2,N-dicyclohexyl-acetamide,
2-[2-(4-chloro-phenyl)-2H-indazol-3-yl]-2-cyclohexyl-(trans)-N-(4-hydroxy-cyclohexyl)-acetamide,
4-{2-[2-(4-chloro-phenyl)-4,5,6,7-tetrahydro-2H-indazol-3-yl]-2-cyclohexyl-acetylamino}-3-fluoro-benzoic acid,
4-{2-[2-(4-chloro-phenyl)-2H-indazol-3-yl]-2-cyclohexyl-acetylamino}-3-fluoro-benzoic acid,
1-(4-{2-[2-(4-chloro-phenyl)-4,5,6,7-tetrahydro-2H-indazol-3-yl]-2-cyclohexyl-acetylamino}-fluoro-phenoxy)-cyclopropanecarboxylic acid,
4-{[2-(4-chloro-phenyl)-2H-indazol-3-yl]-cyclohexyl-methoxymethyl}-benzoic acid,
4-{2-[2-(4-chloro-phenyl)-4,5,6,7-tetrahydro-2H-indazol-3-yl]-2-cyclohexyl-acetylamino}-3-trifluoromethyl-benzoic acid,
1-(4-{(S)-2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid,
2-[2-(4-chloro-phenyl)-5,6-difluoro-2H-indazol-3-yl]-2,N-dicyclohexyl-acetamide,
2-(4-{2-[2-(4-chloro-phenyl)-5,6-difluoro-2H-indazol-3-yl]-2-cyclohexyl-acetylamino}-3-fluoro-phenoxy)-2-methyl-propionic acid,
4-{[2-(4-chloro-phenyl)-5,6-difluoro-2H-indazol-3-yl]-cyclohexyl-methoxymethyl}-benzoic acid,
4-{2-[2-(4-chloro-phenyl)-2H-indazol-3-yl]-2-cyclohexyl-ethoxy}-3,5-dimethyl-benzoic acid, 2-(4-chloro-phenyl)-3-{1-cyclohexyl-2-[2-fluoro-4-(2H-tetrazol-5-yl)-phenoxy]-ethyl}-2H-indazole,
4-{[2-(4-chloro-phenyl)-5,6-difluoro-2H-indazol-3-yl]-cyclohexyl-methoxy}-3-fluoro-benzonitrile,
2-(4-chloro-phenyl)-3-{1-cyclohexyl-2-[2-fluoro-4-(2H-tetrazol-5-yl)-phenoxy]-ethyl}-5,6-difluoro-2H-indazole,
2-(4-chloro-phenyl)-3-{1-cyclohexyl-2-[2-fluoro-4-(1H-tetrazol-5-yl)-phenoxy]-ethyl}-4,5,6,7-tetrahydro-2H-indazole,
4-{2-[2-(4-chloro-phenyl)-4,5,6,7-tetrahydro-2H-indazol-3-yl]-2-cyclohexyl-ethoxy}-3,5-dimethyl-benzoic acid,
2-(4-chloro-phenyl)-3-{cyclohexyl-[2-fluoro-4-(2H-tetrazol-5-yl)-benzyloxy]-methyl}-5,6-difluoro-2H-indazole,
4-{2-[2-(4-chloro-phenyl)-5,6-difluoro-2H-indazol-3-yl]-2-cyclohexyl-ethoxy}-3,5-dimethyl-benzoic acid,
2-(4-chloro-phenyl)-3-{cyclohexyl-[4-(2H-tetrazol-5-yl)-benzyloxy]-methyl}-2H-indazole,
2-(4-chloro-phenyl)-3-{cyclohexyl-[4-(2H-tetrazol-5-yl)-benzyloxy]-methyl}-5,6-difluoro-2H-indazole,
2-(4-chloro-phenyl)-3-{cyclohexyl-[2-fluoro-4-(1H-tetrazol-5-yl)-phenoxy]-methyl}-5,6-difluoro-2H-indazole,
2-(4-chloro-phenyl)-3-{1-cyclohexyl-2-[2,6-dimethyl-4-(2H-tetrazol-5-yl)-phenoxy]-ethyl}-2H-indazole,
6-{2-[2-(4-chloro-phenyl)-2H-indazol-3-yl]-2-cyclohexyl-ethoxy}-nicotinic acid,
1-(4-{2-[2-(4-chloro-phenyl)-4,5,6,7-tetrahydro-2H-indazol-3-yl]-2-cyclohexyl-ethoxy}-phenoxy)-cyclopropanecarboxylic acid,
1-(4-{[2-(4-chloro-phenyl)-5,6-difluoro-2H-indazol-3-yl]-cyclohexyl-methoxy}-phenoxy)-cyclopropanecarboxylic acid,
2-[2-(4-chloro-phenyl)-4,5,6,7-tetrahydro-2H-indazol-3-yl]-2-cyclohexyl-N-[2-fluoro-4-(1H-tetrazol-5-yl)-phenyl]-acetamide,
2-[2-(4-chloro-phenyl)-4,5,6,7-tetrahydro-2H-indazol-3-yl]-2-cyclohexyl-(trans)-N-(4-hydroxy-cyclohexyl)-acetamide,
(4-{2-[2-(4-chloro-phenyl)-4,5,6,7-tetrahydro-2H-indazol-3-yl]-2-cyclohexyl-(trans)-acetylamino}-cyclohexyl)-acetic acid,
3-(4-{2-[2-(4-chloro-phenyl)-4,5,6,7-tetrahydro-2H-indazol-3-yl]-2-cyclohexyl-acetylamino}-3-fluoro-phenyl)-propionic acid,
3-chloro-4-{2-[2-(4-chloro-phenyl)-4,5,6,7-tetrahydro-2H-indazol-3-yl]-2-cyclohexyl-acetylamino}-benzoic acid,
4-{2-[2-(4-chloro-phenyl)-4,5,6,7-tetrahydro-2H-indazol-3-yl]-2-cyclohexyl-ethylsulfanyl}-benzoic acid,
{2-[2-(4-chloro-phenyl)-4,5,6,7-tetrahydro-2H-indazol-3-yl]-2-cyclohexyl-ethyl}-[4-(1H-tetrazol-5-yl)-phenyl]-amine,
4-{2-[2-(4-chloro-phenyl)-4,5,6,7-tetrahydro-2H-indazol-3-yl]-2-cyclohexyl-ethanesulfonyl}-benzoic acid,
and pharmaceutically acceptable salts thereof.

Even more preferred compounds of formula I are those selected from the group consisting of
2-[2-(4-chloro-phenyl)-4,5,6,7-tetrahydro-2H-indazol-3-yl]-2,N-dicyclohexyl-acetamide,
4-{2-[2-(4-chloro-phenyl)-4,5,6,7-tetrahydro-2H-indazol-3-yl]-2-cyclohexyl-acetylamino}-3-fluoro-benzoic acid,
1-(4-{2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid,
1-(4-{(S)-2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid,
4-{2-[2-(4-chloro-phenyl)-2H-indazol-3-yl]-2-cyclohexyl-ethoxy}-3,5-dimethyl-benzoic acid,
2-(4-chloro-phenyl)-3-{1-cyclohexyl-2-[2-fluoro-4-(2H-tetrazol-5-yl)-phenoxy]-ethyl}-5,6-difluoro-2H-indazole,
2-(4-chloro-phenyl)-3-{1-cyclohexyl-2-[2-fluoro-4-(1H-tetrazol-5-yl)-phenoxy]-ethyl}-4,5,6,7-tetrahydro-2H-indazole,
2-(4-chloro-phenyl)-3-{cyclohexyl-[2-fluoro-4-(2H-tetrazol-5-yl)-benzyloxy]-methyl}-5,6-difluoro-2H-indazole,
4-{2-[2-(4-chloro-phenyl)-5,6-difluoro-2H-indazol-3-yl]-2-cyclohexyl-ethoxy}-3,5-dimethyl-benzoic acid,
2-(4-chloro-phenyl)-3-{cyclohexyl-[4-(2H-tetrazol-5-yl)-benzyloxy]-methyl-}-2H-indazole,
2-(4-chloro-phenyl)-3-{1-cyclohexyl-2-[2,6-dimethyl-4-(2H-tetrazol-5-yl)-phenoxy]-ethyl}-2H-indazole,
and pharmaceutically acceptable salts thereof.

The invention also relates to a process for the manufacture of compounds of formula I as defined above wherein $R^8$ is —C(O)—NH—$R^9$, which process comprises
a) reacting a carboxylic acid of the formula II

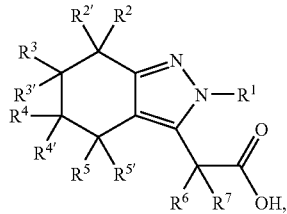

wherein $R^1$ to $R^7$ are as defined above, with an amine of the formula III

wherein $R^9$ is a defined above, in the presence of a coupling reagent under basic conditions to obtain a compound of the formula Ic

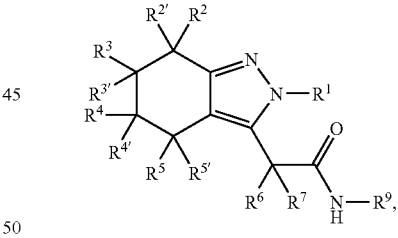

wherein $R^1$ to $R^7$ and $R^9$ are as defined above, and, if desired,
b) converting the compound obtained into a pharmaceutically acceptable salt.

Appropriate coupling agents are for example N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N',N'-tetramethyluronium tetrafluoroborate (TBTU), 1-[bis(dimethylamino)methylene]-1H-1,2,3-triazolo[4,5-b]pyridinium-3-oxide hexafluorophosphate (HATU) or benzotriazol-1-yloxytris(dimethylamino)phosphonium hexafluorophoshate (BOP), with EDCI, TBTU or BOP being preferred. Under basic conditions means the presence of a base such as diisopropylethylamine, triethylamine, N-methylmorpholine, optionally in the presence of 4-dimethylamino-pyridine or HOBt (1-hydroxybenzo-triazole). The reaction is carried out in a suitable solvent such as for example dichloromethane, DMF, DMA or dioxane at temperatures between 0° C. and ambient temperature.

The invention further relates to a process for the manufacture of compounds of formula I as defined above wherein $R^8$ is $-O-(CR^{11}R^{12})_n-R^{10}$ and n is 1, which process comprises a) reacting an alcohol of the formula IV

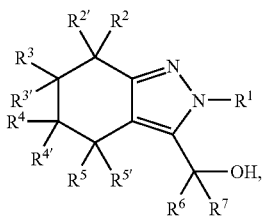

IV wherein $R^1$ to $R^7$ are as defined herein before, with a compound of the formula V

 V, wherein $R^{10}$ to $R^{12}$ are as defined herein before and X denotes a halide, mesylate or tosylate moiety,
to obtain a compound of formula Id

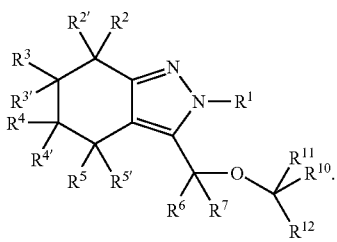

Id wherein $R^1$ to $R^{12}$ are as defined herein before, and, if desired,
b) converting the compound obtained into a pharmaceutically acceptable salt.

The invention also relates to a process for the manufacture of compounds of formula I as defined above wherein $R^8$ is $-CR^{11}R^{12}-OR^{10}$, which process comprises
a) reacting an alcohol of the formula VII

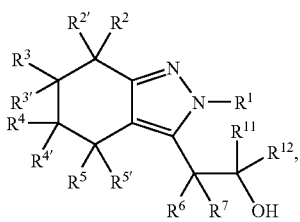

VII wherein $R^1$ to $R^7$ and $R^{11}$ and $R^{12}$ are as defined herein before, with a compound of the formula VIII

 VIII, wherein $R^{10}$ is as defined herein before and X denotes a halide, mesylate or tosylate moiety, or in case $R^{10}$ corresponds to phenyl a phenyl substituted as defined herein before, X denotes a hydroxy group,
to obtain a compound of formula Ie

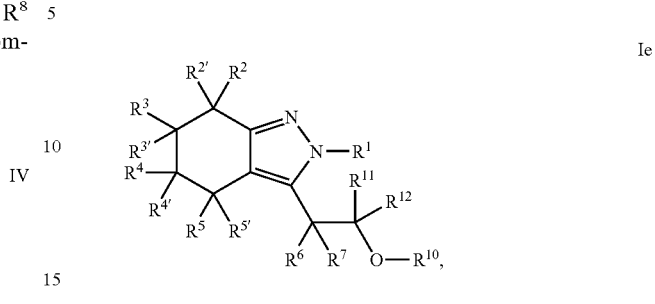

Ie wherein $R^1$ to $R^{12}$ are as defined herein before, and, if desired, b) converting the compound obtained into a pharmaceutically acceptable salt.

Compounds of formula VIII, wherein X denotes a halide, mesylate or tosylate moiety, can be reacted with compounds of formula VII in the presence of a weak base like cesium or potassium carbonate in solvents like N,N-dimethylformamide, acetonitrile, acetone or methyl-ethyl ketone at a temperature ranging from room temperature to 140° C., preferably around 50° C., whereas compounds of formula VIII, wherein X denotes a hydroxy group can be reacted with compounds of formula VII in the presence of triphenylphosphine and di-tert-butyl-, diisopropyl- or diethyl-azodicarboxylate or in the presence of tributylphosphine and N,N,N', N'-tetramethyl azodicarboxamide, preferably in a solvent like toluene, dichloromethane or tetrahydrofuran at ambient temperature.

In more detail, the compounds of formula I, which are the subject of this invention, can be manufactured as outlined in schemes A, B, C and D, by the methods given in the examples or by analogous methods. Unless otherwise indicated, $R^1$, $R^2$, $R^{2'}$, $R^3$, $R^{3'}$, $R^4$, $R^{4'}$, $R^5$, $R^{5'}$, $R^6$, $R^7$, $R^8$, $R^9$, $R^{10}$, and $R^{12}$ are as described above. The starting materials are either commercially available, described in the literature or can be prepared by methods well known in the art.

Scheme A

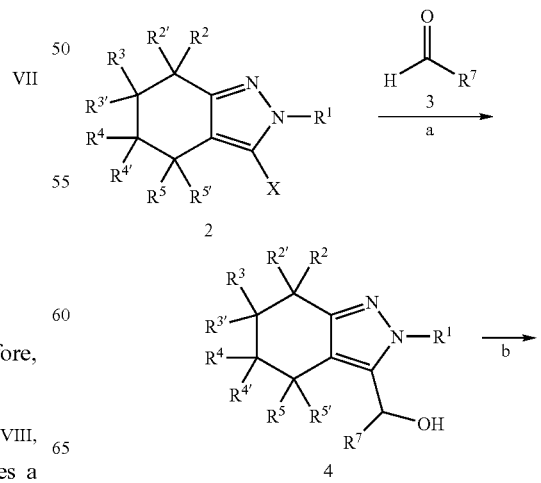

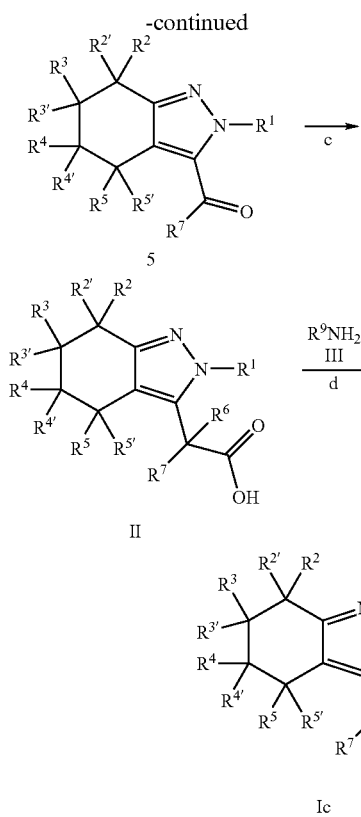

2H-Indazoles and 4,5,6,7-tetrahydro-2H-indazoles 2, wherein X corresponds to H, Cl, Br or I, are described in the literature, can be prepared by methods well known to a person skilled in the art or by methods described in scheme E and F or in the experimental part. 2H-Indazoles and 4,5,6,7-tetrahydro-2H-indazoles 2 can be converted into alcohols 4 e.g. via treatment with a strong base such as n-buthyllithium in a solvent like tetrahydrofuran preferably at a temperature between −78° C. and 0° C. and subsequent addition of an aldehyde of formula 3 (step a). Aldehydes 3 are commercially available, described in the literature or can be prepared by methods well known to a person skilled in the art.

Alcohols 4 can be oxidized to ketones 5 applying standard literature procedures, e.g. 2-iodoxybenzoic acid in a mixture of tetrahydrofuran and dimethylsulfoxide, preferably at temperatures between 0° C. and ambient temperature (step b).

Ketones 5 can be transformed into acids of formula II using e.g. the following reaction sequence: i) reaction of ketones 5 with trimethylsilyl cyanide using catalytic amounts of zinc (II) iodide to the corresponding trimethylsilanyloxy-acetonitriles, preferably at temperatures between ambient temperature and 50° C.; ii) subsequent one pot reduction with tin (II) chloride and hydrolysis to acids of formula II in a solvent mixture consisting of concentrated aqueous hydrochloric acid and acetic acid, preferably at the reflux temperature of the solvent mixture employed (step c).

Acids of formula II—after suitable activation—can be coupled with amines of formula III to amides of formula Ic (compounds of formula I, wherein $R^8$ corresponds to —C(O)—NH—$R^9$) using standard peptide coupling procedures described in the literature (step d). Activation of carboxylic acids of formula II can be performed using methods well known to a person skilled in the art. For example, carboxylic acids of formula II can be transformed into carboxylic acid chlorides by solving the acid in dichloromethane and reacting it with $(ClCO)_2$ in DMF at room temperature or by reacting it with neat thionyl chloride at reflux temperature. Alternatively, carboxylic acids of formula II can be in situ activated and transformed into the final products of formula Ic using coupling reagents such as e.g. N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N',N'-tetramethyluronium tetrafluoroborate (TBTU), 1-[bis(dimethylamino)methylene]-1H-1,2,3-triazolo[4,5-b]pyridinium-3-oxide hexafluorophosphate (HATU) or benzotriazol-1-yloxytris(dimethylamino)phosphonium hexafluorophoshate (BOP). Preferably, EDCI, TBTU or BOP are used. The reaction is carried out in the presence of a base such as diisopropylethylamine, triethylamine, N-methylmorpholine, optionally in the presence of 4-dimethylamino-pyridine or HOBt (1-hydroxybenzo-triazole), in solvents such as dichloromethane, DMF, DMA or dioxane at temperatures between 0° C. and ambient temperature.

Amines of formula III are commercially available, described in the literature or can be prepared by methods well known to a person skilled in the art. To introduce residues $R^6 \neq$ hydrogen, carboxylic acids of formula II can e.g. i) be converted into the corresponding carboxylic acid esters applying standard literature methods (e.g. heating acid of formula II with a primary or secondary alcohol in the presence of a catalyst such as sulfuric acid, preferably under reflux conditions); ii) treatment of the obtained ester with a base and an alkylating reagent using methods known to a person skilled in the art (e.g. lithium diisopropylamide as a base and an alkyl halide as alkylating reagent in a solvent such as tetrahydrofuran at temperatures between −78° C. and the reflux temperature of the solvent employed). Optionally, such alkylations can be carried out in an enantioselective or diastereoselective fashion using either alcohols which contain a chiral center in the esterification step and/or a chiral catalyst in the alkylation step; iii) saponification of the ester to form substituted carboxylic acids of formula II (e.g. using aqueous LiOH, NaOH or KOH in tetrahyrofuran/ethanol or another suitable solvent). Acids of formula II with $R^6$=F can e.g. be synthesized via direct fluorination of the corresponding silyl ketene acetal using 1-chloromethyl-4-fluoro-1,4-diazoniabicyclo[2.2.2]octane bis-(tetrafluoroborate) following a procedure described in F. Zhang, J. Z. Song, *Tetrahedron Lett.* 2006, 47, 7641-7644.

Amides of formula Ic can contain carboxylic esters which can be hydrolyzed to the corresponding acids using standard procedures, e.g. by treatment with an alkali hydroxide like LiOH or NaOH in a polar solvent mixture like tetrahydrofuran/ethanol/water or by treatment with hydrochloric acid in dioxane in the case of e.g. tert-butyl esters. Optionally, indazoles or 4,5,6,7-tetrahydroindazoles of formula Ic can contain cyano groups which can be converted to the corresponding tetrazoles using standard procedures, e.g. by treatment with sodium azide in the presence of a lewis acid in water or organic solvents like dichloromethane at temperatures between 0° C. and the boiling point of the solvent.

If one of the starting materials, compounds of formulae 2, 3 or III, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If one or more compounds of formulae 2 to 5, II or III contain chiral centers, indazoles or 4,5,6,7-tetrahydroindazoles of formula Ic can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R) or (S)-1-phenyl-ethylamine, (R) or (S)-1-naphthalen-1-yl-ethylamine, brucine, quinine or quinidine) or by separation of the antipodes by specific chromatographic methods using either a chiral adsorbens or a chiral eluent.

Malonic acid derivatives 6 are commercially available, described in the literature or can be synthesized by methods well known to a person skilled in the art. To facilitate the conversion of malonic acid derivatives 6 into bis-keto esters 9 the acid group of compounds 6 can e.g. be transformed into benzotriazol-1-yl amides 7 (step a). This transformation can e.g. be achieved via i) treatment of acids 6 with thionyl chloride, preferably under reflux conditions to form the corresponding acid chloride (alternative method: carboxylic acid 6, $CH_2Cl_2$, $(ClCO)_2$, DMF, rt); and ii) subsequent reaction with 1,2,3-benzotriazole in the presence of a base such as triethylamine or the like, preferably in a solvent like dichloromethane at temperatures between −20° C. and ambient temperature. Benzotriazoles 7 can than be converted into

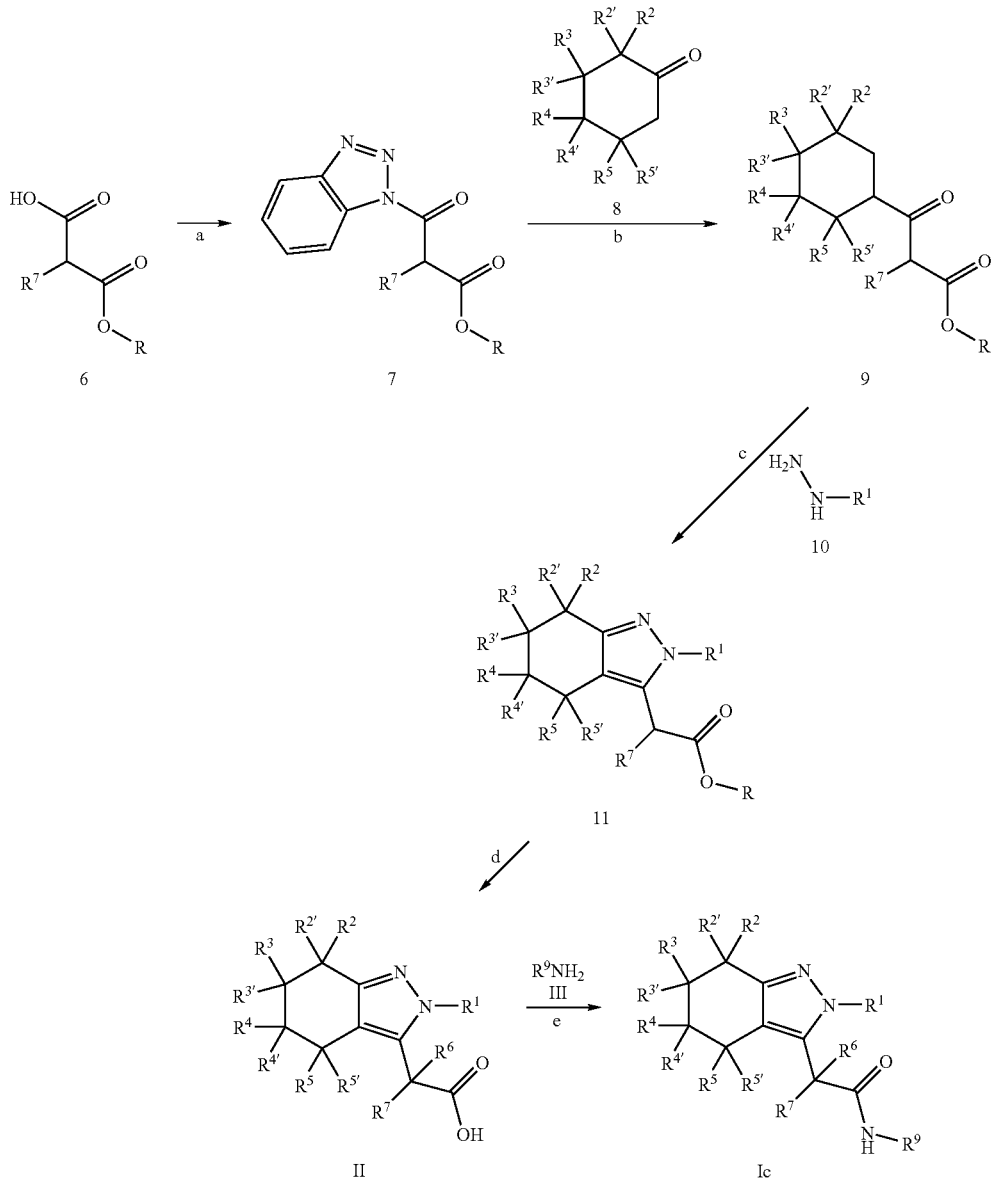

Scheme B

Alternatively, 4,5,6,7-tetrahydro-2H-indazoles of formula Ic can be prepared starting from 2-substituted malonic acid mono esters 6 (R e.g. corresponds to $C_{1-7}$-alkyl, scheme B).

bis-keto esters 9 via reaction with a deprotonated ketone (derived from ketone 8), preferably in a solvent such as tetrahydrofuran or the like (step b). Deprotonation can be achieved using a base such as lithium diisopropylamide in a solvent such as tetrahydrofuran or the like at temperatures between −78° C. and ambient temperature. Ketones 8 are commercially available, described in the literature or can be synthesized by methods well known to a person skilled in the art. Condensation of bis-ketones 9 with (hetero)aromatic hydrazines 10 or a salt e.g. the hydrochloride salt of (hetero) aromatic hydrazines 10 gives 4,5,6,7-tetrahydro-2H-indazole esters 11 (step c). Preferably, such condensations are carried out in a solvent such as ethanol and the like, at the reflux temperature of the solvent employed. (Hetero)aromatic hydrazines 10 or the corresponding (hetero)aromatic hydrazine salts are commercially available, described in the literature or can be synthesized by methods well known to a person skilled in the art. Esters 11 can be saponified to form acids of formula II, using e.g. aqueous LiOH, NaOH or KOH in tetrahydrofuran/ethanol or another suitable solvent at temperatures between 0° C. and the reflux temperature of the solvent employed (step d). Acids of formula II—after suitable activation—can be coupled with amines of formula III to amides of formula Ic using standard peptide coupling procedures described in the literature (step e). Activation of carboxylic acids of formula II can be performed using methods well known to a person skilled in the art. (e.g. carboxylic acid chlorides: 1. carboxylic acid, $CH_2Cl_2$, $(ClCO)_2$, DMF, rt; or 2. carboxylic acid, thionyl chloride, reflux). Alternatively, carboxylic acids of formula II can be in situ activated and transformed into the final products of formula Ic using coupling reagents such as e.g. N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N',N'-tetramethyluronium tetrafluoroborate (TBTU), 1-[bis(dimethylamino)methylene]-1H-1,2,3-triazolo[4,5-b]pyridinium-3-oxide hexafluorophosphate (HATU) or benzotriazol-1-yloxytris(dimethylamino)phosphonium hexafluorophoshate (BOP). Preferably, EDCI, TBTU or BOP are used. The reaction is carried out in the presence of a base such as diisopropylethylamine, triethylamine, N-methylmorpholine, optionally in the presence of 4-dimethylamino-pyridine or HOBt (1-hydroxybenzo-triazole), in solvents such as dichloromethane, DMF, DMA or dioxane at temperatures between 0° C. and ambient temperature. Amines of formula III are commercially available, described in the literature or can be prepared by methods well known to a person skilled in the art.

Amides of formula Ic can contain carboxylic esters which can be hydrolyzed to the corresponding acids using standard procedures, e.g. by treatment with an alkali hydroxide like LiOH or NaOH in a polar solvent mixture like tetrahydrofuran/ethanol/water or by treatment with hydrochloric acid in dioxane in the case of e.g. tert-butyl esters. Optionally, 4,5,6, 7-tetrahydroindazoles of formula Ic can contain cyano groups which can be converted to the corresponding tetrazoles using standard procedures, e.g. by treatment with sodium azide in the presence of a lewis acid in water or organic solvents like dichloromethane at temperatures between 0° C. and the boiling point of the solvent.

If one of the starting materials, compounds of formulae 6, 8, 10 or III, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If one or more compounds of the formulae 6 to 11, II or III contain chiral centers, 4,5,6,7-tetrahydroindazoles of formula Ic can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R) or (S)-1-phenyl-ethylamine, (R) or (S)-1-naphthalen-1-yl-ethylamine, brucine, quinine or quinidine) or by separation of the antipodes by specific chromatographic methods using either a chiral adsorbens or a chiral eluent.

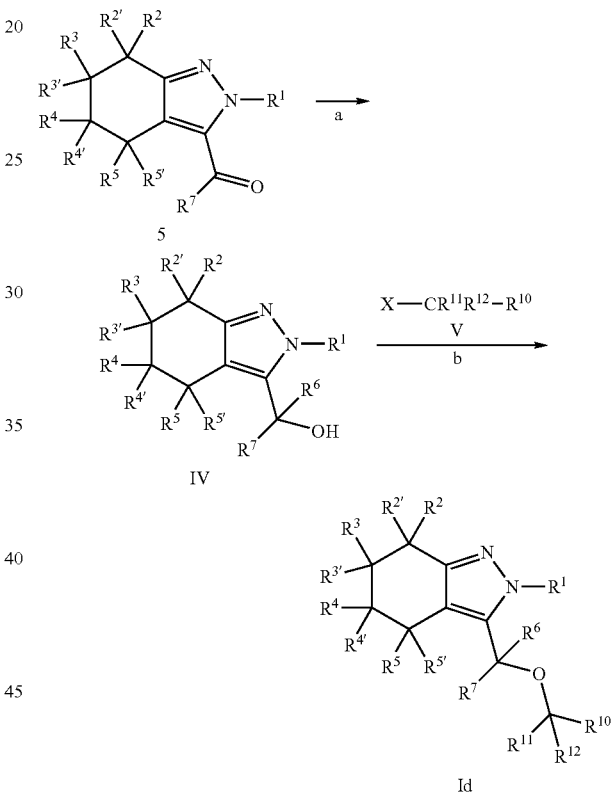

Scheme C

2H-Indazole and 4,5,6,7-tetrahydro-2H-indazole ethers of formula Id (compounds of formula I wherein $R^8$ is —O—$CR^{11}R^{12}R^{10}$) can be prepared starting from ketones 5 (scheme C). Ketones 5 can be converted into alcohols of formula IV (for $R^6$=H equal to compounds 4 in scheme A) applying standard methods described in the literature (step a). Treatment of ketones 5 with an alkyllithium reagent $R^6$Li in solvents like ether or tetrahydrofuran gives tertiary alcohols of formula IV (step a); treatment of ketones 5 with lithium aluminium hydride in solvents like tetrahydrofuran or diethyl ether or with sodium borohydride in solvents like ethanol or methanol, preferably at temperatures between −15° C. and 40° C., gives alcohols of formula IV with $R^6$=H (step a). The alcohol compounds of formula IV which contain a chiral center can optionally be separated into optically pure antipodes by methods well known in the art, e.g. chromatography on a chiral HPLC column, or by derivatization with an optically pure acid to form esters, which can be separated by conventional HPLC chromatography and can then be converted back to the enantiomerically pure alcohols of formula IV. Alternatively, the reduction of ketones 5 to the corresponding secondary alcohols of formula IV can also be carried out in an enantioselective fashion leading to the (R)- or (S)-alcohols of formula IV, e.g. by treatment with borane-dimethylsulfide complex and (S)- or (R)-2-methyl-CBS-oxazaborolidine ((S)- or (R)-1-methyl, 3,3-diphenyl-tetrahydro-pyrrolo(1,2-c)(1,3,2)oxazaborole) as chiral catalyst in tetrahydrofuran, preferably at temperatures between −78° C. and ambient temperature, according to Corey et al. (E. J. Corey, R. K. Bakshi, S. Shibata, *J. Am. Chem. Soc.* 1987, 109, 5551-5553), or by treatment with (+)- or (−)-B-chlorodiisopinocampheyl-borane (DIP-Cl), according to Brown et al. (P. V. Ramachandran, B. Gong, A. V. Teodorovic, H. C. Brown, *Tetrahedron: Asymmetry* 1994, 5, 1061-1074).

Alcohols of formula IV are condensed with compounds of formula V according to well known procedures. If X represents a halide, mesylate or tosylate moiety, alcohols of formula IV can be reacted with compounds of formula V in solvents like N,N-dimethylformamide, acetonitrile, acetone or methyl-ethyl ketone in the presence of a weak base like cesium or potassium carbonate at a temperature ranging from room temperature to 140° C., preferably around 50° C., to yield ether compounds of formula Id (step b).

Ethers of formula Id can contain carboxylic esters which can be hydrolyzed to the corresponding acids using standard procedures, e.g. by treatment with an alkali hydroxide like LiOH or NaOH in a polar solvent mixture like tetrahydrofuran/ethanol/water or by treatment with hydrochloric acid in dioxane e.g. in the case of tert-butyl esters. Optionally, indazoles or 4,5,6,7-tetrahydroindazoles of formula Id can also contain cyano groups which can be converted to the corresponding tetrazoles using standard procedures, e.g. by treatment with sodium azide in the presence of a Lewis acid in water or organic solvents like dichloromethane at temperatures between 0° C. and the boiling point of the solvent.

If one of the starting materials, compounds of formulae 5 or V, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, 2$^{nd}$ Ed., 1991, Wiley N.Y.) can be introduced before the critical step applying methods well known in the art. Such protecting groups can be removed at a later stage of the synthesis using standard methods described in the literature.

If compounds of formulae 5, IV or V contain chiral centers, indazoles or 4,5,6,7-tetrahydroindazoles of formula Id can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenyl-ethylamine, (R)- or (S)-1-naphthalen-1-yl-ethylamine, brucine, quinine or quinidine) or by separation of the antipodes by specific chromatographic methods using either a chiral adsorbens or a chiral eluent.

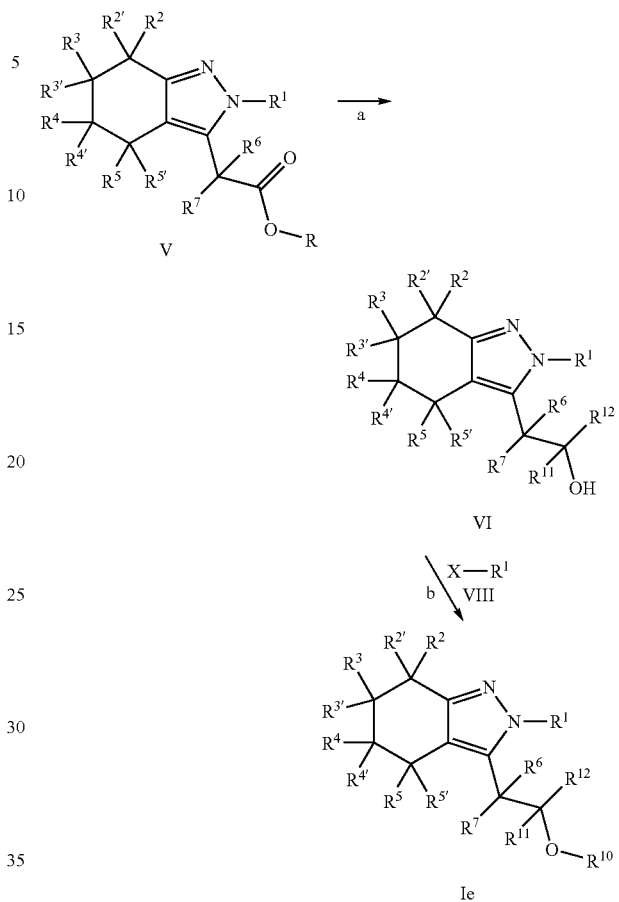

2H-Indazole and 4,5,6,7-tetrahydro-2H-indazole ethers of formula Ie (compounds of formula I wherein $R^8$ is —$CR^{11}R^{12}$—$OR^{10}$ can be prepared starting from acids of formula VI (R═H, compounds of formula II in schemes A and B) or esters of formula VI (R e.g. corresponds to $C_{1-7}$-alkyl, compounds 11 in scheme B). Acids of formula VI (R═H) can be converted into esters (R e.g. equal to $C_{1-7}$-alkyl) applying standard literature procedures, e.g. heating acid of formula VI (R═H) with a primary or secondary alcohol in the presence of a catalyst such as sulfuric acid, preferably under reflux conditions. Acids of formula VI (R═H) can be further transformed into primary alcohols of formula VII ($R^{11}$═H, $R^{12}$═H), e.g. by using diborane in tetrahydrofuran (step a). Esters of formula VI (R e.g. equal to $C_{1-7}$-alkyl) can be reduced, e.g. with lithium aluminum hydride in solvents like ether or tetrahydrofuran, to alcohols of formula VII with $R^{11}$═$R^{12}$═H (step a). Alternatively, substituents $R^{11}$ and/or $R^{12}$ different from hydrogen can be introduced to acids of formula VI (R═H) by i) treatment with $R^{11}$Li optionally in the presence of a Cu (I) salt in ether or tetrahydrofuran to yield the alkyl ketones —$COR^{11}$; ii) subsequent reaction with $R^{12}$Li or lithium aluminium hydride in ether or tetrahydrofuran (step a). The alcohol compounds of formula VII which contain a chiral center can optionally be separated into optically pure antipodes by methods well known in the art, e.g. chromatography on a chiral HPLC column, or by derivatization with an optically pure acid to form esters, which can be separated by conventional HPLC chromatography and can then be converted back to the enantiomerically pure alcohols of formula VII. The reduction of alkyl ketones COR¹¹ to the corresponding secondary alcohols of formula VII of scheme D can also be carried out in an enantioselective fashion leading to the (R)- or (S)-alcohols of formula VII, e.g. by treatment with borane-dimethylsulfide complex and (S)- or (R)-2-methyl-CBS-oxazaborolidine as chiral catalyst in tetrahydrofuran, preferably at temperatures between −78° C. and ambient temperature, according to Corey et al. (E. J. Corey, R. K. Bakshi, S. Shibata, *J. Am. Chem. Soc.* 1987, 109, 5551-5553), or by treatment with (+)- or (−)-B-chlorodiisopinocampheyl-borane (DIP-Cl), according to Brown et al. (P. V. Ramachandran, B. Gong, A. V. Teodorovic, H. C. Brown, *Tetrahedron: Asymmetry* 1994, 5, 1061-1074).

Alcohols of formula VII are condensed with compounds of formula VIII according to well known procedures: if X represents a hydroxy group and R¹⁰ is an aryl system e.g. via Mitsunobu-reaction, with triphenylphosphine and di-tert-butyl-, diisopropyl- or diethyl-azodicarboxylate as reagents, or by using tributylphosphine and N,N,N',N'-tetramethyl azodicarboxamide; this transformation is preferably carried out in a solvent like toluene, dichloromethane or tetrahydrofuran at ambient temperature (step b). Alternatively, if X represents a halide, mesylate or tosylate moiety, alcohols of formula VII can be reacted with compounds VIII (R¹⁰ not equal to an aryl system) in solvents like N,N-dimethylformamide, acetonitrile, acetone or methyl-ethyl ketone in the presence of a weak base like cesium or potassium carbonate at a temperature ranging from room temperature to 140° C., preferably around 50° C., to yield ether compounds Ie (step b).

Ethers of formula Ie can contain carboxylic esters which can be hydrolyzed to the corresponding acids using standard procedures, e.g. by treatment with an alkali hydroxide like LiOH or NaOH in a polar solvent mixture like tetrahydrofuran/ethanol/water or by treatment with hydrochloric acid in dioxane e.g. in the case of tert-butyl esters. Optionally, indazoles or 4,5,6,7-tetrahydroindazoles of formula Ie can contain cyano groups which can be converted to the corresponding tetrazoles using standard procedures, e.g. by treatment with sodium azide in the presence of a lewis acid in water or organic solvents like dichloromethane at temperatures between 0° C. and the boiling point of the solvent.

If one of the starting materials, compounds of formulae VI or VIII, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, 2nd Ed., 1991, Wiley N.Y.) can be introduced before the critical step applying methods well known in the art. Such protecting groups can be removed at a later stage of the synthesis using standard methods described in the literature.

If compounds of formulae VI, VII and VIII contain chiral centers, indazoles or 4,5,6,7-tetrahydroindazoles of formula Ie can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenyl-ethylamine, (R)- or (S)-1-naphthalen-1-yl-ethylamine, brucine, quinine or quinidine) or by separation of the antipodes by specific chromatographic methods using either a chiral adsorbens or a chiral eluent.

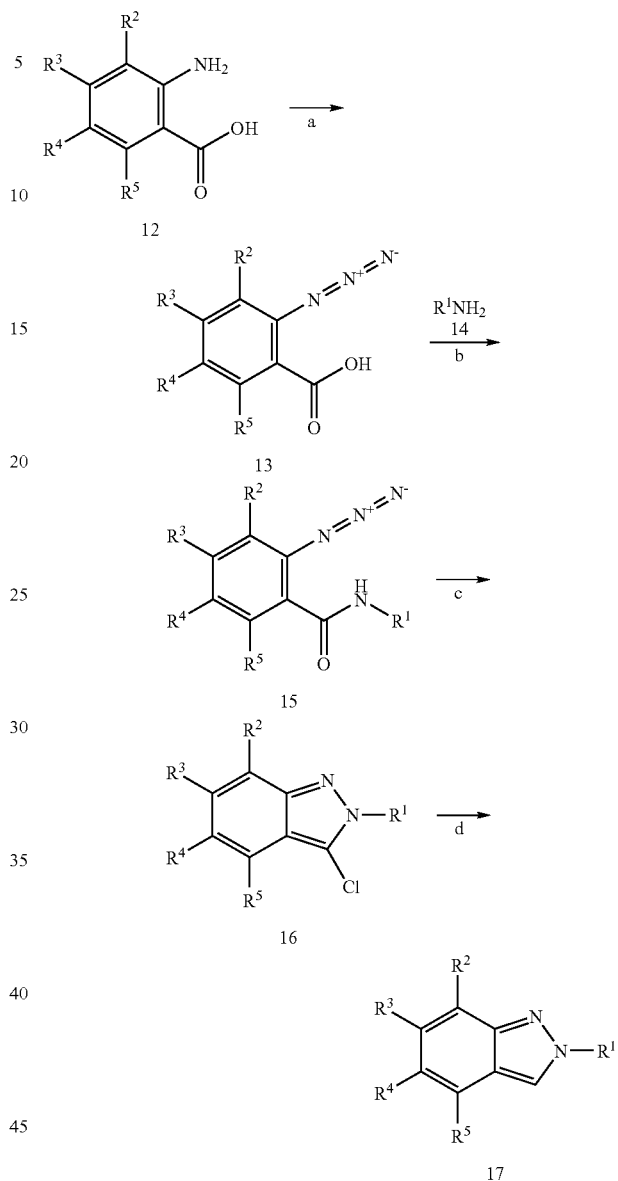

2-Substituted 2H-indazoles 16 and 17 (corresponding to compounds 2 in scheme A) can be prepared starting from 2-amino-benzoic acids 12 as described in scheme E. 2-Amino-benzoic acids 12 are commercially available, described in the literature or can be synthesized by methods well known to a person skilled in the art. Transformation of amino acids 12 into 2-azido-benzoic acids 13 can e.g. be achieved via treatment of amines 12 with an aqueous solution of sodium azide preferably at temperatures between −10° C. and ambient temperature (step a). Acids 13 can be condensed—after suitable activation—with amines 14 to amides 15 using standard methods described in the literature (step b). Amines 14 are either commercially available, described in the literature or can be prepared by methods well known to a person skilled in the art. If acid 13 is activated as a carboxylic acid chloride, bromide or carboxylic anhydride the reaction can be performed in a solvent such as dichloromethane, optionally in the presence of a base such as triethylamine, ethyl-diisopropyl-amine or N-ethylmorpholine at temperatures between 0° C. and ambient temperature. Carboxylic acid chlorides can be prepared by methods well known to a person skilled in the art. (e.g. 1. carboxylic acid, CH$_2$Cl$_2$, (ClCO)$_2$, DMF, ambient temperature; or 2. carboxylic acid, thionyl chloride, reflux). Alternatively, carboxylic acids 13 can be in situ activated and transformed into amides 15 using e.g. N-(3-dimethylaminopropyl)-N'-ethyl-carbodiimide-hydrochloride, TBTU (0-(benzotriazol-1-yl)-N,N,N',N'-tetramethyluronium tetrafluoroborate) or BOP (benzotriazol-1-yloxytris(dimethylamino)phosphonium hexafluorophoshate) in the presence of a base such as ethyl-diisopropyl-amine, triethylamine, N-methylmorpholine optionally in the presence of 4-dimethylamino-pyridine or HOBt (1-hydroxybenzo-triazole) in solvents such as dichloromethane, N,N-dimethylformamide, N,N-dimethylacetamide or dioxane preferably at temperatures between 0° C. and ambient temperature. 2-Azido-amides 15 can be cyclised to 2-substituted 3-chloro-2H-indazoles 16 by boiling them in thionyl chloride (step c). Treatment of 3-chloro-2H-indazoles 16 with zinc powder in the presence of an acid like acetic acid, preferably at the reflux temperature of the acid employed, provides 2-substituted 2H-indazoles 17 (step d).

If one of the starting materials, compounds of formulae 12 or 14, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, 2$^{nd}$ Ed., 1991, Wiley N.Y.) can be introduced before the critical step applying methods well known in the art. Such protecting groups can be removed at a later stage of the synthesis using standard methods described in the literature.

If compounds 12 or 14 contain chiral centers, 2-substituted 2H-indazoles 16 and 17 can be obtained as mixtures of diastereomers or enantiomers, which can be separated by methods well known in the art, e.g. (chiral) HPLC or crystallization. Racemic compounds can e.g. be separated into their antipodes by specific chromatographic methods using either a chiral adsorbens or a chiral eluent.

Scheme F

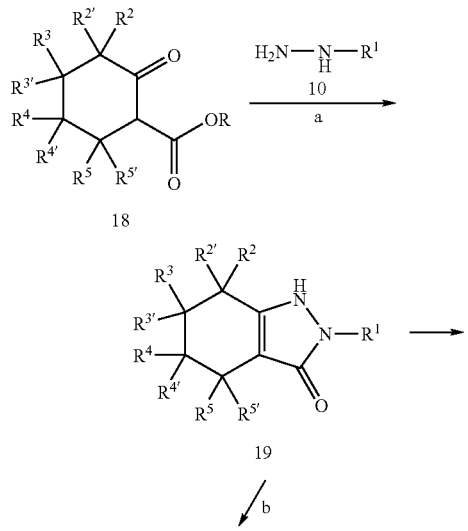

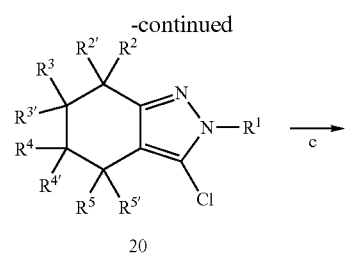

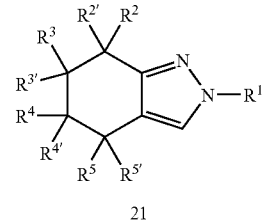

2-Substituted 4,5,6,7-tetrahydro-2H-indazoles 20 and 21 (corresponding to compounds 2 in scheme A) can be prepared starting from cyclohexanone-2-carboxylic acid esters 18 (R is e.g. C$_{1-7}$-alkyl) as described in scheme F. Cyclohexanone-2-carboxylic acid esters 18 are commercially available, described in the literature or can be synthesized by methods well known to a person skilled in the art. Condensation of keto esters 18 with (hetero)aromatic hydrazines 10 or a salt e.g. the hydrochloride salt of (hetero)aromatic hydrazines 10 gives 2-substituted 1,2,4,5,6,7-hexahydro-indazol-3-ones 19 (step a). Preferably, such condensations are carried out in a solvent such as toluene and the like, at the reflux temperature of the solvent employed. (Hetero)aromatic hydrazines 10 or the corresponding (hetero)aromatic hydrazine salts are commercially available, described in the literature or can be synthesized by methods well known to a person skilled in the art. 1,2,4,5,6,7-Hexahydro-indazol-3-ones 19 can be converted to 2-substituted 3-chloro-4,5,6,7-tetrahydro-2H-indazoles 20 e.g. by treatment with phosphorus oxychloride in the presence of catalytic amounts of N,N-dimethyl-anilin, preferably under reflux conditions (step b). Transformation of 3-chloro-4,5,6,7-tetrahydro-2H-indazoles 20 into 2-substituted 4,5,6,7-tetrahydro-2H-indazoles 21 can e.g. be achieved using hydrogen gas in the presence of a transition metal catalyst like palladium on charcoal (step c).

If one of the starting materials, compounds of formulae 18 or 10, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, 2$^{nd}$ Ed., 1991, Wiley N.Y.) can be introduced before the critical step applying methods well known in the art. Such protecting groups can be removed at a later stage of the synthesis using standard methods described in the literature.

If compounds 18, 10 or 19 contain chiral centers, 2-substituted 4,5,6,7-tetrahydro-2H-indazoles 20 and 21 can be obtained as mixtures of diastereomers or enantiomers, which can be separated by methods well known in the art, e.g. (chiral) HPLC or crystallization. Racemic compounds can e.g. be separated into their antipodes by specific chromatographic methods using either a chiral adsorbens or a chiral eluent.

Compounds of general structure If to Ii can be prepared according to Scheme G from intermediates of type 22. Intermediates 22 can be prepared in the case LG signifies a —OSO$_2$alkyl, —OSO$_2$-fluoroalkyl or —OSO$_2$aryl group by treatment of alcohol VII (Scheme D) with, e.g. an alkyl-, fluoroalkyl- or arylsulfonic acid chloride or anhydride in a suitable solvent such as, e.g. dichloromethane and using an appropriate base such as, e.g. Hünig's base or pyridine (step a). Reaction of intermediates 22 with, e.g. optionally substituted alkyl- or aryl-thiols 23 with a suitable base such as, e.g. sodium hydride in an appropriate solvent such as, e.g. N,N-dimethylformamide furnishes compounds If (step b). Compounds If can be converted into compounds Ig through oxidation of the sulfur atom with an oxidizing agent such as, e.g. 3-chloroperoxybenzoic acid in a suitable solvent such as, e.g. dichloromethane (step c). In case compounds If and Ig carry a carboxylic ester group these can be cleaved by methods known to those skilled in the art and as described for example in "Protective Groups in Organic Chemistry" by T. W. Greene and P. G. M. Wutts, 2nd Ed., 1991, Wiley N.Y.) to yield the corresponding carboxylic acids. For example, a benzyl ester can be cleaved by catalytic hydrogenation using an appropriate catalyst such as, e.g. palladium on charcoal in a suitable solvent such as, e.g. methanol, ethanol, ethyl acetate, tetrahydrofuran or mixtures of said solvents. An alkyl ester such as, e.g. a methyl or ethyl ester can be cleaved under basic conditions (e.g. with lithium or sodium hydroxide in polar solvents such as, e.g. methanol, water or tetrahydrofuran or mixtures of said solvents). A tert-butyl ester can be cleaved for example under acidic conditions (e.g. using trifluoroacetic acid, optionally in an appropriate solvent such as, e.g. dichloromethane and optionally using a nucleophilic scavenger such as, e.g. 1,3-dimethoxybenzene or thioanisole, or using concentrated hydrochloric acid in tetrahydrofuran or formic acid in an appropriate solvent such as an alcohol like, e.g. isopropanol). An allyl ester can be cleaved for example in a transition metal-catalyzed reaction using, e.g. tetrakis(triphenylphenyl)palladium as catalyst together with pyrrolidine or morpholine in tetrahydrofuran as solvent.

Optionally, compounds If and Ig can also contain cyano groups which can be either hydrolyzed to the carboxylic acid under basic (e.g. with aqueous sodium or lithium hydroxide) or acidic conditions (e.g. hydrochloric or sulphuric acid) or can be converted to the corresponding tetrazoles using standard procedures such as, e.g. by treatment with sodium azide in the presence of a Lewis acid or ammonium chloride in water or organic solvents like dichloromethane or N,N-dimethylformamide at temperatures between 0° C. and the boiling point of the solvent to furnish compounds Ih and Ii (step d).

Alternatively, compounds of the formula Ii can be synthesized by oxidation of compounds Ih (step c) applying the methods described above.

If one of the starting materials, compounds of formulae VII or 23, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, 2$^{nd}$ Ed., 1991, Wiley N.Y.) can be introduced before the critical step applying methods well known in the art. Such protecting groups can be removed at a later stage of the synthesis using standard methods described in the literature.

If compounds of formulae VII and 23 contain chiral centers, indazoles or 4,5,6,7-tetrahydroindazoles of formula If, Ig, Ih and Ii can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenyl-ethylamine, (R)- or (S)-1-naphthalen-1-yl-ethylamine, brucine, quinine or quinidine) or by separation of the antipodes by specific chromatographic methods using either a chiral adsorbens or a chiral eluent.

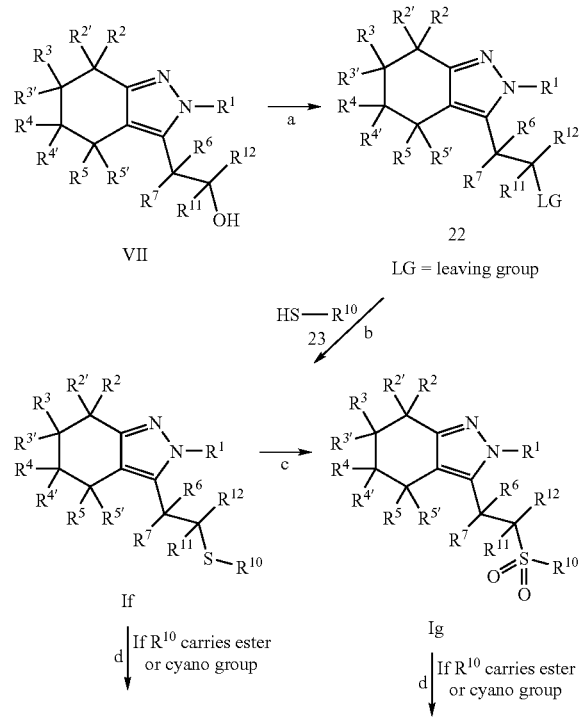

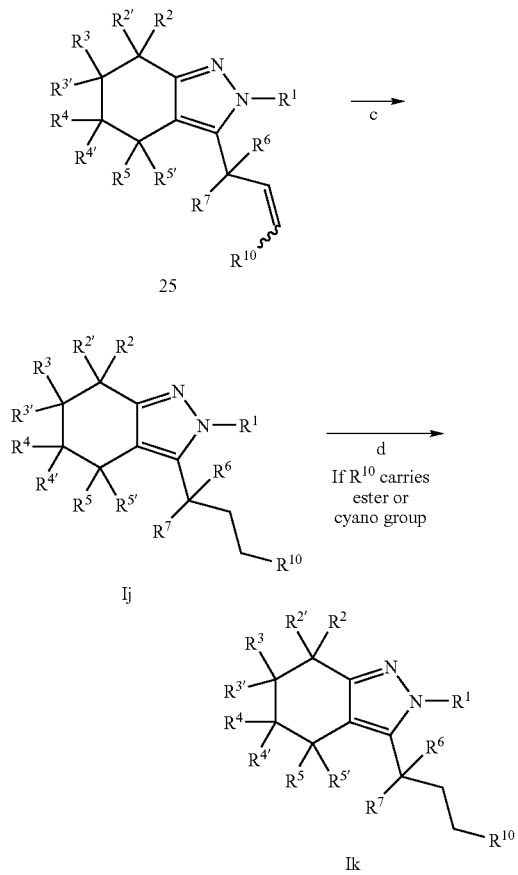

Ij

Ik

Compounds of general structure Ij and Ik in which $R^{11}=R^{12}=H$ can be prepared according to Scheme H. Aldehydes 24 can be synthesized by oxidation of intermediates VII (step a). Reactions of this type are known to those skilled in the art and are widely used and described in the literature (e.g. "March's Advanced Organic Chemistry" by M. B. Smith and J. March, $7^{th}$ ed., 2007, Wiley & Sons N.Y.). For example, intermediate VII can be oxidized with, e.g. 1,1,1-triacetoxy-1,1-dihydro-1,2-benziodoxol-3(1H)-one in an appropriate solvent such as, e.g. dichloromethane or chloroform. Intermediates 25 are accessible by, e.g. Wittig reaction which is well known to those skilled in the art. For example, intermediate 24 is reacted with an optionally substituted benzyl-triphenyl-phosphonium chloride or bromide (either commercially available or synthesized by methods known in the art) in the presence of a suitable base and a solvent such as, e.g. potassium tert-butylate, butyllithium or sodium hydride in, e.g. tetrahydrofuran (step b). Depending on the reaction conditions intermediates 25 can exists as cis, trans or mixture of cis/trans isomers. Intermediates 25 can be transformed into compounds Ij by, e.g. catalytic hydrogenation using a transition metal catalyst such as, e.g. palladium or platinum on charcoal in an appropriate solvent such as, e.g. ethyl acetate, methanol or ethanol or mixtures of said solvents (step c).

Optionally compounds Ij can contain ester or cyano groups that can be converted into the corresponding carboxylic acid and tetrazole groups, respectively, applying the conditions described before, to furnish compounds Ik (step d).

If one of the starting materials, compounds of formulae VII or the substituted benzyl-triphenyl-phosphonium chloride or bromide, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds of formulae VII and the substituted benzyl-triphenyl-phosphonium chlorides or bromides contain chiral centers, indazoles or 4,5,6,7-tetrahydroindazoles of formula Ij and Ik can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenyl-ethylamine, (R)- or (S)-1-naphthalen-1-yl-ethylamine, brucine, quinine or quinidine) or by separation of the antipodes by specific chromatographic methods using either a chiral adsorbens or a chiral eluent.

Scheme I

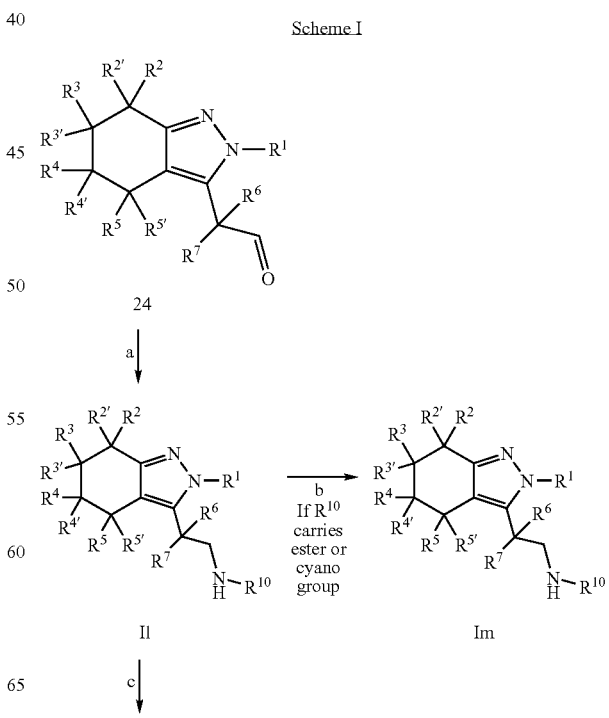

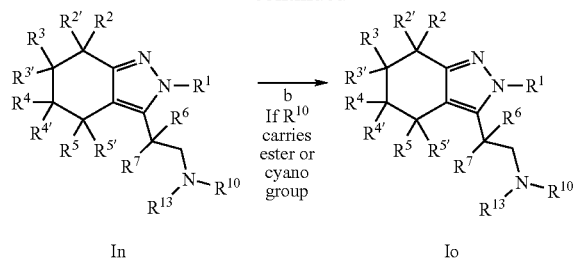

Compounds of the general formula Il-Io in which $R^{11}=R^{12}=H$ can be prepared as described in Scheme I. Intermediates 24 (prepared as described in Scheme H) are reacted with an alkyl- or optionally substituted arylamine in the presence of a reducing agent such as, e.g. cyanoborohydride, sodium triacetoxyborohydride or di-n-butyltin dichloride with triphenysilane in an appropriate solvent such as, e.g. tetrahydrofuran to furnish compounds Il (step a). In those cases where compounds Il contain ester or cyano groups, these can be converted into the corresponding carboxylic acid and tetrazole groups (step b), respectively, applying the conditions described above. Compounds In can be prepared by alkylation of compounds Il for example with $R^{13}LG$ (LG signifies a leaving group such as, e.g. chloro, bromo, $OSO_2$alkyl, $OSO_2$fluoroalkyl or $OSO_2$aryl, $R^{13}$ is as defined above) in appropriate solvents such as, e.g. N,N'-dimethylformamide and using a suitable base such as, e.g. cesium carbonate or sodium hydride. Alternatively, compounds In can be synthesized from compounds Il via reductive amination using aldehydes of the type $R^{13}CHO$ and applying conditions as described above. If compounds Il and In carry an ester or cyano group they can be converted into the corresponding carboxylic acid and tetrazole groups, respectively, applying the conditions described above. If one of the starting materials, compounds of formulae 24, the alkyl- or optionally substituted arylamine or $R^{13}LG$, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds of formulae 24, the alkyl- or optionally substituted arylamine and $R^{13}LG$ contain chiral centers, indazoles or 4,5,6,7-tetrahydroindazoles of formula Il, Im, In and Io can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenyl-ethylamine, (R)- or (S)-1-naphthalen-1-yl-ethylamine, brucine, quinine or quinidine) or by separation of the antipodes by specific chromatographic methods using either a chiral adsorbens or a chiral eluent.

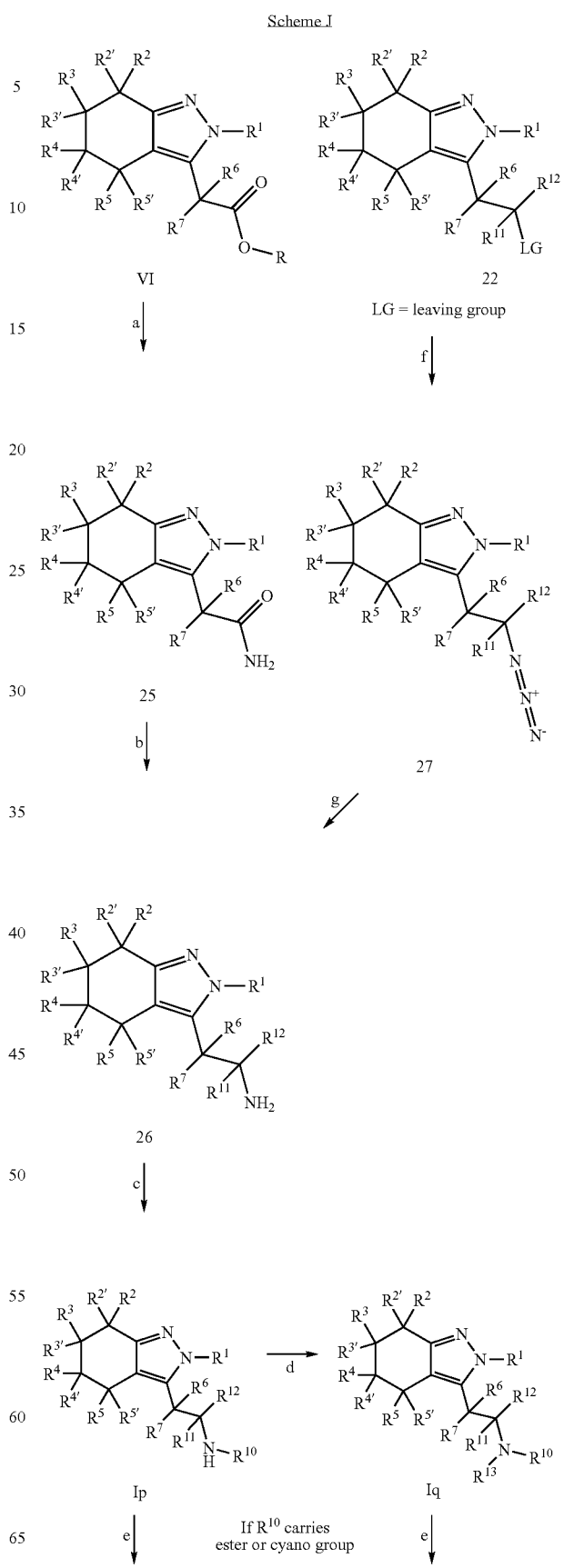

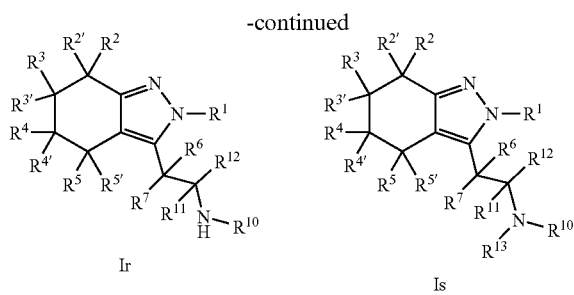

Alternatively, compounds Ip-Is can be prepared according to Scheme J. Carboxylic acids VI (R═H, see Scheme D) can be transformed into intermediates 25 by, e.g. treating the acid group in VI with an activating agent such as, e.g. N-hydroxybenzotriazole monohydrate, optionally together with 1-ethyl-3-(3-dimethyllaminopropyl)carbodiimide hydrochloride, in the presence of a base such as, e.g. ethyl diisopropylamine in a suitable solvent such as, e.g. N,N-dimethylformamide and an ammonia source such as, e.g. ammonium chloride (step a). The amide group in intermediates 25 can be converted to the corresponding amine by, e.g. treatment with a reducing agent such as, e.g. lithium aluminium hydride in a suitable solvent such as, e.g. tetrahydrofuran to give intermediate 26 with $R^{11}$═$R^{12}$═H (step b). Intermediates 26 with $R^{11}$ and $R^{12}$ as defined above can be alternatively obtained from intermediates 22 (prepared as described in Scheme G) by converting them to the azide (intermediate 27, step f) by, e.g. reaction with sodium azide in a suitable solvent such as, e.g. N,N-dimethylformamide and reduction of the azide to the amine (step g) by, e.g. catalytic hydrogenation applying the same methods as described above. Intermediates 26 can be transformed into compounds of formula Ip though alkylation or reductive amination according to the methods described before (step c). Compounds Ip can be further converted into compounds Iq through alkylation or reductive amination applying the methods described before (step d). In case compounds Ip and Iq contain ester or cyano groups they can be converted to the corresponding carboxylic acid and tetrazole groups, respectively, applying the conditions described before, to furnish compounds Ir and Is (step e) wherein $R^{10}$ signifies a carboxylic acid or tetrazole group.

If one of the starting materials, compounds of formulae VI, 22 or the alkylating reagents, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds of formulae VI, 22 or the alkylating reagents contain chiral centers, indazoles or 4,5,6,7-tetrahydroindazoles of formula Ip, Iq, Ir and Is can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenylethylamine, (R)- or (S)-1-naphthalen-1-yl-ethylamine, brucine, quinine or quinidine) or by separation of the antipodes by specific chromatographic methods using either a chiral adsorbens or a chiral eluent.

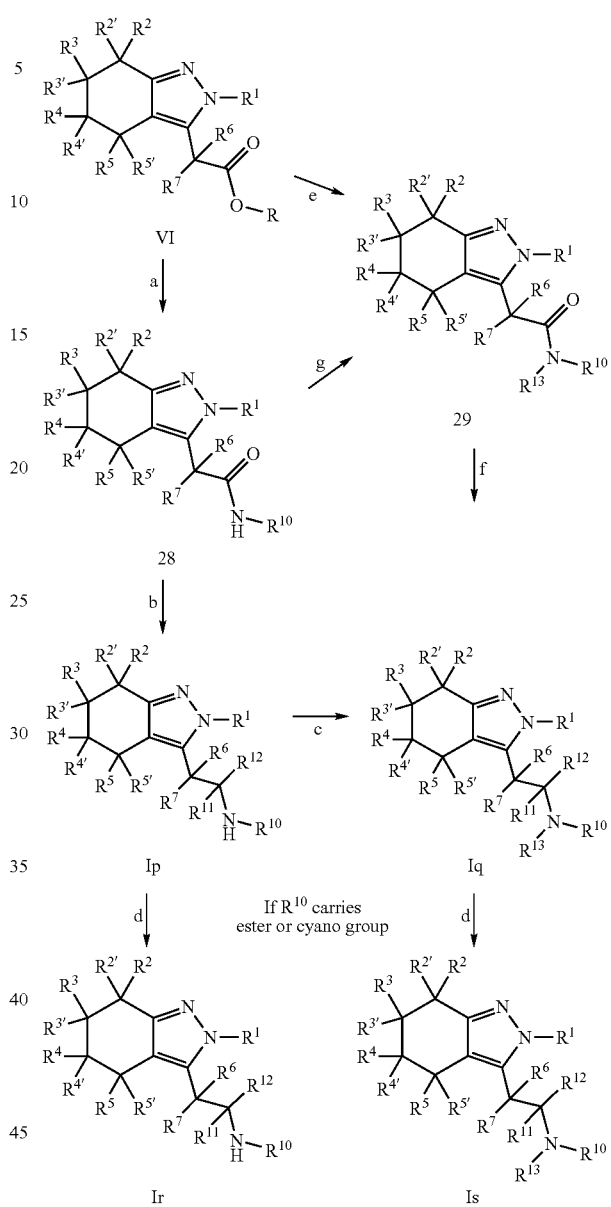

Scheme K

Compounds Ip-Is can also be prepared according to Scheme K if substituents $R^1$ to $R^{13}$ are stable under the reducing conditions applied in steps b and f. Amide coupling of intermediates VI (R═H) with optionally substituted amines $R^{10}NH_2$ or $R^{10}R^{13}NH$ (either commercially available or accessible by methods described in references or by methods known in the art) gives compounds 28 (step a) or 29 (step e). Amide couplings of this type are widely described in the literature (e.g. Comprehensive Organic Transformations: A Guide to Functional Group Preparations, 2nd Edition, Richard C. Larock, John Wiley & Sons, New York, N.Y. 1999) and can be accomplished by employing the usage of coupling reagents such as, e.g. N,N-carbonyldiimidazole (CDI), 1-hydroxy-1,2,3-benzotriazole (HOBT) or O-benzotriazol-1-yl-N,N,N,N-tetramethyluronium tetrafluoroborate (TBTU) in a suitable solvent like, e.g. N,N-dimethylformamide (DMF) or dioxane, optionally in the presence of a base (e.g. triethylamine, diisopropylethylamine or 4-(dimethylamino)pyridine). Alternatively, intermediates 28 and 29 can be obtained by converting intermediates VI (R═H) into the corresponding acid chlorides by treatment with, e.g. thionyl chloride, optionally in a solvent such as, e.g. dichloromethane and reaction of the acid chloride with optionally substituted cycloalkyl/(hetero)aryl amines in an appropriate solvent such as, e.g. dichloromethane and a base such as, e.g. triethylamine, pyridine diisopropylethylamine or 4-(dimethylamino)pyridine. Intermediates 29 can also be obtained by alkylation of intermediates 28 (step g) by the methods described before. Conversion of intermediates 28 into compounds Ip with $R^{11}$═$R^{12}$═H (step b) and of intermediates 29 into compounds Iq with $R^{11}$═$R^{12}$═H (step f) can be accomplished for example by treating intermediates 28 or 29 with a suitable reducing agent such as, e.g. lithium aluminium hydride, di-isobutylaluminium hydride or borane dimethyl sulfide or tetrahydrofuran complex in a suitable solvent such as, e.g. diethyl ether, tert-butyl methyl ether or tetrahydrofuran at temperatures between 0° C. and the boiling point of the solvent. Conversion of compounds Ip into Iq (step c) and compounds Ip and Iq into compounds Ir and Is, respectively, wherein $R^{10}$ signifies a carboxylic acid of tetrazole group (step d) can be accomplished according to the methods described above.

If one of the starting materials, compounds of formulae VI, amines $R^{10}NH_2$ or $R^{10}R^{13}NH$, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds of formulae VI, amines $R^{10}NH_2$ or $R^{10}R^{13}NH$, contain chiral centers, indazoles or 4,5,6,7-tetrahydroindazoles of formula Ip, Iq, Ir and Is can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization e.g. with optically pure amines (such as e.g. (R)- or (S)-1-phenyl-ethylamine, (R)- or (S)-1-naphthalen-1-yl-ethylamine, brucine, quinine or quinidine) or by separation of the antipodes by specific chromatographic methods using either a chiral adsorbens or a chiral eluent.

If desired or required functional groups present in compound of formula I (such as —$CO_2$alkyl, amino groups, cyano groups and others) may be derivatized to other functional groups using typical standard procedures known to those skilled in the art (e.g. reduction of —$CO_2$alkyl to —$CH_2OH$ with $LiAlH_4$, hydrolysis of —$CO_2$alkyl to —$CO_2H$ and subsequent optional conversion to an amide, acylation of amino groups).

As described above, the novel compounds of the present invention have been found to bind to and selectively activate FXR. They can therefore be used in the treatment or prophylaxis of diseases and conditions that are affected by FXR modulators. Preferably, the FXR modulators are FXR agonists.

"Diseases which are affected by FXR modulators" include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease. Preferred diseases (and conditions) which are affected by FXR modulators are prevention or treatment of high LDL cholesterol levels, high triglycerides, dyslipidemia, cholesterol gallstone disease, cancer, non-insulin dependent diabetes mellitus and metabolic syndrome. Particularly preferred diseases which are affected by FXR modulators are high LDL cholesterol, high triglyceride levels and dyslipidemia.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment or prophylaxis of diseases which are affected by FXR modulators, particularly as therapeutically active substances for the treatment or prophylaxis of increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease.

In another preferred embodiment, the invention relates to a method for the therapeutic or prophylactic treatment of diseases which are affected by FXR modulators, particularly for the therapeutic or prophylactic treatment of increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease, which method comprises administering a compound as defined above to a human being or animal.

The invention also embraces the use of compounds as defined above for the therapeutic or prophylactic treatment of diseases which are affected by FXR modulators, particularly for the therapeutic or prophylactic treatment of increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease.

The invention also relates to the use of compounds as described above for the preparation of medicaments for the therapeutic or prophylactic treatment of diseases which are affected by FXR modulators, particularly for the therapeutic or prophylactic treatment of increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease. Such medicaments comprise a compound as described above.

Also contemplated herein is a combination therapy using one or more compounds of formula I or compositions provided herein, or a pharmaceutically acceptable derivative thereof, in combination with one or more compounds selected from the group consisting of the following: cholesterol biosynthesis inhibitors (HMG CoA reductase inhibitors, e.g. lovastatin, simvastatin, pravastatin, fluvastatin, atorvastatin, cerivastatin, nisvastatin and rivastatin); squalene epoxidase inhibitors (e.g. terbinafine); plasma HDL-raising agents (e.g. CETP inhibitors e.g. anacetrapib, R1658); human peroxisome proliferator activated receptor (PPAR) gamma agonists (e.g. thiazolidinediones e.g. rosiglitazone, troglitazone, and pioglitazone); PPAR alpha agonists (e.g. clofibrate, fenofibrate and gemfibronzil); PPAR dual alpha/gamma agonists (e.g. muraglitazar, aleglitazar, peliglitazar); bile acid sequestrants (e.g. anion exchange resins, or quaternary amines (e.g. cholestyramine or colestipol)); bile acid transport inhibitors (BATi); nicotinic acid, niacinamide; cholesterol absorption inhibitors (e.g. ezetimibe); acyl-Coenzyme A:cholesterol O-acyl transferase (ACAT) inhibitors (e.g. avasimibe); selective estrogen receptor modulators (e.g. raloxifene or tamoxifen); LXR alpha or beta agonists, antagonists or partial agonists (e.g. 22(R)-hydroxycholesterol, 24(S)-hydroxycholesterol, T0901317 or GW3965); microsomal triglyceride transfer protein (MTP) inhibitors, anti-diabetes agents such as, e.g. insulin and insulin analogs (e.g. LysPro insulin, inhaled formulations comprising insulin; sulfonylureas and analogues (e.g. tolazamide, chlorpropamide, glipizide, glimepiride, glyburide, glibenclamide, tolbutamide, acetohexamide, glypizide), biguanides (e.g. metformin or metformin hydrochloride, phenformin, buformin) alpha2-antagonists and imidazolines (e.g. midaglizole, isaglidole, deriglidole, idazoxan, efaroxan, fluparoxan), thiazolidinediones (e.g. pioglitazone hydrochloride, rosiglitazone maleate, ciglitazone, troglitazone or balaglitazone), alpha-glucosidase inhibitors (e.g. miglitol, acarbose, epalrestat, or voglibose), meglitinides (e.g. repaglinide or nateglinide), DPP-4 inhibitors (e.g. sitagliptin phosphate, saxagliptin, vildagliptin, alogliptin or denagliptin), incretins (e.g. glucagon-like peptide-1 (GLP-1) receptor agonists (e.g. Exenatide (Byetta™), NN2211 (Liraglutide), GLP-1(7-36) amide and its analogs, GLP-1(7-37) and its analogs, AVE-0010 (ZP-10), R1583 (Taspoglutide), GSK-716155 (albiglutide, GSK/Human Genome Sciences), BRX-0585 (Pfizer/Biorexis) and CJC-1134-PC (Exendin-4:PC-DAC™ and glucose-dependent insulinotropic peptide (GIP)); amylin agonists (e.g. pramlintide, AC-137); insulin secretagogues (e.g. linogliride, nateglinide, repaglinide, mitiglinide calcium hydrate or meglitinide); SGLT-2 inhibitors (e.g. dapagliflozin (BMS), sergliflozin (Kissei), AVE 2268 (Sanofi-Aventis); Glucokinase activators such as the compounds disclosed in e.g. WO 00/58293 A1; anti-obesity agents such as nerve growth factor agonist (e.g. axokine), growth hormone agonists (e.g. AOD-9604), adrenergic uptake inhibitors (e.g. GW-320659), 5-HT (serotonin) reuptake/transporter inhibitors (e.g. Prozac), 5-HT/NA (serotonin/noradrenaline) reuptake inhibitors (e.g. sibutramine), DA (dopamine) reuptake inhibitors (e.g. Buprorion), 5-HT, NA and DA reuptake blockers, steroidal plant extracts (e.g. P57), NPY1 or 5 (neuropeptide Y Y1 or Y5) antagonists, NPY2 (neuropeptide Y Y2) agonists, MC4 (melanocortin 4) agonists, CCK-A (cholecystokinin-A) agonists, GHSR1a (growth hormone secretagogue receptor) antagonist/inverse agonists, ghrelin antibody, MCH1R (melanin concentrating hormone 1R) antagonists (e.g. SNAP 7941), MCH2R (melanin concentrating hormone 2R) agonist/antagonists, H3 (histamine receptor 3) inverse agonists or antagonists, H1 (histamine 1 receptor) agonists, FAS (Fatty acid synthase) inhibitors, ACC-2 (acetyl-CoA carboxylase-1) inhibitors, β3 (beta adrenergic receptor 3) agonists, DGAT-2 (diacylglycerol acyltransferase 2) inhibitors, DGAT-1 (diacylglycerol acyltransferase 1) inhibitors, CRF (corticotropin releasing factor) agonists, Galanin antagonists, UCP-1 (uncoupling protein-1), 2 or 3 activators, leptin or a leptin derivatives, opioid antagonists, orexin antagonists, BRS3 agonists, GLP-1 (glucagons-like peptide-1) agonists, IL-6 agonists, a-MSH agonists, AgRP antagonists, BRS3 (bombesin receptor subtype 3) agonists, 5-HT1B agonists, POMC antagonists, CNTF (ciliary neurotrophic factor or CNTF derivative), NN2211, Topiramate, glucocorticoid antagonist, Exendin-4 agonists, $5\text{-HT}_{2C}$ (serotonin receptor 2C) agonists (e.g. Lorcaserin), PDE (phosphodiesterase) inhibitors, fatty acid transporter inhibitors, dicarboxylate transporter inhibitors, glucose transporter inhibitors, CB-1 (cannabinoid-1 receptor) inverse agonists or antagonists (e.g. SR141716), lipase inhibitors (e.g. orlistat); cyclooxygenase-2 (COX-2) inhibitors (e.g. rofecoxib and celecoxib); thrombin inhibitors (e.g. heparin, argatroban, melagatran, dabigatran); platelet aggregation inhibitors (e.g. glycoprotein IIb/IIIa fibrinogen receptor antagonists or aspirin); vitamin B6 and pharmaceutically acceptable salts thereof; vitamin B 12; folic acid or a pharmaceutically acceptable salt or ester thereof; antioxidant vitamins such as C and E and beta carotene; beta blockers (e.g. angiotensin II receptor antagonists such as losartan, irbesartan or valsartan; antiotensin converting enzyme inhibitors such as enalapril and captopril; calcium channel blockers such as nifedipine and diltiazam; endothelian antagonists; aspirin; agents other than LXR ligands that enhance ATP-Binding Cassette Transporter-Al gene expression; and bisphosphonate compounds (e.g. alendronate sodium).

The following tests were carried out in order to determine the activity of the compounds of formula I. Background information on the binding assay can be found in: Nichols J S et al. "Development of a scintillation proximity assay for peroxisome proliferator-activated receptor gamma ligand binding domain", (1998) Anal. Biochem. 257: 112-119.

Bacterial and mammalian expression vectors were constructed to produce glutathione-s-transferase (GST) and Gal4 DNA binding domain (GAL) proteins fused to the ligand binding domain (LBD) of human FXR (aa 193-473). To accomplish this, the portions of the sequences encoding the FXR LBD were amplified by polymerase chain reaction (PCR) from a full-length clone by PCR and then subcloned into the plasmid vectors. The final clone was verified by DNA sequence analysis.

The induction, expression, and subsequent purification of GST-LBD fusion protein was performed in *E. coli* strain BL21(pLysS) cells by standard methods (Current Protocols in Molecular Biology, Wiley Press, ed. Ausubel et al).

Radioligand Binding Assay

Binding of test substances to the FXR ligand binding domain was assessed in a radioligand displacement assay. The assay was performed in a buffer consisting of 50 mM Hepes, pH 7.4, 10 mM NaCl, 5 mM $MgCl_2$. For each reaction well in a 96-well plate, 40 nM of GST-FXR LBD fusion protein was bound to 10 μg glutathione ytrium silicate SPA beads (Pharmacia Amersham) in a final volume of 50 μl by shaking. A radioligand (eg. 40 nM) of 2,N-dicyclohexyl-2-[2-(2,4 dimethoxy-phenyl)-benzoimidazol-1-yl]-acetamide) was added, and the reaction incubated at RT for 30 minutes in the presence of test compounds followed by scintillation proximity counting. All binding assays were performed in 96-well plates and the amount of bound ligand was measured on a Packard TopCount using OptiPlates (Packard). Dose response curves were performed within a range of concentration from $6 \times 10^{-9}$ M to $2.5 \times 10^{-5}$ M.

Luciferase Transcriptional Reporter Gene Assays

Baby hamster kidney cells (BHK21 ATCC CCL10) were grown in DMEM medium containing 10% FBS at 37° C. in a 95% $O_2$:5% $CO_2$ atmosphere. Cells were seeded in 6-well plates at a density of $10^5$ cells/well and then transfected with the pFA-FXR-LBD or expression plasmid plus a reporter plasmid. Transfection was accomplished with the Fugene 6 reagent (Roche Molecular Biochemicals) according to the suggested protocol. Six hours following transfection, the cells were harvested by trypsinization and seeded in 96-well plates at a density of $10^4$ cells/well. After 24 hours to allow attachment of cells, the medium was removed and replaced with 100 μl of phenol red-free medium containing the test substances or control ligands (final DMSO concentration: 0.1%). Following incubation of the cells for 24 hours with substances, 50 μl of the supernatant was discarded and then 50 μl of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula I have an activity in at least one of the above assays ($EC_{50}$ or $IC_{50}$), preferably in the range of 0.5 nM to 10 μM, more preferably 0.5 nM to 100 nM. For example, compounds of formula I of the present invention showed the following $IC_{50}$ values in the binding assay described above:

| Example | $IC_{50}$ [μM] |
| --- | --- |
| 1 | 1.92 |
| 2 | 9.17 |
| 3 | 7.44 |
| 4 | 1.39 |
| 5 | 2.05 |
| 6 | 0.155 |
| 7 | 0.80 |
| 8 | 1.06 |
| 9 | 4.86 |
| 11 | 1.3 |
| 12 | 7.3 |
| 13 | 4.9 |
| 14 | 2.83 |
| 16 | 0.223 |
| 17 | 7.54 |
| 18 | 0.36 |
| 20 | 0.33 |
| 22 | 2.06 |
| 23 | 0.021 |
| 24 | 0.68 |
| 26 | 0.57 |
| 27 | 0.245 |
| 28 | 0.51 |
| 29 | 0.026 |
| 31 | 0.10 |
| 32 | 1.7 |
| 34 | 2.13 |
| 35 | 0.87 |
| 36 | 0.40 |
| 37 | 3.48 |
| 38 | 0.109 |
| 40 | 0.36 |
| 41 | 7.13 |
| 42 | 0.014 |
| 43 | 0.029 |
| 44 | 5.62 |
| 47 | 0.002 |
| 49 | 0.004 |
| 50 | 0.058 |
| 52 | 0.004 |
| 53 | 0.73 |
| 55 | 0.042 |
| 56 | 0.17 |
| 57 | 0.045 |
| 58 | 0.053 |
| 59 | 3.04 |
| 61 | 0.13 |
| 62 | 0.08 |
| 63 | 0.2 |
| 64 | 0.25 |
| 65 | 0.004 |

The compounds of formula I and their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following examples serve to illustrate the present invention in more detail. They are, however, not intended to limit its scope in any manner.

EXAMPLES

Abbreviations $CH_2Cl_2$=dichloromethane, d=day, DCM=dichloromethane, DIPEA=N,N-diisopropylethylamine, DMAP=4-(dimethylamino)-pyridine, DMF=N,N-dimethylformamide, DMSO=dimethyl sulfoxide, ee=enantiomeric excess, $Et_3N$=triethylamine, EtOAc=ethyl acetate, h=hour, HATU=2-(1H-7-azabenzotriazol-1-yl)-1,1,3,3-tetramethyl uronium hexafluorophosphate, HCl=hydrochloric acid, HPLC=high performance liquid chromatography, iPrOAc=isoproyl acetate, LDA=lithium diisopropylamide, LiHMDS=lithium hexamethyldisilazide, MeOH=methanol, min=minutes, $NaHCO_3$=sodium bicarbonate, NaOH=sodium hydroxide, $Na_2SO_4$=sodium sulfate, quant.=quantitative, rt=room temperature, TBME=tert-butylmethyl ether, THF=tetrahydrofuran, TLC=thin layer chromatography.

Example 1

2,N-Dicyclohexyl-2-(2-phenyl-2H-indazol-3-yl)-acetamide

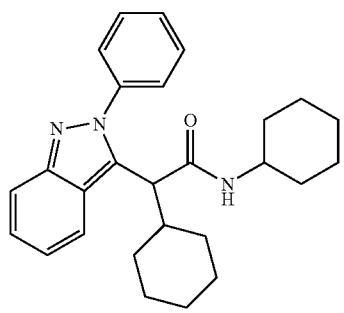

1.1 Cyclohexyl-(2-phenyl-2H-indazol-3-yl)-amine

To a solution of 2-phenyl-2H-indazol-3-amine (800 mg, 4 mmol; Shirtcliff, Laura D.; Rivers, Jazmin; Haley, Michael M, Journal of Organic Chemistry (2006), 71(17), 6619-6622) in $CH_2Cl_2$ (43 ml) was added cyclohexanone (1.97 ml, 19 mmol; CAS Reg. No. 108-94-1), acetic acid (0.22 ml, 4 mmol) and sodium triacetoxyborhydride (2.43 g, 11 mmol) at ambient temperature under an argon atmosphere. The reaction mixture was heated under reflux conditions for 12 h, poured onto ice water/aqueous $NaHCO_3$ solution 1/1 and extracted two times with $CH_2Cl_2$. The combined extracts were washed with ice water/brine 1/1 and dried over $Na_2SO_4$. After filtration the solvent was removed under reduced pressure, the resulting brown oil was dissolved in MeOH (20 ml) and heated under reflux conditions for 30 min. Removal of the solvent under reduced pressure left a brown oil which was purified by column chromatography (silica gel, iPrOAc/heptane) to give the title compound (206 mg, 0.7 mmol; 18%) as yellow oil. MS: m/e=292.4 [M+H$^+$].

1.2 2,N-Dicyclohexyl-2-(2-phenyl-2H-indazol-3-yl)-acetamide

To a solution of cyclohexyl-(2-phenyl-2H-indazol-3-yl)-amine (30 mg, 103 µmol) in chloroform was added $Et_3N$ (16 µl, 113 µmol) and cyclohexylacetylchloride (16 µl, 108 µmol; CAS Reg. No. 23860-35-7) at ambient temperature under an argon atmosphere. The mixture was heated to 80° C. for 12 h, poured onto ice water/1 N HCl 1/1 and extracted two times with iPrOAc. The combined extracts were washed with ice water/1 N NaOH 1/1 and ice water/brine 1/1 and dried over $Na_2SO_4$. After filtration the solvent was removed under reduced pressure and the crude product was purified by preparative thin layer chromatography (silica gel, iPrOAc/heptane) to give the title compound (27 mg, 65 µmol; 63%) as colorless foam. MS: m/e=416.5 [M+H$^+$].

Example 2

N-Cyclohexyl-2-(3-methoxy-phenyl)-2-(2-phenyl-2H-indazol-3-yl)-acetamide

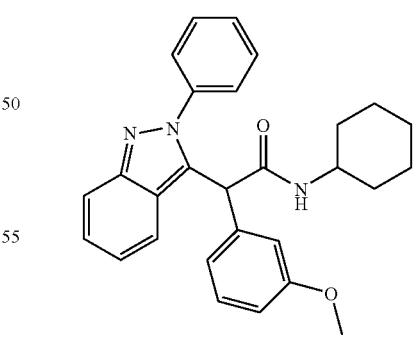

In analogy to the procedure described in example 1.2, cyclohexyl-(2-phenyl-2H-indazol-3-yl)-amine (example 1.1) was reacted with 3-methoxyphenyl acetyl chloride ([6834-42-0]) in the presence of $Et_3N$ to give the title compound as yellow foam. MS: m/e=440.4 [M+H$^+$].

Example 3

N-Cyclohexyl-2-phenyl-2-(2-phenyl-2H-indazol-3-Yl)-acetamide

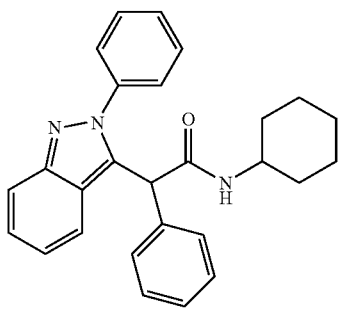

In analogy to the procedure described in example 1.2, cyclohexyl-(2-phenyl-2H-indazol-3-yl)-amine (example 1.1) was reacted with phenyl-acetyl chloride (CAS Reg. No. 103-80-0) in the presence of Et$_3$N to give the title compound as yellow foam. MS: m/e=410.1 [M+H$^+$].

Example 4

2-[2-(4-Chloro-phenyl)-2H-indazol-3-yl]-2,N-dicyclohexyl-acetamide

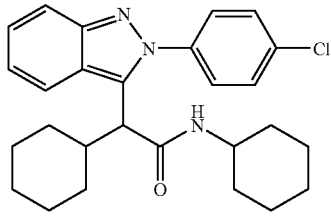

4.1
3-Benzotriazol-1-yl-2-cyclohexyl-3-oxo-propionic acid ethyl ester

A solution of 2-cyclohexyl-malonic acid monoethyl ester (2.9 g, 14 mmol; CAS Reg. No. 147596-63-2) in thionyl chloride (29 ml) was heated under reflux conditions for 2 h. The solvent was removed under reduced pressure to give chlorocarbonyl-cyclohexyl-acetic acid ethyl ester. 1,2,3-Benzotriazole (1.47 g, 12 mmol) was dissolved at ambient temperature under an argon atmosphere in CH$_2$Cl$_2$ (45 ml). Et$_3$N (1.86 ml, 13 mmol) and a solution of chlorocarbonyl-cyclohexyl-acetic acid ethyl ester in CH$_2$Cl$_2$ (4 ml) was added. The reaction mixture was stirred at ambient temperature for 14 h, quenched with ice cold aqueous 2 N HCl and extracted two times with iPrOAc. The combined extracts were washed with ice water/1 N aqueous HCl solution, ice water/brine 1/1 and dried over Na$_2$SO$_4$. After filtration the solvent was removed under reduced pressure to give a yellow oil which was purified by column chromatography (silica gel, iPrOAc/heptane) to give the title compound (1.05 g, 3.3 mmol; 25%) as yellow oil. MS: m/e=316.2 [M+H$^+$].

4.2
2-Cyclohexyl-3-oxo-3-(2-oxo-cyclohexyl)-propionic acid ethyl ester To a −78° C. cold solution of LDA (2 M solution in heptane/ethylbenzene/THF, 1.8 ml, 3.66 mmol) in THF (16.8 ml) under an argon atmosphere was added a solution of cyclohexanone (380 µl, 3.66 mmol; CAS Reg. No. 108-94-1) in THF (12.6 ml) within 10 min. The mixture was stirred for 1 h at −78° C. A solution of 3-benzotriazol-1-yl-2-cyclohexyl-3-oxo-propionic acid ethyl ester (1.05 g, 3.33 mmol) in THF (11.1 ml) was added and the solution was stirred at ambient temperature for 14 h. Ice water was added, the mixture was poured onto ice water/brine 1/1 and extracted two times with TBME. The combined extracts were washed with ice water/brine 1/1 and dried over Na$_2$SO$_4$. After filtration the solvent was removed under reduced pressure to give a yellow oil which was purified by column chromatography (silica gel, iPrOAc/heptane) to give the title compound (209 mg, 0.71 mmol; 21%) as yellow oil. MS: m/e=295.2 [M+H$^+$].

4.3 [2-(4-Chloro-phenyl)-4,5,6,7-tetrahydro-2H-indazol-3-yl]-cyclohexyl-acetic acid ethyl ester (4-Chloro-phenyl)-hydrazine (100 mg, 700 µmol; CAS Reg. No. 1073-69-4) was added to a solution of 2-cyclohexyl-3-oxo-3-(2-oxo-cyclohexyl)-propionic acid ethyl ester (206 mg, 700 µmol) in ethanol (4.7 ml). The reaction mixture was heated under reflux conditions for 6 h. The solvent was removed under reduced pressure. The residue was taken up in ice water/brine 1/1 and extracted two times with iPrOAc. The combined extracts were washed with ice water/brine 1/1 and dried over Na$_2$SO$_4$. After filtration the solvent was removed under reduced pressure to give a brown oil which was purified by preparative thick layer chromatography (silica gel, iPrOAc/heptane) to give the title compound (130 mg, 324 µmol; 46%) as orange solid. MS: m/e=401.2 [M+H$^+$].

4.4 [2-(4-Chloro-phenyl)-2H-indazol-3-yl]-cyclohexyl-acetic acid ethyl ester 2,3-Dichloro-5,6-dicyanobenzoquinone (136 mg, 600 µmol) was added to a solution of [2-(4-chloro-phenyl)-4,5,6,7-tetrahydro-2H-indazol-3-yl]-cyclohexyl-acetic acid ethyl ester (60 mg, 150 µmol in dioxane (3.3 ml) under an argon atmosphere. The reaction mixture was heated under reflux conditions for 4 d. The solvent was removed under reduced pressure and the residue was purified by column chromatography (silica gel, iPrOAc/heptane) to give the title compound (11 mg, 28 µmol; 19%) as colorless solid. MS: m/e=397.0 [M+H$^+$].

4.5 [2-(4-Chloro-phenyl)-2H-indazol-3-yl]-cyclohexyl-acetic acid

A solution of [2-(4-chloro-phenyl)-2H-indazol-3-yl]-cyclohexyl-acetic acid ethyl ester (9 mg, 23 µmol) in MeOH (0.5 ml) and 4 N aqueous NaOH (90 µl, 345 µmol) was heated for 14 h under reflux conditions. The solvent was removed under reduced pressure, ice water/1 N aqueous NaOH solution/TBME 1/1/2 was added and the layers were separated. The aqueous layer was extracted one more time with TBME. The aqueous layer was acidified with 1 N aqueous HCl solution and extracted two times with iPrOAc. The combined extracts were washed with ice water/brine 1/1 and dried over Na$_2$SO$_4$. After filtration the solvent was removed under reduced pressure to give the title compound (10 mg; quant.) as off-white solid which was sufficiently pure to be used in the next step. MS: m/e=369.1 [M+H$^+$].

4.6 2-[2-(4-Chloro-phenyl)-2H-indazol-3-yl]-2,N-dicyclohexyl-acetamide

To an ice cold solution of [2-(4-chloro-phenyl)-2H-indazol-3-yl]-cyclohexyl-acetic acid (9 mg, 24 µmol and cyclohexylamine (2.3 µl, 24 µmol; CAS Reg. No. 108-91-8) in CH$_2$Cl$_2$ (1 ml) under an argon atmosphere was added bromotripyrrolidinophosphonium hexafluorophosphate (17 mg, 36 umol) and N,N-diisopropylethylamine (10 ul, 72 umol). The reaction mixture was stirred for 5 d at ambient temperature, poured onto ice water/1 N aqueous NaOH solution 1/1 and extracted two times with iPrOAc. The combined extracts were washed with ice water/1 N aqueous HCl solution 1/1 and brine and dried over Na$_2$SO$_4$. After filtration the solvent was removed under reduced pressure and the residue was purified by preparative thin layer chromatography (silica gel, iPrOAc/heptane) to give the title compound (5 mg, 11 µmol; 46%) as colorless foam. MS: m/e=450.3 [M+H$^+$].

Example 5

4-{2-[2-(4-Chloro-phenyl)-4,5,6,7-tetrahydro-2H-indazol-3-yl]-2-cyclohexyl-2-hydroxy-acetylamino}-3-fluoro-benzoic acid

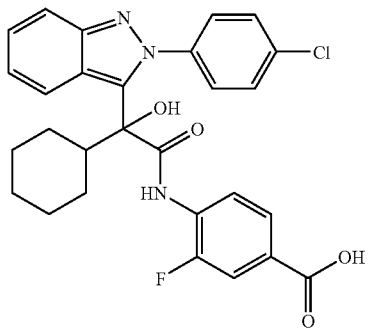

5.1 [2-(4-Chloro-phenyl)-4,5,6,7-tetrahydro-2H-indazol-3-yl]-cyclohexyl-acetic acid In analogy to the procedure described in example 4.5, [2-(4-chloro-phenyl)-4,5,6,7-tetrahydro-2H-indazol-3-yl]-cyclohexyl-acetic acid ethyl ester (example 4.3) was treated with aqueous NaOH solution in MeOH to give the title compound as yellow foam which was sufficiently pure to be used in the next step. MS: m/e=373.2 [M+H$^+$].

5.2 4-{2-[2-(4-Chloro-phenyl)-4,5,6,7-tetrahydro-2H-indazol-3-yl]-2-cyclohexyl-2-hydroxy-acetylamino}-3-fluoro-benzoic acid ethyl ester To a solution of [2-(4-chloro-phenyl)-4,5,6,7-tetrahydro-2H-indazol-3-yl]-cyclohexyl-acetic acid (60 mg, 161 µmol) in CH$_2$Cl$_2$ (0.8 ml) under an argon atmosphere was added pyridine (16 µl, 202 µmol) and thionyl chloride (14 µl, 193 µmol). 4-Amino-3-fluoro-benzoic acid ethyl ester (29 mg, 161 µmol; CAS Reg. No. 73792-12-8) and pyridine (16 µl, 202 µmol) were added and the reaction mixture was stirred at ambient temperature for 48 h. Ice water/25% aqueous HCl solution 1/1 was added and the mixture was extracted three times with CH$_2$Cl$_2$. The combined extracts were washed with ice water/brine 1/1 and dried over Na$_2$SO$_4$. After filtration the solvent was removed under reduced pressure to give a brown solid which was purified by preparative thick layer chromatography (silica gel, iPrOAc/heptane) to obtain the title compound (9 mg, 16 µmol; 10%) as colorless solid. MS: m/e=554.4 [M+H$^+$].

5.3 4-{2-[2-(4-Chloro-phenyl)-4,5,6,7-tetrahydro-2H-indazol-3-yl]-2-cyclohexyl-2-hydroxy-acetylamino}-3-fluoro-benzoic acid To a solution of 4-{2-[2-(4-chloro-phenyl)-4,5,6,7-tetrahydro-2H-indazol-3-yl]-2-cyclohexyl-2-hydroxy-acetylamino}-3-fluoro-benzoic acid ethyl ester (6 mg, 11 µmol) in THF/MeOH 1/1 (0.2 ml) was a added a 1 N aqueous lithium hydroxide solution (60 µl, 60 µmol) at ambient temperature under an argon atmosphere. The reaction mixture was stirred for 12 h at ambient temperature and poured onto ice water/1 N aqueous NaOH solution 1/1. The layers were separated, the aqueous layer was acidified with ice cold 1 N aqueous HCl solution and extracted two times with iPrOAc. The combined extracts were washed with ice water/brine 1/1 and dried over Na$_2$SO$_4$. After filtration the solvent was removed under reduced pressure to give the title compound (7 mg; quant.) as yellow solid. MS: m/e=526.4 [M+H$^+$].

Example 6

2-[2-(4-Chloro-phenyl)-4,5,6,7-tetrahydro-2H-indazol-3-yl]-2,N-dicyclohexyl-acetamide

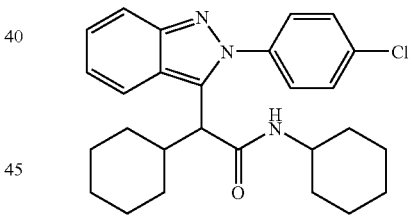

A solution of [2-(4-chloro-phenyl)-4,5,6,7-tetrahydro-2H-indazol-3-yl]-cyclohexyl-acetic acid (20 mg, 54 µmol; example 5.1) in thionyl chloride (39 µl, 536 µmol) was heated under reflux conditions for 45 min. The solvent was removed under reduced pressure and the resulting crude [2-(4-chloro-phenyl)-4,5,6,7-tetrahydro-2H-indazol-3-yl]-cyclohexyl-acetyl chloride was dissolved in CH$_2$Cl$_2$ (0.2 ml) and added to a solution of cyclohexylamine (7 µl, 59 µmol; CAS Reg. No. 108-91-8) and DMAP (20 mg, 162 µmol) in CH$_2$Cl$_2$ (0.2 ml). The reaction mixture was stirred at ambient temperature for 48 h. Ice water/brine 1/1 was added and the mixture was extracted two times with iPrOAc. The combined extracts were washed with ice water/brine 1/1 and dried over Na$_2$SO$_4$. After filtration the solvent was removed under reduced pressure to give a brown oil which was purified by preparative thick layer chromatography (silica gel, iPrOAc/heptane) to obtain the title compound (15 mg, 33 µmol; 62%) as colorless foam. MS: m/e=454.4 [M+H$^+$].

Example 7

4-{2-[2-(4-Chloro-phenyl)-4,5,6,7-tetrahydro-2H-indazol-3-yl]-2-cyclohexyl-acetylamino}-benzoic acid

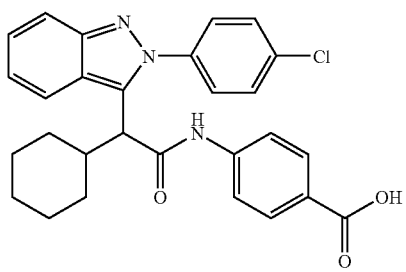

7.1 4-{2-[2-(4-Chloro-phenyl)-4,5,6,7-tetrahydro-2H-indazol-3-yl]-2-cyclohexyl-acetylamino}-benzoic acid ethyl ester In analogy to the procedure described in example 6, [2-(4-chloro-phenyl)-4,5,6,7-tetrahydro-2H-indazol-3-yl]-cyclohexyl-acetic acid (example 5.1) was converted into the corresponding acid chloride with thionyl chloride which subsequently reacted with 4-amino-benzoic acid ethyl ester (CAS Reg. No. 94-09-7) in the presence of DMAP to give the title compound as yellow oil. MS: m/e=520.4 [M+H$^+$].

7.2 4-{2-[2-(4-Chloro-phenyl)-4,5,6,7-tetrahydro-2H-indazol-3-yl]-2-cyclohexyl-acetylamino}-benzoic acid To a solution of 4-{2-[2-(4-chloro-phenyl)-4,5,6,7-tetrahydro-2H-indazol-3-yl]-2-cyclohexyl-acetylamino}-benzoic acid ethyl ester (23 mg, 44 µmol) in THF (0.5 ml) and MeOH (0.3 ml) was a added a 1 N aqueous lithium hydroxide solution (270 µl, 264 µmol) at ambient temperature under an argon atmosphere. The reaction mixture was stirred for 6 h at ambient temperature and poured onto ice water/1 N aqueous HCl solution 1/1. The mixture was extracted two times with iPrOAc. The combined extracts were washed with ice water/brine 1/1 and dried over Na$_2$SO$_4$. After filtration the solvent was removed under reduced pressure to obtain a yellow solid which was purified by preparative thick layer chromatography (silica gel, iPrOAc/heptane) to give the title compound (5 mg, 10 µmol; 23%) as yellow oil. MS: m/e=492.4 [M+H$^+$].

Example 8

2-[2-(4-Chloro-phenyl)-4,5,6,7-tetrahydro-2H-indazol-3-yl]-2-cyclohexyl-N-cyclopentyl-acetamide

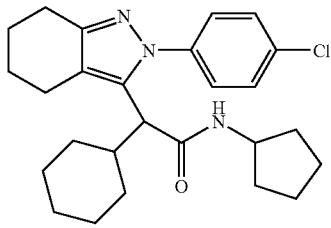

In analogy to the procedure described in example 6, [2-(4-chloro-phenyl)-4,5,6,7-tetrahydro-2H-indazol-3-yl]-cyclohexyl-acetic acid (example 5.1) was converted into the corresponding acid chloride with thionyl chloride which subsequently reacted with cyclopentylamine (CAS Reg. No. 1003-03-8) in the presence of DMAP to give a mixture of 2-[2-(4-chloro-phenyl)-4,5,6,7-tetrahydro-2H-indazol-3-yl]-2-cyclohexyl-N-cyclopentyl-acetamide and 2-[2-(4-chloro-phenyl)-4,5,6,7-tetrahydro-2H-indazol-3-yl]-2-cyclohexyl-N-cyclopentyl-2-hydroxy-acetamide. Purification by preparative thick layer chromatography (silica gel, iPrOAc/heptane) gives the title compound as yellow oil. MS: m/e=440.4 [M+H$^+$].

Example 9

2-[2-(4-Chloro-phenyl)-4,5,6,7-tetrahydro-2H-indazol-3-yl]-2-cyclohexyl-N-cyclopentyl-2-hydroxy-acetamide

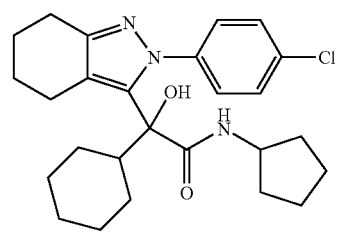

In analogy to the procedure described in example 6, [2-(4-chloro-phenyl)-4,5,6,7-tetrahydro-2H-indazol-3-yl]-cyclohexyl-acetic acid (example 5.1) was converted into the corresponding acid chloride with thionyl chloride which subsequently reacted with cyclopentylamine (CAS Reg. No. 1003-03-8]) in the presence of DMAP to give a mixture of 2-[2-(4-chloro-phenyl)-4,5,6,7-tetrahydro-2H-indazol-3-yl]-2-cyclohexyl-N-cyclopentyl-acetamide and 2-[2-(4-chloro-phenyl)-4,5,6,7-tetrahydro-2H-indazol-3-yl]-2-cyclohexyl-N-cyclopentyl-2-hydroxy-acetamide. Purification by preparative thick layer chromatography (silica gel, iPrOAc/heptane) gives the title compound as colorless oil. MS: m/e=456.3 [M+H$^+$].

Example 10

2-[2-(4-Chloro-phenyl)-2H-indazol-3-14]-2-cyclohexyl-N-(4-hydroxy-cyclohexyl)-acetamide

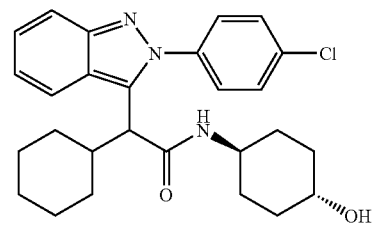

10.1 [2-(4-Chloro-phenyl)-2H-indazol-3-yl]-cyclohexyl-methanol

A 1.6 M solution of n-butyllithium in hexane (5.7 ml, 9.1 mmol) was added within 10 min to a −78° C. cold solution of N,N'-diisopropylethylamine (1.55 ml, 9.1 mmol) in THF (25.5 ml). The solution was stirred for 10 min at 5° C. and cooled again to −78° C. A solution of 2-(4-chloro-phenyl)-2H-indazole (1.7 g, 7.4 mmol; Liu, Rui; Zhu, Yong-ming; Qin, Lie-na; Ji, Shun-jun; Katayama, Haji. Heterocycles (2007), 71(8), 1755-1763.) in THF (8.5 ml) was added, the suspension was stirred for 15 min at 0° C., cooled to −78° C. and cyclohexane-carbaldehyde (1.1 ml, 9.1 mmol; CAS Reg. No. 2043-61-0) was added. The reaction mixture was stirred at ambient temperature for 14 h. Under ice cooling saturated aqueous ammonium chloride solution was added and the mixture was extracted two times with iPrOAc. The combined extracts were washed with ice water/brine 1/1 and dried over Na$_2$SO$_4$. After filtration the solvent was removed under reduced pressure and the residue was purified by column chromatography (silica gel, iPrOAc/heptane) to give the title compound (1.1 g, 3.2 mmol; 43%) as yellow foam. MS: m/e=341.2 [M+H$^+$].

10.2 [2-(4-Chloro-phenyl)-2H-indazol-3-yl]-cyclohexyl-methanone

2-Iodoxybenzoic acid (1.42 g, 2.3 mmol; 45% purity) was added to an ice cold solution of [2-(4-chloro-phenyl)-2H-indazol-3-yl]-cyclohexyl-methanol (520 mg, 1.5 mmol) in THF/DMSO 1/1 (28 ml). The reaction mixture was stirred for 1 h at ambient temperature, ice water/brine 1/1 was added and the mixture was extracted two times with iPrOAc. The combined extracts were washed with ice water/saturated aqueous ammonium chloride solution 1/1 and dried over Na$_2$SO$_4$. After filtration the solvent was removed under reduced pressure and the residue was purified by column chromatography (silica gel, iPrOAc/heptane) to give the title compound (404 mg, 1.2 µmol; 78%) as colorless solid. MS: m/e=339.1 [M+H$^+$].

10.3 [2-(4-Chloro-phenyl)-2H-indazol-3-yl]-cyclohexyl-trimethylsilanyloxy-acetonitrile Trimethylsilyl cyanide (453 ul, 3.4 mmol) was added to a mixture of [2-(4-chloro-phenyl)-2H-indazol-3-yl]-cyclohexyl-methanone (345 mg, 1 mmol) and zinc(II) iodide (6 mg, 19 µmol) under an argon atmosphere. The suspension was stirred at ambient temperature for 14 h, trimethylsilyl cyanide (453 µl, 3.4 mmol) and zinc (II) iodide (6 mg, 19 mop were added and the suspension was stirred for 10 h at 50° C. Ice water/brine 1/1 was added and the mixture was extracted two times with iPrOAc. The combined extracts were washed with ice water/brine 1/1 and dried over Na$_2$SO$_4$. After filtration the solvent was removed under reduced pressure to obtain a brown oil which was purified by column chromatography (silica gel, iPrOAc/heptane) to give the title compound (182 mg, 415 umol; 41%) as colorless oil. MS: m/e=438.4 [M+H$^+$].

10.4 [2-(4-Chloro-phenyl)-2H-indazol-3-yl]-cyclohexyl-acetic acid

Tin (II) chloride (312 mg, 1.6 mmol) was added to a suspension of [2-(4-chloro-phenyl)-2H-indazol-3-yl]-cyclohexyl-trimethylsilanyloxy-acetonitrile (180 mg, 411 µmol) in acetic acid (730 µl) and 25% aqueous HCl solution (730 µl). The mixture was stirred at 140° C. for 72 h, cooled to ambient temperature, poured onto ice water and extracted two times with CH$_2$Cl$_2$. The combined extracts were washed with ice water/2 N aqueous NaOH solution 1/1. The aqueous layer was extracted two times with TBME, acidified with 2 N aqueous HCl solution and extracted two times with iPrOAc. The combined extracts were washed with ice water/brine 1/1 and dried over Na$_2$SO$_4$. After filtration the solvent was removed under reduced pressure to give the title compound (69 mg, 187 µmol; 46%) as colorless solid. MS: m/e=369.1 [M+H$^+$].

10.5 2-[2-(4-Chloro-phenyl)-2H-indazol-3-yl]-2-cyclohexyl-(trans)-N-(4-hydroxy-cyclohexyl)-acetamide In analogy to the procedure described in example 6, [2-(4-chloro-phenyl)-2H-indazol-3-yl]-cyclohexyl-acetic acid was converted into the corresponding acid chloride with thionyl chloride which subsequently reacted with (trans)-4-amino-cyclohexanol (CAS Reg. No. 27489-62-9) in the presence of DMAP to give the title compound as colorless oil. MS: m/e=466.4 [M+H$^+$].

Example 11

4-{2-[2-(4-Chloro-phenyl)-4,5,6,7-tetrahydro-2H-indazol-3-yl]-2-cyclohexyl-acetylamino}-3-fluoro-benzoic acid

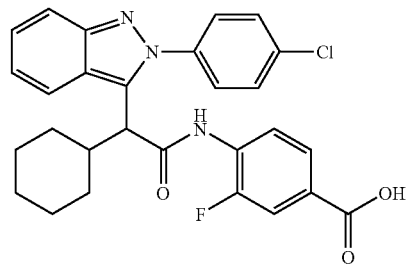

11.1 4-{2-[2-(4-Chloro-phenyl)-4,5,6,7-tetrahydro-2H-indazol-3-yl]-2-cyclohexyl-acetylamino}-3-fluoro-benzoic acid ethyl ester In analogy to the procedure described in example 6, [2-(4-chloro-phenyl)-4,5,6,7-tetrahydro-2H-indazol-3-yl]-cyclohexyl-acetic acid (example 5.1) was converted into the corresponding acid chloride with thionyl chloride which subsequently reacted with 4-amino-3-fluoro-benzoic acid ethyl ester (CAS Reg. No. 73792-12-8) in the presence of DMAP to give the title compound as yellow oil. MS: m/e=538.4 [M+H$^+$].

11.2 4-{2-[2-(4-Chloro-phenyl)-4,5,6,7-tetrahydro-2H-indazol-3-yl]-2-cyclohexyl-acetylamino}-3-fluoro-benzoic acid In analogy to the procedure described in example 7.2, 4-{2-[2-(4-chloro-phenyl)-4,5,6,7-tetrahydro-2H-indazol-3-yl]-2-cyclohexyl-acetylamino}-3-fluoro-benzoic acid ethyl ester was treated with 1 N aqueous lithium hydroxide solution in THF and MeOH to give the title compound as off-white oil. MS: m/e=510.3 [M+H$^+$].

Example 12

4-{2-[2-(4-Chloro-phenyl)-2H-indazol-3-yl]-2-cyclohexyl-acetylamino}-benzoic acid

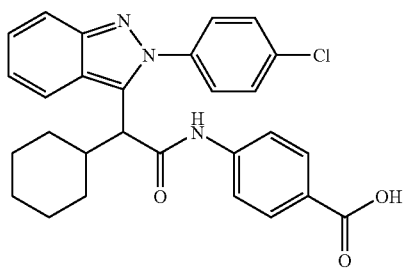

12.1 4-{2-[2-(4-Chloro-phenyl)-2H-indazol-3-yl]-2-cyclohexyl-acetylamino}-benzoic acid ethyl ester In analogy to the procedure described in example 6, [2-(4-chloro-phenyl)-2H-indazol-3-yl]-cyclohexyl-acetic acid was converted into the corresponding acid chloride with thionyl chloride which subsequently reacted with 4-amino-benzoic acid ethyl ester (CAS Reg. No. 94-09-7]) in the presence of DMAP to give the title compound as colorless oil. MS: m/e=516.4 [M+H⁺].

12.2 4-{2-[2-(4-Chloro-phenyl)-2H-indazol-3-yl]-2-cyclohexyl-acetylamino}-benzoic acid In analogy to the procedure described in example 7.2, 4-{2-[2-(4-chloro-phenyl)-2H-indazol-3-yl]-2-cyclohexyl-acetylamino}-benzoic acid ethyl ester was treated with 1 N aqueous lithium hydroxide solution in THF and MeOH to give the title compound as yellow oil. MS: m/e=488.4 [M+H⁺].

Example 13

4-{2-[2-(4-Chloro-phenyl)-2H-indazol-3-yl]-2-cyclohexyl-acetylamino}-3-fluoro-benzoic acid

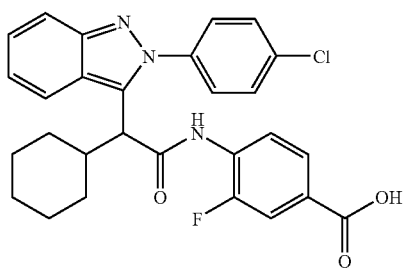

13.1 4-{2-[2-(4-Chloro-phenyl)-2H-indazol-3-yl]-2-cyclohexyl-acetylamino}-3-fluoro-benzoic acid ethyl ester In analogy to the procedure described in example 6, [2-(4-chloro-phenyl)-2H-indazol-3-yl]-cyclohexyl-acetic acid was converted into the corresponding acid chloride with thionyl chloride which subsequently reacted with 4-amino-3-fluoro-benzoic acid ethyl ester (CAS Reg. No. 73792-12-8) in the presence of DMAP to give the title compound as colorless oil. MS: m/e=534.3 [M+H⁺].

13.2 4-{2-[2-(4-Chloro-phenyl)-2H-indazol-3-yl]-2-cyclohexyl-acetylamino}-3-fluoro-benzoic acid In analogy to the procedure described in example 7.2, 4-{2-[2-(4-chloro-phenyl)-2H-indazol-3-yl]-2-cyclohexyl-acetylamino}-3-fluoro-benzoic acid ethyl ester was treated with 1 N aqueous lithium hydroxide solution in THF and MeOH to give the title compound as yellow oil. MS: m/e=506.2 [M+H⁺].

Example 14

[rac]-2-[2-(4-Chloro-phenyl)-4,5,6,7-tetrahydro-2H-indazol-3-yl]-2-cyclohexyl-N-(2,4-difluoro-phenyl)-acetamide

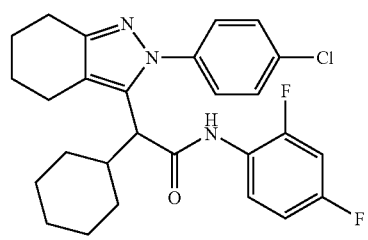

In analogy to the procedure described in example 6, [2-(4-chloro-phenyl)-4,5,6,7-tetrahydro-2H-indazol-3-yl]-cyclohexyl-acetic acid (example 5.1) was converted into the corresponding acid chloride with thionyl chloride which subsequently reacted with 2,4-difluoroaniline (CAS Reg. No. 367-25-9) in the presence of DMAP to give [rac]-2-[2-(4-chloro-phenyl)-4,5,6,7-tetrahydro-2H-indazol-3-yl]-2-cyclohexyl-N-(2,4-difluoro-phenyl)-acetamide as yellow oil. MS: m/e=484.3 [M+H⁺].

Example 15

[rac]-1-(4-{2-[2-(4-Chloro-phenyl)-4,5,6,7-tetrahydro-2H-indazol-3-yl]-2-cyclohexyl-acetylamino}-3-fluoro-phenoxy)-cyclopropanecarboxylic acid methyl ester

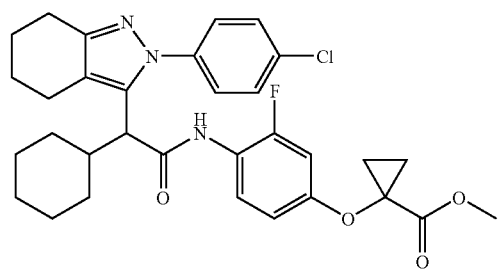

15.1 4-Bromo-2-(3-fluoro-4-nitro-phenoxy)-butyric acid methyl ester

To the solution of 5.5 g (35.0 mmol) 3-fluoro-4-nitrophenol (CAS Reg. No. 399-95-1) in 55 mL N,N-dimethylformamide, 11.8 g (45.5 mmol) methyl 2,4-dibromobutyrate (CAS Reg. No. 29547-04-4) and 6.3 g (45.5 mmol) potassium carbonate were added. After stirring for 3 h the reaction mixture was poured on ethyl acetate and 1 M aqueous hydrochloric acid and extracted. The organic phases were washed with brine, dried over magnesium sulfate, filtered and evaporated. The residue was purified by column chromatography on silica gel using an MPLC system (CombiFlash Companion, Isco Inc.) eluting with a gradient of heptane:ethyl acetate (1:0 to 1:1 v/v) to afford the title compound as a light yellow oil (64%) which was pure enough to be used in the next step.

15.2 1-(3-Fluoro-4-nitro-phenoxy)-cyclopropanecarboxylic acid methyl ester

The solution of 7.5 g (22.3 mmol) 4-bromo-2-(3-fluoro-4-nitro-phenoxy)-butyric acid methyl ester in 100 mL tetrahydrofuran was cooled to −15° C. and 2.63 g (23.4 mmol) potassium tert-butoxide were added. The cooling bath was removed and the reaction was stirred for 5 h at room temperature. The dark solution was poured 200 mL ethyl acetate and 200 mL aqueous hydrochloric acid, extracted and the phases were separated. The organic layer was washed with brine and the aqueous layers extracted with ethyl acetate. The combined organic layers were dried over magnesium sulfate, filtered and evaporated. The residue was purified by column chromatography on silica gel using an MPLC system (CombiFlash Companion, Isco Inc.) eluting with a gradient of heptane:ethyl acetate (100:30 to 70:30 v/v) to afford the title compound as a light yellow oil (79%). MS (TS) m/e (M): 255.0.

15.3 1-(4-Amino-3-fluoro-phenoxy)-cyclopropanecarboxylic acid methyl ester

To a solution of 4.49 g (17.6 mmol) 1-(3-fluoro-4-nitro-phenoxy)-cyclopropanecarboxylic acid methyl ester in 50 mL ethanol 0.5 g 10% palladium on charcoal was added and the suspension stirred for 8 h at room temperature under an atmosphere of hydrogen (1.7 bar). After the addition of 100 mL ethyl acetate the catalyst was filtered off, the filtrate evaporated and dried under high vacuum to give the title compound as a brown oil (98%) which was used in the next step without further purification. MS (TS) m/e (M+H)$^+$: 226.1.

15.4 [rac]-1-(4-{2-[2-(4-Chloro-phenyl)-4,5,6,7-tetrahydro-2H-indazol-3-yl]-2-cyclohexyl-acetylamino}-3-fluoro-phenoxy)-cyclopropanecarboxylic acid methyl ester In analogy to the procedure described in example 6, [2-(4-chloro-phenyl)-4,5,6,7-tetrahydro-2H-indazol-3-yl]-cyclohexyl-acetic acid (example 5.1) was converted into the corresponding acid chloride with thionyl chloride which subsequently reacted with 1-(4-amino-3-fluoro-phenoxy)-cyclopropanecarboxylic acid methyl ester in the presence of DMAP to give the title compound as yellow oil. MS: m/e=580.4 [M+H$^+$].

Example 16

[rac]-1-(4-{2-[2-(4-Chloro-phenyl)-4,5,6,7-tetrahydro-2H-indazol-3-yl]-2-cyclohexyl-acetylamino}-3-fluoro-phenoxy)-cyclopropanecarboxylic acid

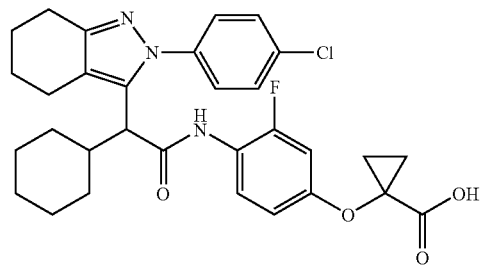

In analogy to the procedure described in example 7.2, [rac]-1-(4-{2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid methyl ester was treated with 1 N aqueous lithium hydroxide solution in THF and MeOH to give the title compound as colorless foam. MS: m/e=566.4 [M+H$^+$].

Example 17

[rac]-4-{[2-(4-Chloro-phenyl)-2H-indazol-3-yl]-cyclohexyl-methoxymethyl}-benzoic acid methyl ester

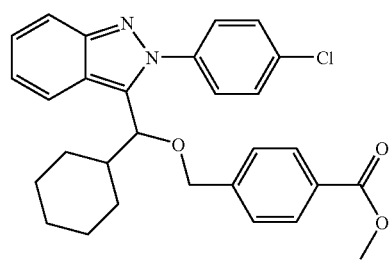

Sodium hydride (14 mg, 293 umol) was added to an ice cold solution of [2-(4-chloro-phenyl)-2H-indazol-3-yl]-cyclohexyl-methanol (50 mg, 147 umol; example 10.1) in DMF (4.5 ml) under an argon atmosphere. After 30 min. methyl-4-(chloromethyl)benzoate (41 mg, 220 umol; CAS Reg. No. 34040-64-7) was added. The mixture was stirred at ambient temperature for 5 h, poured onto ice water/brine 1/1 and extracted two times with iPrOAc. The combined extracts were washed with ice water/brine 1/1 and dried over Na$_2$SO$_4$. After filtration the solvent was removed under reduced pressure to give the crude product as brown oil which was purified by preparative HPLC on reversed phase eluting with a gradient of acetonitrile/water to give the title compound (16 mg, 33 μmol; 22%) as yellow solid. MS: m/e=489.4 [M+H$^+$].

Example 18

[rac]-4-{[2-(4-Chloro-phenyl)-2H-indazol-3-yl]-cyclohexyl-methoxymethyl}-benzoic acid

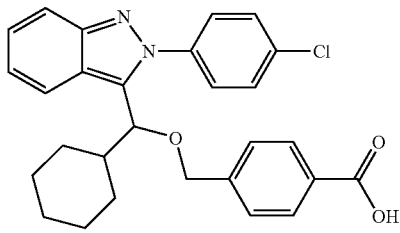

Sodium hydride (14 mg, 293 umol) was added to an ice cold solution of [2-(4-chloro-phenyl)-2H-indazol-3-yl]-cyclohexyl-methanol (50 mg, 147 umol; example 10.1) in DMF (4.5 ml) under an argon atmosphere. After 30 min. methyl-4-(chloromethyl)benzoate (41 mg, 220 umol; CAS Reg. No. 34040-64-7) was added. The mixture was stirred at ambient temperature for 5 h, poured onto ice water/brine 1/1 and extracted two times with iPrOAc. The combined extracts were washed with ice water/brine 1/1 and dried over $Na_2SO_4$. After filtration the solvent was removed under reduced pressure to give the crude product as brown oil which was purified by preparative HPLC on reversed phase eluting with a gradient of acetonitrile/water to give the title compound (3 mg, 6 μmol; 4%) as white solid. MS: m/e=475.3 [M+H$^+$].

Example 19

[rac]-4-{2-[2-(4-Chloro-phenyl)-4,5,6,7-tetrahydro-2H-indazol-3-yl]-2-cyclohexyl-acetylamino}-3-trifluoromethyl-benzoic acid methyl ester

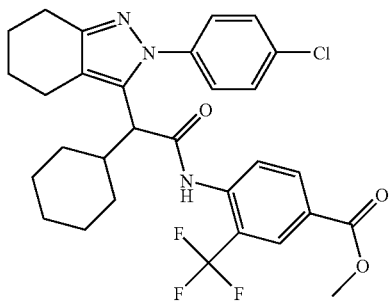

In analogy to the procedure described in example 6, [2-(4-chloro-phenyl)-4,5,6,7-tetrahydro-2H-indazol-3-yl]-cyclohexyl-acetic acid (example 5.1) was converted into the corresponding acid chloride with thionyl chloride which subsequently reacted with 4-amino-3-trifluoromethyl-benzoic acid methyl ester (CAS Reg. No. 34040-64-7 167760-75-0) in the presence of DMAP to give the title compound as yellow oil. MS: m/e=574.4 [M+H$^+$].

Example 20

[rac]-4-{2-[2-(4-Chloro-phenyl)-4,5,6,7-tetrahydro-2H-indazol-3-yl]-2-cyclohexyl-acetylamino}-3-trifluoromethyl-benzoic acid

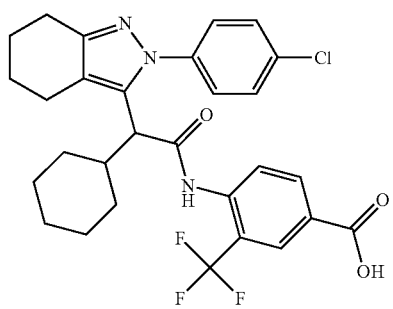

In analogy to the procedure described in example 7.2, [rac]-4-{2-[2-(4-chloro-phenyl)-4,5,6,7-tetrahydro-2H-indazol-3-yl]-2-cyclohexyl-acetylamino}-3-trifluoromethyl-benzoic acid methyl ester was treated with 1 N aqueous lithium hydroxide solution in THF and MeOH to give the title compound as brown solid. MS: m/e=558.2 [M+H$^+$].

Example 21

(−)-1-(4-{2-[2-(4-Chloro-phenyl)-4,5,6,7-tetrahydro-2H-indazol-3-yl]-2-cyclohexyl-acetylamino}-3-fluoro-phenoxy)-cyclopropanecarboxylic acid tert-butyl ester

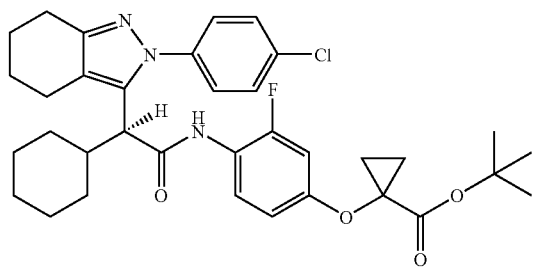

21.1 4-Bromo-2-(3-fluoro-4-nitro-phenoxy)-butyric acid tert-butyl ester

In analogy to the procedure described in example 15.1, 3-fluoro-4-nitrophenol (CAS Reg. No. 399-95-1) was reacted with tert-butyl 2,4-dibromobutyrate (CAS Reg. No. 77629-96-0) in the presence of potassium carbonate in DMF to give the title compound as yellow liquid. MS: m/e=395.0 [M+NH$_4^+$].

21.2 1-(3-Fluoro-4-nitro-phenoxy)-cyclopropanecarboxylic acid tert-butyl ester In analogy to the procedure described in example 15.2, 4-bromo-2-(3-fluoro-4-nitro-phenoxy)-butyric acid tert-butyl ester was treated with potassium tert-butoxide in THF to afford the title compound as a brown solid. MS: m/e=298.3 [M+H$^+$].

21.3 1-(4-Amino-3-fluoro-phenoxy)-cyclopropanecarboxylic acid tert-butyl ester In analogy to the procedure described in example 15.2, 1-(3-fluoro-4-nitro-phenoxy)-cyclopropanecarboxylic acid tert-butyl ester was hydrogenated in the presence of 10% palladium on charcoal in ethanol to give the title compound as brown solid. MS: m/e=268.2 [M+H$^+$].

21.4 2-(4-Chloro-phenyl)-4,5,6,7-tetrahydro-2H-indazol-3-yl]-cyclohexyl-acetic acid pentafluorophenyl ester To a solution of [2-(4-chloro-phenyl)-4,5,6,7-tetrahydro-2H-indazol-3-yl]-cyclohexyl-acetic acid (4.5 g, 12.1 mmol; example 5.1) in DMF (45 ml) was added pyridine (1.07 ml, 13.3 mmol) and pentafluorophenyl trifluoroacetate (4.16 ml, 24.1 mmol) at ambient temperature under an argon atmosphere. The reaction mixture was stirred at ambient temperature for 12 h, poured onto ice water/0.1 N HCl 1/1 and extracted two times with iPrOAc. The combined extracts were washed with ice water/sat. aqueous NaHCO$_3$ solution 1/1, ice water/brine 1/1 and dried over Na$_2$SO$_4$. After filtration the solvent was removed under reduced pressure to give 2-(4-chloro-phenyl)-4,5,6,7-tetrahydro-2H-indazol-3-yl]-cyclohexyl-acetic acid pentafluorophenyl ester as a yellow oil (9 g, 16.7 mmol; quant.) which was directly used in the next reaction step without further purification.

21.5 (−)-1-(4-{2-[2-(4-Chloro-phenyl)-4,5,6,7-tetrahydro-2H-indazol-3-yl]-2-cyclohexyl-acetylamino}-3-fluoro-phenoxy)-cyclopropanecarboxylic acid tert-butyl ester To a suspension of 2-(4-chloro-phenyl)-4,5,6,7-tetrahydro-2H-indazol-3-yl]-cyclohexyl-acetic acid pentafluorophenyl ester (5.2 g, 9.7 mmol) in DMF (118 ml) was added 1-(4-amino-3-fluoro-phenoxy)-cyclopropanecarboxylic acid tert-butyl ester (2.84 g, 11 mmol) and DMAP (5.89 g, 48.2 mmol) at ambient temperature under an argon atmosphere. The reaction mixture was stirred at ambient temperature for 14 h. The solution was poured on ice water/25% HCl 1/1 and extracted two times with iPrOAc. The combined extracts were washed with ice water/brine 1/1 and dried over Na$_2$SO$_4$. After filtration the solvent was removed under reduced pressure to give a brown oil which was purified by column chromatography (silica gel, iPrOAc/heptane) to obtain [rac]-1-(4-{2-[2-(4-Chloro-phenyl)-4,5,6,7-tetrahydro-2H-indazol-3-yl]-2-cyclohexyl-acetylamino}-3-fluoro-phenoxy)-cyclopropanecarboxylic acid tert-butyl ester (3 g, 5 mmol; 50%) as off-white solid. MS: m/e=622.5 [M+H$^+$]. [rac]-1-(4-{2-[2-(4-Chloro-phenyl)-4,5,6,7-tetrahydro-2H-indazol-3-yl]-2-cyclohexyl-acetylamino}-3-fluoro-phenoxy)-cyclopropanecarboxylic acid tert-butyl ester was separated by chiral preparative HPLC (Chiralpak AD column) into the stereoisomers (+)-1-(4-{2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid tert-butyl ester and (−)-1-(4-{2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid tert-butyl ester. Ee=95.7%.

Example 22

(+)-1-(4-{2-[2-(4-Chloro-phenyl)-4,5,6,7-tetrahydro-2H-indazol-3-yl]-2-cyclohexyl-acetylamino}-3-fluoro-phenoxy)-cyclopropanecarboxylic acid

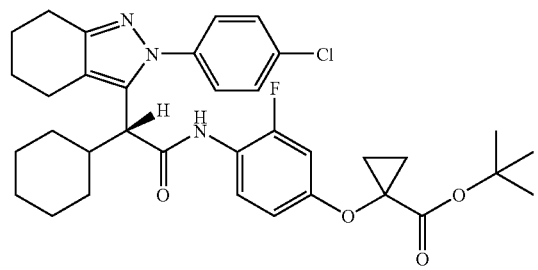

A solution of (+)-1-(4-{2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid tert-butyl ester (22 mg, 35 umol; example 21.5) in isopropanol (200 ul) and formic acid (400 ul) was stirred at 90° C. for 2 h. The mixture was poured onto ice water/brine 1/1 and extracted two times with iPrOAc. The combined extracts were washed with ice water/brine 1/1 and dried over Na$_2$SO$_4$. After filtration the solvent was removed under reduced pressure to give the title compound (20 mg, 35 umol; quant; 100% ee) as yellow foam. MS: m/e=566.3 [M+H$^+$].

Example 23

(−)-1-(4-{2-[2-(4-Chloro-phenyl)-4,5,6,7-tetrahydro-2H-indazol-3-yl]-2-cyclohexyl-acetylamino}-3-fluoro-phenoxy)-cyclopropanecarboxylic acid

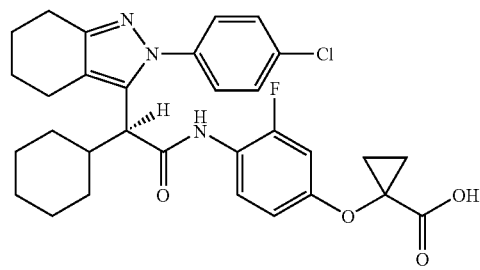

In analogy to the procedure described in example 22, (−)-1-(4-{2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid tert-butyl ester (example 21.5) was treated with formic acid to obtain the title compound as pink foam. MS: m/e=566.3 [M+H$^+$].

Example 24

[rac]-2-[2-(4-Chloro-phenyl)-5,6-difluoro-2H-indazol-3-yl]-2,N-dicyclohexyl-acetamide

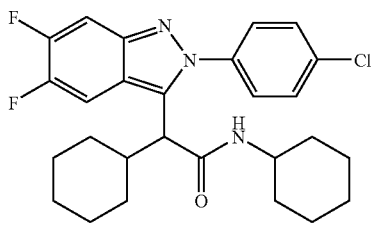

24.1 2-Azido-N-(4-chloro-phenyl)-4,5-difluoro-benzamide

A solution of 2-azido-4,5-difluoro-benzoic acid (26.2 g, 132 mmol; Grieder A.; Thomas, A. W., Synthesis (2003), (11), 1707-1711) in thionyl chloride (216 ml) was stirred under reflux conditions for 1.5 h. The solvent was removed under reduced pressure to give the corresponding crude acid chloride which was suspended in dichloromethane (200 ml). 4-Chloroaniline (16.8 g, 132 mmol) was added and the mixture was stirred at ambient temperature for 14 h. Under ice cooling saturated $NaHCO_3$ solution was added until pH 8 was reached. The mixture was extracted two times with dichloromethane, the combined extracts were washed with ice water/brine 1/1 and dried over $Na_2SO_4$. The solvent was removed under reduced pressure to give a brown solid which was crystallized from dichloromethane/n-heptane to give the title compound (18.5 g, 60 mmol; 46%) as yellow crystals.

24.2 3-Chloro-2-(4-chloro-phenyl)-5,6-difluoro-2H-indazole

2-Azido-N-(4-chloro-phenyl)-4,5-difluoro-benzamide (18.5 g, 60 mmol) was suspended in thionyl chloride (193 ml). The suspension was heated under reflux conditions for 14 h. The solvent was removed under reduced pressure. The residue was dissolved in dichloromethane. Under ice cooling saturated $NaHCO_3$ solution was added until pH 8 was reached. The mixture was extracted two times with dichloromethane, the combined extracts were washed with ice water/brine 1/1 and dried over $Na_2SO_4$. The solvent was removed under reduced pressure to give a brown solid which was crystallized from methanol/dichloromethane/n-heptane to give the title compound (16.8 g, 56 mmol; 94%) as off-white crystals. MS: m/e=299.5 [M+H$^+$].

24.3 2-(4-Chloro-phenyl)-5,6-difluoro-2H-indazole

Zinc powder (14.7 g, 225 mmol) was added to a suspension of 3-chloro-2-(4-chloro-phenyl)-5,6-difluoro-2H-indazole (16.8 g, 56 mmol) in acetic acid (118 ml). The suspension was heated under reflux conditions for 2 h. The hot solution was filtered, the filtrate was poured onto ice water/brine 1/1 and extracted two times with TBME. The combined extracts were washed with ice water/brine 1/1 and dried over $Na_2SO_4$. The solvent was removed under reduced pressure to give a brown solid which was crystallized from dichloromethane/n-heptane to give the title compound (12.1 g, 46 mmol; 81%) as brown crystals. MS: m/e=265.1 [M+H$^+$].

24.4 [rac]-[2-(4-Chloro-phenyl)-5,6-difluoro-2H-indazol-3-yl]-cyclohexyl-methanol In analogy to the procedure described in example 10.1, 2-(4-chloro-phenyl)-5,6-difluoro-2H-indazole was reacted with cyclohexane-carbaldehyde (CAS Reg. No. 2043-61-0) in the presence of n-butyllithium to give the title compound as brown oil. MS: m/e=377.3 [M+H$^+$].

24.5 [2-(4-Chloro-phenyl)-5,6-difluoro-2H-indazol-3-yl]-cyclohexyl-methanone In analogy to the procedure described in example 10.2, [rac]-[2-(4-chloro-phenyl)-5,6-difluoro-2H-indazol-3-yl]-cyclohexyl-methanol was reacted with 2-iodoxybenzoic acid in THF/DMSO 1/1 to give the title compound as yellow solid. MS: m/e=375.2 [M+H$^+$].

24.6 [rac]-[2-(4-Chloro-phenyl)-5,6-difluoro-2H-indazol-3-yl]-cyclohexyl-trimethylsilanyloxy-acetonitrile In analogy to the procedure described in example 10.3, [2-(4-chloro-phenyl)-5,6-difluoro-2H-indazol-3-yl]-cyclohexyl-methanone was treated with trimethylsilyl cyanide and zinc(II) iodide in triethylamine to give the title compound as yellow solid. MS: m/e=474.2 [M+H$^+$].

24.7 [rac]-[2-(4-Chloro-phenyl)-5,6-difluoro-2H-indazol-3-yl]-cyclohexyl-acetic acid In analogy to the procedure described in example 10.4, [rac]-[2-(4-chloro-phenyl)-5,6-difluoro-2H-indazol-3-yl]-cyclohexyl-trimethylsilanyloxy-acetonitrile was treated with tin (II) chloride in acetic acid and 25% aqueous HCl solution to give the title compound as off-white solid. MS: m/e=403.2 [M−H$^-$].

24.8 [rac]-2-[2-(4-Chloro-phenyl)-5,6-difluoro-2H-indazol-3-yl]-2,N-dicyclohexyl-acetamide In analogy to the procedure described in example 6, [rac]-[2-(4-chloro-phenyl)-5,6-difluoro-2H-indazol-3-yl]-cyclohexyl-acetic acid was converted into the corresponding acid chloride with thionyl chloride which subsequently reacted with cyclohexylamine (CAS Reg. No. 108-91-8) in the presence of DMAP to give the title compound as off-white solid. MS: m/e=486.4 [M+H$^+$].

Example 25

[rac]-2-(4-{2-[2-(4-Chloro-phenyl)-5,6-difluoro-2H-indazol-3-yl]-2-cyclohexyl-acetylamino}-3-fluoro-phenoxy)-2-methyl-propionic acid ethyl ester

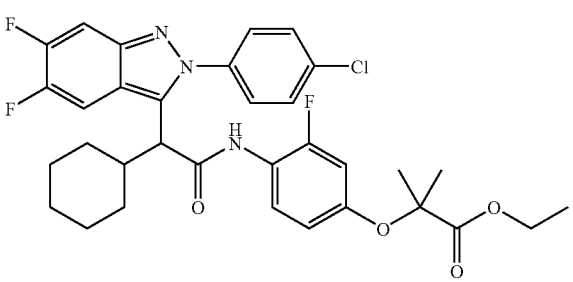

25.1
2-(3-Fluoro-4-nitro-phenoxy)-2-methyl-propionic acid ethyl ester

Potassium carbonate (3.96 g, 29 mmol) and 2-bromo-2-methylpropanoic acid ethyl ester (4.47 g, 23 mmol; CAS Reg. No. 600-00-0) were added to a solution of 3-fluoro-4-nitrophenol (3 g, 19 mmol; CAS Reg. No. 394-41-2) in DMSO (50 ml). The mixture was stirred for 18 h at 100° C. 10% aqueous citric acid and EtOAc were added and the layers were separated. The organic layer was washed with brine and dried over MgSO$_4$. The solid was filtered off and the filtrate concentrated under reduced pressure. The residue was purified by column chromatography (silica gel, EtOAc/heptane) to obtain the title compound (1.19 g, 4.4 mmol; 23%) as yellow oil.

25.2
2-(4-Amino-3-fluoro-phenoxy)-2-methyl-propionic acid ethyl ester

10% Palladium on carbon (200 mg) was added to a solution of 2-(3-fluoro-4-nitro-phenoxy)-2-methyl-propionic acid ethyl ester (1.15 g, 4 mmol) in ethanol (20 ml). The suspension was hydrogenated at a hydrogen gas pressure of 1.7 bar for 8 h at ambient temperature. Ethyl acetate was added (100 ml), the solid was filtered off and the filtrate was brought to dryness under reduced pressure to give the title compound (1.23 g, quant.) which was used in the next step without further purification.

25.3 [rac]-2-(4-{2-[2-(4-Chloro-phenyl)-5,6-difluoro-2H-indazol-3-yl]-2-cyclohexyl-acetylamino}-3-fluoro-phenoxy)-2-methyl-propionic acid ethyl ester In analogy to the procedure described in example 6, [rac]-[2-(4-chloro-phenyl)-5,6-difluoro-2H-indazol-3-yl]-cyclohexyl-acetic acid (example 24.7) was converted into the corresponding acid chloride with thionyl chloride which subsequently reacted with 2-(4-amino-3-fluoro-phenoxy)-2-methyl-propionic acid ethyl ester in the presence of DMAP to give the title compound as brown solid. MS: m/e=628.3 [M+H$^+$].

Example 26

[rac]-2-(4-{2-[2-(4-Chloro-phenyl)-5,6-difluoro-2H-indazol-3-yl]-2-cyclohexyl-acetylamino}-3-fluoro-phenoxy)-2-methyl-propionic acid

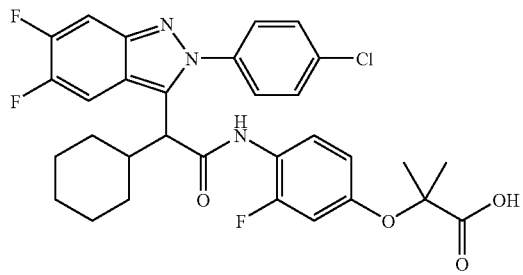

In analogy to the procedure described in example 7.2, [rac]-2-(4-{2-[2-(4-chloro-phenyl)-5,6-difluoro-2H-indazol-3-yl]-2-cyclohexyl-acetylamino}-3-fluoro-phenoxy)-2-methyl-propionic acid ethyl ester was treated with 1 N aqueous lithium hydroxide solution in THF and MeOH to give the title compound as red solid. MS: m/e=600.2 [M+H$^+$].

Example 27

[rac]-4-{[2-(4-Chloro-phenyl)-5,6-difluoro-2H-indazol-3-yl]-cyclohexyl-methoxymethyl}-benzoic acid

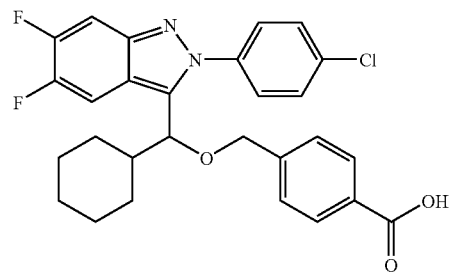

27.1 [rac]-4-{[2-(4-Chloro-phenyl)-5,6-difluoro-2H-indazol-3-yl]-cyclohexyl-methoxymethyl}-benzoic acid ethyl ester In analogy to the procedure described in example 17, [rac]-[2-(4-chloro-phenyl)-5,6-difluoro-2H-indazol-3-yl]-cyclohexyl-methanol was reacted with ethyl-4-(bromomethyl)benzoate (CAS Reg. No. 26496-94-6) in the presence of sodium hydride in DMF to give the title compound as yellow oil. MS: m/e=539.4 [M+H$^+$].

27.2 [rac]-4-{[2-(4-Chloro-phenyl)-5,6-difluoro-2H-indazol-3-yl]-cyclohexyl-methoxymethyl}-benzoic acid In analogy to the procedure described in example 7.2, [rac]-4-{[2-(4-chloro-phenyl)-5,6-difluoro-2H-indazol-3-yl]-cyclohexyl-methoxymethyl}-benzoic acid ethyl ester was treated with 1 N aqueous lithium hydroxide solution in THF and MeOH to give the title compound as colorless foam. MS: m/e=511.3 [M+H$^+$].

Example 28

[rac]-4-{[2-(4-Chloro-phenyl)-4,5,6,7-tetrahydro-2H-indazol-3-yl]-cyclohexyl-methoxymethyl}-benzoic acid

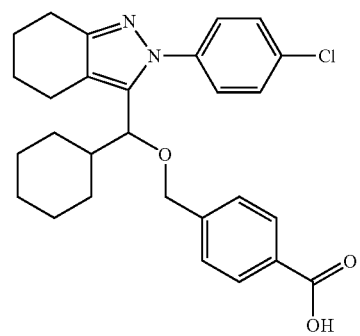

28.1 [rac]-[2-(4-Chloro-phenyl)-4,5,6,7-tetrahydro-2H-indazol-3-yl]-cyclohexyl-methanol In analogy to the procedure described in example 10.1, 2-(4-chloro-phenyl)-4,5,6,7-tetrahydro-2H-indazole (Lyga, John W.; Patera, Russell M.; Plummer, Marjorie J.; Halling, Blaik P.; Yuhas, Debra A. Pesticide Science (1994), 42(1), 29-36) was reacted with cyclohexane-carbaldehyde (CAS Reg. No. 2043-61-0) in the presence of n-butyllithium and N,N'-diisopropylethylamine to give the title compound as yellow solid. MS: m/e=345.2 [M+H$^+$].

28.2 [rac]-4-{[2-(4-Chloro-phenyl)-4,5,6,7-tetrahydro-2H-indazol-3-yl]-cyclohexyl-methoxymethyl}-benzoic acid ethyl ester In analogy to the procedure described in example 17, [rac]-[2-(4-chloro-phenyl)-4,5,6,7-tetrahydro-2H-indazol-3-yl]-cyclohexyl-methanol was reacted with ethyl-4-(bromomethyl)benzoate (CAS Reg. No. 26496-94-6) in the presence of sodium hydride in DMF to give the title compound as off-white solid. MS: m/e=507.3 [M+H$^+$].

28.3 [rac]-4-{[2-(4-Chloro-phenyl)-4,5,6,7-tetrahydro-2H-indazol-3-yl]-cyclohexyl-methoxymethyl}-benzoic acid In analogy to the procedure described in example 7.2, [rac]-4-{[2-(4-chloro-phenyl)-4,5,6,7-tetrahydro-2H-indazol-3-yl]-cyclohexyl-methoxymethyl}-benzoic acid ethyl ester was treated with 1 N aqueous lithium hydroxide solution in THF and MeOH to give the title compound as off-white solid. MS: m/e=479.3 [M+H$^+$].

Example 29

[rac]-4-{2-[2-(4-Chloro-phenyl)-2H-indazol-3-yl]-2-cyclohexyl-ethoxy}-3,5-dimethyl-benzoic acid

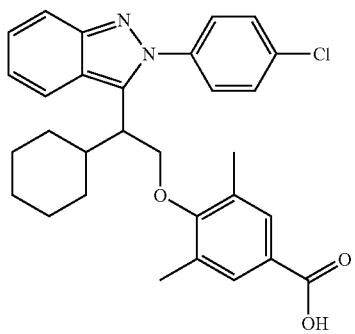

29.1 2-[2-(4-Chloro-phenyl)-2H-indazol-3-yl]-2-cyclohexyl-ethanol

Borane-tetrahydrofuran complex (680 ul, 680 umol; 1 M solution in THF) was added to an ice cold solution of [rac]-[2-(4-chloro-phenyl)-2H-indazol-3-yl]-cyclohexyl-acetic acid (100 mg, 270 umol; example 4.5) in THF (1 ml). The solution was stirred at ambient temperature for 14 h. The solvent was removed under reduced pressure and the residue purified by preparative thin layer chromatography (silica gel, iPrOAc/heptane) to obtain the title compound (56 mg, 160 umol; 58%) as colorless foam. MS: m/e=355.3 [M+H$^+$].

29.2 [rac]-4-{2-[2-(4-Chloro-phenyl)-2H-indazol-3-yl]-2-cyclohexyl-ethoxy}-3,5-dimethyl-benzoic acid methyl ester To a solution of 2-[2-(4-chloro-phenyl)-2H-indazol-3-yl]-2-cyclohexyl-ethanol (20 mg, 56 umol) in THF (1 ml) was added 4-hydroxy-3,5-dimethyl-benzoic acid methyl ester (11 mg, 62 umol; CAS Reg. No. 34137-14-9) and tri-phenylphosphine (18 mg, 68 umol) at ambient temperature under an argon atmosphere. The mixture was cooled to 0° C., di-tert-butyl azodicarboxylate (16 mg, 68 umol) was added and the suspension was stirred for 14 h at ambient temperature. The solvent was removed under reduced pressure to give a solid which was purified by column chromatography (silica gel, iPrOAc/heptane) to obtain the title compound (8 mg, 15 umol; 27%) as colorless oil. MS: m/e=517.3 [M+H$^+$].

29.3 [rac]-4-{2-[2-(4-Chloro-phenyl)-2H-indazol-3-yl]-2-cyclohexyl-ethoxy}-3,5-dimethyl-benzoic acid In analogy to the procedure described in example 7.2, [rac]-4-{2-[2-(4-chloro-phenyl)-2H-indazol-3-yl]-2-cyclohexyl-ethoxy}-3,5-dimethyl-benzoic acid methyl ester was treated with 1 N aqueous lithium hydroxide solution in THF and MeOH to give the title compound as colorless foam. MS: m/e=503.2 [M+H$^+$].

Example 30

[rac]-4-{2-[2-(4-Chloro-phenyl)-2H-indazol-3-yl]-2-cyclohexyl-ethoxy}-3-fluoro-benzonitrile

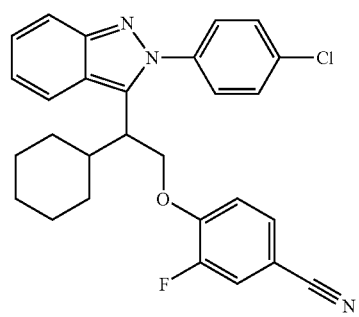

In analogy to the procedure described in example 29.2, 2-[2-(4-chloro-phenyl)-2H-indazol-3-yl]-2-cyclohexyl-ethanol (example 29.1) was reacted with 3-fluoro-4-hydroxy-benzonitrile (CAS Reg. No. 405-04-9) in the presence of tri-phenylphosphine and di-tert-butyl azodicarboxylate in THF at ambient temperature to give the title compound as colorless foam. MS: m/e=474.2 [M+H$^+$].

Example 31

[rac]-2-(4-Chloro-phenyl)-3-{1-cyclohexyl-2-[2-fluoro-4-(2H-tetrazol-5-yl)-phenoxy]-ethyl}-2H-indazole

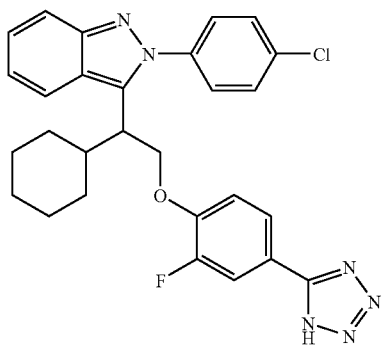

Sodium azide (14 mg, 215 umol) and triethylamine hydrochloride (29 mg, 215 umol) were added to a solution of [rac]-4-{2-[2-(4-chloro-phenyl)-2H-indazol-3-yl]-2-cyclohexyl-ethoxy}-3-fluoro-benzonitrile (20 mg, 43 umol; example 30) in DMF (0.4 ml). The solution was stirred at 120° C. for 14 h, poured onto ice water/1 N aqueous HCl solution 1/1 and extracted two times with iPrOAc. The combined extracts were washed with ice water/brine 1/1 and dried over $Na_2SO_4$. The solvent was removed under reduced pressure to give a solid which was crystallized from acetonitrile to obtain the title compound (8 mg, 16 umol; 37%) as off-white solid. MS: m/e=518.0 [M+H$^+$].

Example 32

[rac]-4-{2-[2-(4-Chloro-phenyl)-5,6-difluoro-2H-indazol-3-yl]-2-cyclohexyl-acetylamino}-3-fluoro-benzoic acid

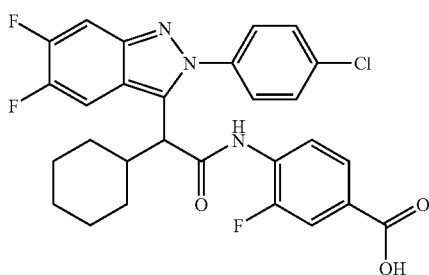

32.1 [rac]-4-{2-[2-(4-Chloro-phenyl)-5,6-difluoro-2H-indazol-3-yl]-2-cyclohexyl-acetylamino}-3-fluoro-benzoic acid ethyl ester In analogy to the procedure described in example 6, [rac]-[2-(4-chloro-phenyl)-5,6-difluoro-2H-indazol-3-yl]-cyclohexyl-acetic acid (example 24.7) was converted into the corresponding acid chloride with thionyl chloride which subsequently reacted with 4-amino-3-fluoro-benzoic acid ethyl ester (CAS Reg. No. 73792-12-8) in the presence of DMAP to give the title compound as yellow liquid. MS: m/e=570.2 [M+H$^+$].

32.2 [rac]-4-{2-[2-(4-Chloro-phenyl)-5,6-difluoro-2H-indazol-3-yl]-2-cyclohexyl-acetylamino}-3-fluoro-benzoic acid In analogy to the procedure described in example 7.2, [rac]-4-{2-[2-(4-chloro-phenyl)-5,6-difluoro-2H-indazol-3-yl]-2-cyclohexyl-acetylamino}-3-fluoro-benzoic acid ethyl ester was treated with 1 N aqueous lithium hydroxide solution in THF and MeOH to give the title compound as colorless oil. MS: m/e=542.3 [M+H$^+$].

Example 33

[rac]-4-{[2-(4-Chloro-phenyl)-5,6-difluoro-2H-indazol-3-yl]-cyclohexyl-methoxy}-3,5-dimethyl-benzoic acid methyl ester

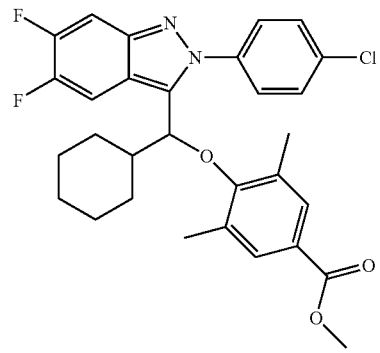

In analogy to the procedure described in example 29.2, [rac]-[2-(4-chloro-phenyl)-5,6-difluoro-2H-indazol-3-yl]-cyclohexyl-methanol (example 24.4) was reacted with 4-hydroxy-3,5-dimethyl-benzoic acid methyl ester (CAS Reg. No. 34137-14-9) in the presence of tri-phenylphosphine and di-tert-butyl azodicarboxylate in THF to give the title compound as yellow liquid. MS: m/e=539.3 [M+H$^+$].

Example 34

[rac]-4-{[2-(4-Chloro-phenyl)-5,6-difluoro-2H-indazol-3-yl]-cyclohexyl-methoxy}-3,5-dimethyl-benzoic acid

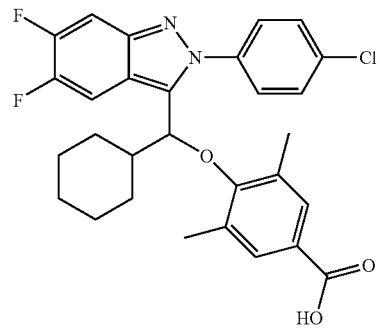

In analogy to the procedure described in example 7.2, [rac]-4-{[2-(4-chloro-phenyl)-5,6-difluoro-2H-indazol-3-yl]-cyclohexyl-methoxy}-3,5-dimethyl-benzoic acid methyl ester (example 33) was treated with 1 N aqueous lithium hydroxide solution in THF and MeOH to give the title compound as yellow foam. MS: m/e=523.3 [M−H⁻].

Example 35

[rac]-4-{[2-(4-Chloro-phenyl)-5,6-difluoro-2H-indazol-3-yl]-cyclohexyl-methoxy}-3-fluoro-benzonitrile

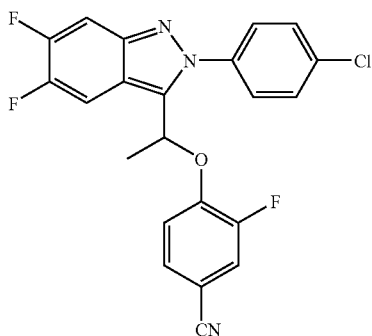

In analogy to the procedure described in example 29.2, [rac]-[2-(4-chloro-phenyl)-5,6-difluoro-2H-indazol-3-yl]-cyclohexyl-methanol (example 24.4) was reacted with 3-fluoro-4-hydroxy-benzonitrile (CAS Reg. No. 405-04-9) in the presence of tri-phenylphosphine and di-tert-butyl azodicarboxylate in THF to give the title compound as yellow solid. MS: m/e=496.1 [M+H⁺].

Example 36

[rac]-2-(4-Chloro-phenyl)-3-{1-cyclohexyl-2-[2-fluoro-4-(2H-tetrazol-5-yl)-phenoxy]-ethyl}-5,6-difluoro-2H-indazole

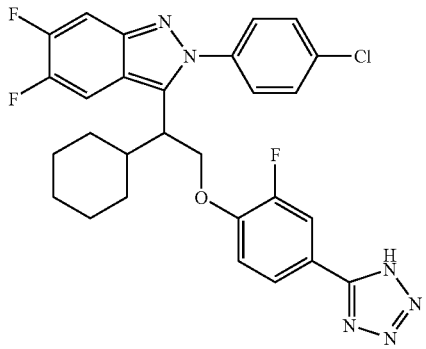

36.1 [rac]-2-[2-(4-Chloro-phenyl)-5,6-difluoro-2H-indazol-3-yl]-2-cyclohexyl-ethanol In analogy to the procedure described in example 29.1, [rac]-[2-(4-chloro-phenyl)-5,6-difluoro-2H-indazol-3-yl]-cyclohexyl-acetic acid (example 24.7) was reduced using borane-tetrahydrofuran complex in THF to give the title compound as off-white foam. MS: m/e=391.1 [M+H⁺].

36.2 [rac]-4-{2-[2-(4-Chloro-phenyl)-5,6-difluoro-2H-indazol-3-yl]-2-cyclohexyl-ethoxy}-3-fluoro-benzonitrile In analogy to the procedure described in example 29.2, [rac]-2-[2-(4-chloro-phenyl)-5,6-difluoro-2H-indazol-3-yl]-2-cyclohexyl-ethanol was reacted with 3-fluoro-4-hydroxy-benzonitrile (CAS Reg. No. 405-04-9) in the presence of tri-phenylphosphine and di-tert-butyl azodicarboxylate in THF to give the title compound as yellow oil. MS: m/e=510.3 [M+H⁺].

36.3 [rac]-2-(4-Chloro-phenyl)-3-{1-cyclohexyl-2-[2-fluoro-4-(2H-tetrazol-5-yl)-phenoxy]-ethyl}-5,6-difluoro-2H-indazole In analogy to the procedure described in example 31, [rac]-4-{2-[2-(4-Chloro-phenyl)-5,6-difluoro-2H-indazol-3-yl]-2-cyclohexyl-ethoxy}-3-fluoro-benzonitrile was reacted with sodium azide in the presence of triethylamine hydrochloride in DMF to obtain the title compound as colorless oil. MS: m/e=553.3 [M+H⁺].

Example 37

[rac]-4-{2-[2-(4-Chloro-phenyl)-4,5,6,7-tetrahydro-2H-indazol-3-yl]-2-cyclohexyl-ethoxy}-3-fluoro-benzonitrile

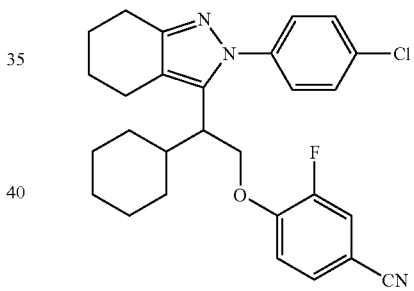

37.1 [rac]-2-[2-(4-Chloro-phenyl)-4,5,6,7-tetrahydro-2H-indazol-3-yl]-2-cyclohexyl-ethanol In analogy to the procedure described in example 29.1, [rac]-[2-(4-chloro-phenyl)-4,5,6,7-tetrahydro-2H-indazol-3-yl]-cyclohexyl-acetic acid (example 5.1) was reduced using borane-tetrahydrofuran complex in THF to give the title compound as off-white solid. MS: m/e=359.2 [M+H⁺].

37.2 [rac]-4-{2-[2-(4-Chloro-phenyl)-4,5,6,7-tetrahydro-2H-indazol-3-yl]-2-cyclohexyl-ethoxy}-3-fluoro-benzonitrile In analogy to the procedure described in example 29.2, [rac]-2-[2-(4-chloro-phenyl)-4,5,6,7-tetrahydro-2H-indazol-3-yl]-2-cyclohexyl-ethanol was reacted with 3-fluoro-4-hydroxy-benzonitrile (CAS Reg. No. 405-04-9) in the presence of tri-phenylphosphine and di-tert-butyl azodicarboxylate in THF to give the title compound as white solid. MS: m/e=478.2 [M+H⁺].

Example 38

[rac]-2-(4-Chloro-phenyl)-3-{1-cyclohexyl-2-[2-fluoro-4-(1H-tetrazol-5-yl)-phenoxy]-ethyl}-4,5,6,7-tetrahydro-2H-indazole

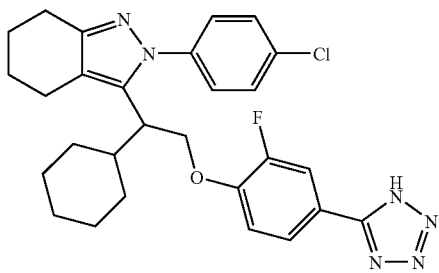

In analogy to the procedure described in example 31, [rac]-4-{2-[2-(4-chloro-phenyl)-4,5,6,7-tetrahydro-2H-indazol-3-yl]-2-cyclohexyl-ethoxy}-3-fluoro-benzonitrile (example 37.2) was reacted with sodium azide in the presence of triethylamine hydrochloride in DMF to obtain the title compound as off-white solid. MS: m/e=521.3 [M+H$^+$].

Example 39

[rac]-4-{2-[2-(4-Chloro-phenyl)-4,5,6,7-tetrahydro-2H-indazol-3-yl]-2-cyclohexyl-ethoxy}-3,5-dimethyl-benzoic acid methyl ester

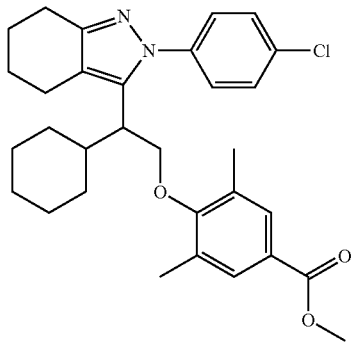

In analogy to the procedure described in example 29.2, [rac]-2-[2-(4-chloro-phenyl)-4,5,6,7-tetrahydro-2H-indazol-3-yl]-2-cyclohexyl-ethanol (example 37.1) was reacted with 4-hydroxy-3,5-dimethyl-benzoic acid methyl ester (CAS Reg. No. 34137-14-9) in the presence of tri-phenylphosphine and di-tert-butyl azodicarboxylate in THF to give the title compound as white solid. MS: m/e=521.3 [M+H$^+$].

Example 40

[rac]-4-{2-[2-(4-Chloro-phenyl)-4,5,6,7-tetrahydro-2H-indazol-3-yl]-2-cyclohexyl-ethoxy}-3,5-dimethyl-benzoic acid

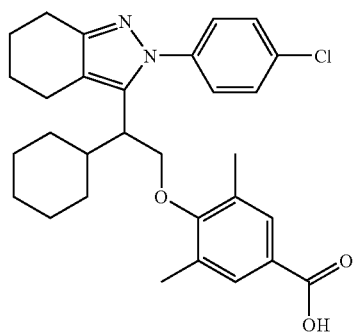

In analogy to the procedure described in example 7.2, [rac]-4-{2-[2-(4-chloro-phenyl)-4,5,6,7-tetrahydro-2H-indazol-3-yl]-2-cyclohexyl-ethoxy}-3,5-dimethyl-benzoic acid methyl ester (example 39) was treated with 1 N aqueous lithium hydroxide solution in THF and MeOH to give the title compound as off-white solid. MS: m/e=507.2 [M+H$^+$].

Example 41

[rac]-4-{[2-(4-Chloro-phenyl)-5,6-difluoro-2H-indazol-3-yl]-cyclohexyl-methoxymethyl}-3-fluoro-benzonitrile

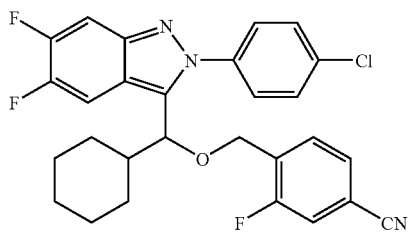

In analogy to the procedure described in example 17, [rac]-[2-(4-chloro-phenyl)-5,6-difluoro-2H-indazol-3-yl]-cyclohexyl-methanol (example 24.4) was reacted with 4-cyano-2-fluorobenzyl bromide (CAS Reg. No. 105942-09-4) in the presence of sodium hydride in DMF to give the title compound as yellow foam. MS: m/e=510.3 [M+H$^+$].

Example 42

[rac]-2-(4-Chloro-phenyl)-3-{cyclohexyl-[2-fluoro-4-(2H-tetrazol-5-yl)-benzyloxy]-methyl}-5,6-difluoro-2H-indazole

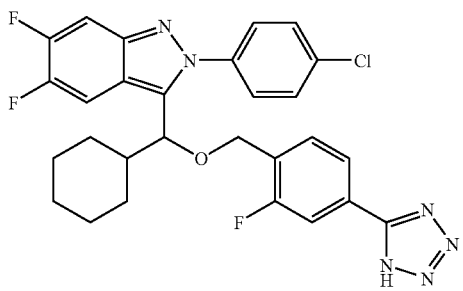

In analogy to the procedure described in example 31, [rac]-4-{[2-(4-chloro-phenyl)-5,6-difluoro-2H-indazol-3-yl]-cyclohexyl-methoxymethyl}-3-fluoro-benzonitrile (example 41) was reacted with sodium azide in the presence of triethylamine hydrochloride in DMF to obtain the title compound as yellow foam. MS: m/e=553.2 [M+H$^+$].

Example 43

[rac]-4-{2-[2-[4-Chloro-phenyl]-5,6-difluoro-2H-indazol-3-yl]-2-cyclohexyl-ethoxy}-3,5-dimethyl-benzoic acid

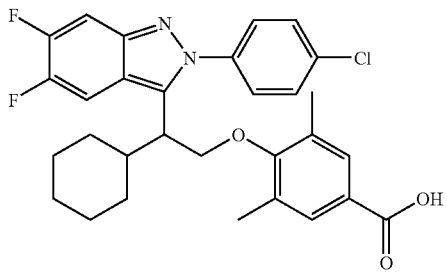

43.1 [rac]-4-{2-[2-(4-Chloro-phenyl)-5,6-difluoro-2H-indazol-3-yl]-2-cyclohexyl-ethoxy}-3,5-dimethyl-benzoic acid methyl ester In analogy to the procedure described in example 29.2, [rac]-2-[2-(4-chloro-phenyl)-5,6-difluoro-2H-indazol-3-yl]-2-cyclohexyl-ethanol (example 36.1) was reacted with 4-hydroxy-3,5-dimethyl-benzoic acid methyl ester (CAS Reg. No. 34137-14-9) in the presence of tri-phenylphosphine and di-tert-butyl azodicarboxylate in THF to give the title compound as yellow oil. MS: m/e=553.4 [M+H$^+$].

43.2 [rac]-4-{2-[2-(4-Chloro-phenyl)-5,6-difluoro-2H-indazol-3-yl]-2-cyclohexyl-ethoxy}-3,5-dimethyl-benzoic acid In analogy to the procedure described in example 7.2, [rac]-4-{2-[2-(4-chloro-phenyl)-5,6-difluoro-2H-indazol-3-yl]-2-cyclohexyl-ethoxy}-3,5-dimethyl-benzoic acid methyl ester was treated with 1 N aqueous lithium hydroxide solution in THF and MeOH to give the title compound as off-white solid. MS: m/e=539.3 [M+H$^+$].

Example 44

[rac]-4-{[2-(4-Chloro-phenyl)-4,5,6,7-tetrahydro-2H-indazol-3-yl]-cyclohexyl-methoxymethyl}-benzonitrile

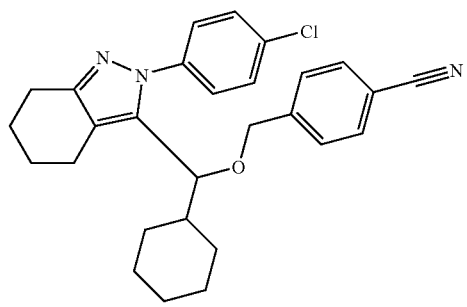

In analogy to the procedure described in example 17, [rac]-[2-(4-chloro-phenyl)-4,5,6,7-tetrahydro-2H-indazol-3-yl]-cyclohexyl-methanol (example 28.1) was reacted with 4-cyanobenzyl bromide (CAS Reg. No. 17201-43-3) in the presence of sodium hydride in DMF to give the title compound as colorless oil. MS: m/e=460.3 [M+H$^+$].

Example 45

[rac]-4-{[2-(4-Chloro-phenyl)-2H-indazol-3-yl]-cyclohexyl-methoxymethyl}-3-fluoro-benzonitrile

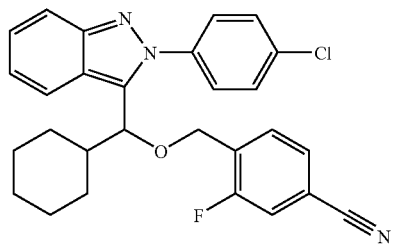

In analogy to the procedure described in example 17, [rac]-[2-(4-chloro-phenyl)-2H-indazol-3-yl]-cyclohexyl-methanol (example 10.1) was reacted with 4-cyano-2-fluorobenzyl bromide (CAS Reg. No. 105942-09-4) in the presence of sodium hydride in DMF to give the title compound as brown oil. MS: m/e=474.2 [M+H$^+$].

Example 46

[rac]-4-{[2-(4-Chloro-phenyl)-2H-indazol-3-yl]-cyclohexyl-methoxymethyl}-benzonitrile

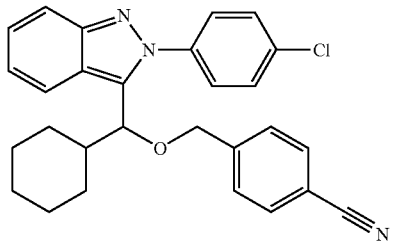

In analogy to the procedure described in example 17, [rac]-[2-(4-chloro-phenyl)-2H-indazol-3-yl]-cyclohexyl-methanol (example 10.1) was reacted with 4-cyanobenzyl bromide (CAS Reg. No. 17201-43-3) in the presence of sodium hydride in DMF to give the title compound as yellow foam. MS: m/e=456.2 [M+H$^+$].

Example 47

[rac]-2-(4-Chloro-phenyl)-3-{cyclohexyl-[4-(2H-tetrazol-5-yl)-benzyloxy]-methyl}-2H-indazole

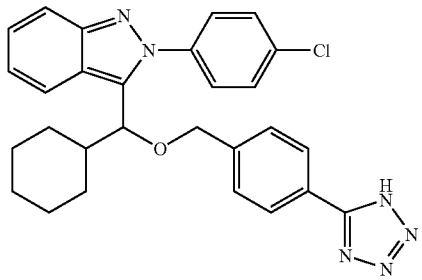

In analogy to the procedure described in example 31, [rac]-4-{[2-(4-chloro-phenyl)-2H-indazol-3-yl]-cyclohexyl-methoxymethyl}-benzonitrile (example 46) was reacted with sodium azide in the presence of triethylamine hydrochloride in DMF to obtain the title compound as brown solid. MS: m/e=499.3 [M+H$^+$].

Example 48

[rac]-4-{[2-(4-Chloro-phenyl)-5,6-difluoro-2H-indazol-3-yl]-cyclohexyl-methoxymethyl}-benzonitrile

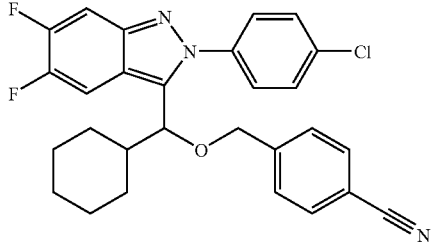

In analogy to the procedure described in example 17, [rac]-4-{[2-(4-chloro-phenyl)-5,6-difluoro-2H-indazol-3-yl]-cyclohexyl-methoxymethyl}-3-fluoro-benzonitrile (example 41) was reacted with 4-cyanobenzyl bromide (CAS Reg. No. 17201-43-3) in the presence of sodium hydride in DMF to give the title compound as yellow foam. MS: m/e=492.2 [M+H$^+$].

Example 49

[rac]-2-(4-Chloro-phenyl)-3-{cyclohexyl-[4-(2H-tetrazol-5-yl)-benzyloxy]-methyl}-5,6-difluoro-2H-indazole

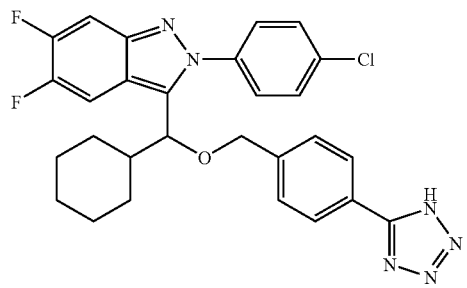

In analogy to the procedure described in example 31, [rac]-4-{[2-(4-chloro-phenyl)-5,6-difluoro-2H-indazol-3-yl]-cyclohexyl-methoxymethyl}-benzonitrile (example 48) was reacted with sodium azide in the presence of triethylamine hydrochloride in DMF to obtain the title compound as brown oil. MS: m/e=535.2 [M+H$^+$].

Example 50

[rac]-2-(4-Chloro-phenyl)-3-{cyclohexyl-[2-fluoro-4-(1H-tetrazol-5-yl)-phenoxy]-methyl}-5,6-difluoro-2H-indazole

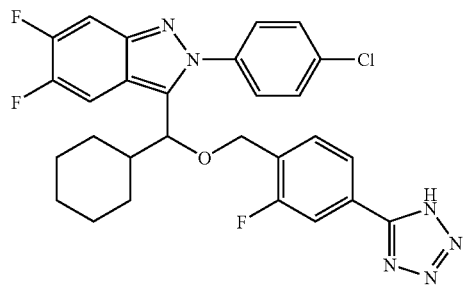

In analogy to the procedure described in example 31, [rac]-4-{[2-(4-chloro-phenyl)-5,6-difluoro-2H-indazol-3-yl]-cyclohexyl-methoxy}-3-fluoro-benzonitrile (example 35) was reacted with sodium azide in the presence of triethylamine hydrochloride in DMF to obtain the title compound as yellow solid. MS: m/e=539.2 [M+H$^+$].

Example 51

[rac]-4-{2-[2-(4-Chloro-phenyl)-2H-indazol-3-yl]-2-cyclohexyl-ethoxy}-3,5-dimethyl-benzonitrile

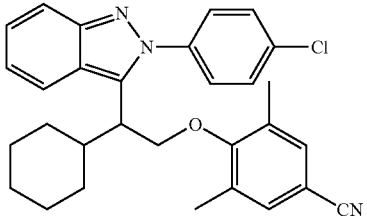

In analogy to the procedure described in example 29.2, 2-[2-(4-chloro-phenyl)-2H-indazol-3-yl]-2-cyclohexyl-ethanol (example 29.1) was reacted with 3,5-dimethyl-4-hydroxybenzonitrile (CAS Reg. No. 4198-90-7) in the presence of tri-phenylphosphine and di-tert-butyl azodicarboxylate in THF at ambient temperature to give the title compound as yellow oil. MS: m/e=484.2 [M+H$^+$].

Example 52

[rac]-2-(4-Chloro-phenyl)-3-{1-cyclohexyl-2-[2,6-dimethyl-4-(2H-tetrazol-5-yl)-phenoxy]-ethyl}-2H-indazole

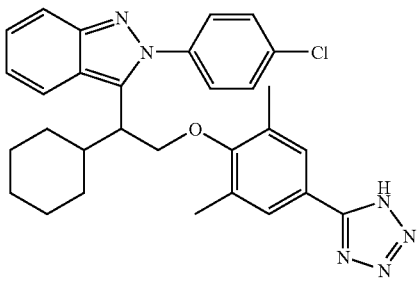

In analogy to the procedure described in example 31, [rac]-4-{2-[2-(4-chloro-phenyl)-2H-indazol-3-yl]-2-cyclohexyl-ethoxy}-3,5-dimethyl-benzonitrile (example 51) was reacted with sodium azide in the presence of triethylamine hydrochloride in DMF to obtain the title compound as brown solid. MS: m/e=527.4 [M+H$^+$].

Example 53

[rac]-6-{2-[2-(4-Chloro-phenyl)-2H-indazol-3-yl]-2-cyclohexyl-ethoxy}-nicotinic acid

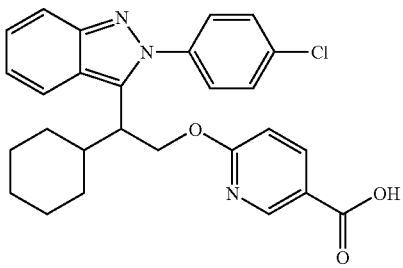

53.1 [rac]-6-{2-[2-(4-Chloro-phenyl)-2H-indazol-3-yl]-2-cyclohexyl-ethoxy}-nicotinic acid methyl ester In analogy to the procedure described in example 29.2, 2-[2-(4-chloro-phenyl)-2H-indazol-3-yl]-2-cyclohexyl-ethanol (example 29.1) was reacted with methyl 6-hydroxynicotinate (CAS Reg. No. 10128-91-3) in the presence of tri-n-butylphosphine and N,N,N',N'-tetramethylazodicarboxamide in THF at ambient temperature to give the title compound as colorless oil. MS: m/e=490.3 [M+H$^+$].

53.2 [rac]-6-{2-[2-(4-Chloro-phenyl)-2H-indazol-3-yl]-2-cyclohexyl-ethoxy}-nicotinic acid In analogy to the procedure described in example 7.2, [rac]-6-{2-[2-(4-chloro-phenyl)-2H-indazol-3-yl]-2-cyclohexyl-ethoxy}-nicotinic acid methyl ester was treated with 1 N aqueous lithium hydroxide solution in THF and MeOH to give the title compound as colorless oil. MS: m/e=476.1 [M+H$^+$].

Example 54

[rac]-1-(4-{2-[2-(4-Chloro-phenyl)-2H-indazol-3-yl]-2-cyclohexyl-ethoxy}-phenoxy)-cyclopropanecarboxylic acid methyl ester

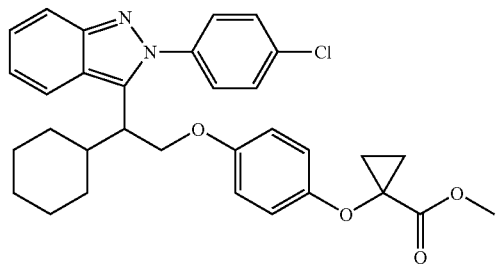

In analogy to the procedure described in example 29.2, 2-[2-(4-chloro-phenyl)-2H-indazol-3-yl]-2-cyclohexyl-ethanol (example 29.1) was reacted with 1-(4-hydroxy-phenoxy)-cyclopropanecarboxylic acid methyl ester (Hazeldine, Stuart T.; Polin, Lisa; Kushner, Juiwanna; White, Kathryn; Corbett, Thomas H.; Horwitz, Jerome P. Bioorganic & Medicinal Chemistry (2005), 13(12), 3910-3920) in the presence of tri-n-butylphosphine and N,N,N',N'-tetramethylazodicarboxamide in THF at ambient temperature to give the title compound as off-white solid. MS: m/e=545.3 [M+H$^+$].

Example 55

[rac]-1-(4-{2-[2-(4-Chloro-phenyl)-4,5,6,7-tetrahydro-2H-indazol-3-yl]-2-cyclohexyl-ethoxy}-phenoxy)-cyclopropanecarboxylic acid

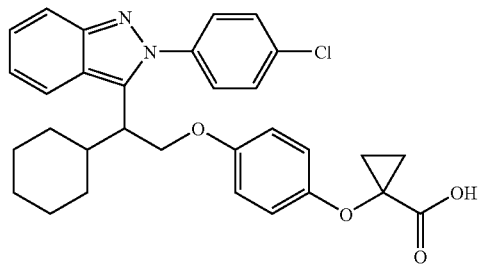

55.1 [rac]-1-(4-{2-[2-(4-Chloro-phenyl)-4,5,6,7-tetrahydro-2H-indazol-3-yl]-2-cyclohexyl-ethoxy}-phenoxy)-cyclopropanecarboxylic acid methyl ester In analogy to the procedure described in example 29.2, [rac]-2-[2-(4-chloro-phenyl)-4,5,6,7-tetrahydro-2H-indazol- 3-yl]-2-cyclohexyl-ethanol (example 37.1) was reacted with 1-(4-hydroxy-phenoxy)-cyclopropanecarboxylic acid methyl ester (Hazeldine, Stuart T.; Polin, Lisa; Kushner, Juiwanna; White, Kathryn; Corbett, Thomas H.; Horwitz, Jerome P. Bioorganic & Medicinal Chemistry (2005), 13(12), 3910-3920) in the presence of tri-n-butylphosphine and N,N,N',N'-tetramethylazodicarboxamide in THF at ambient temperature to give the title compound as white solid. MS: m/e=549.3 [M+H$^+$].

55.2 [rac]-1-(4-{2-[2-(4-Chloro-phenyl)-4,5,6,7-tetrahydro-2H-indazol-3-yl]-2-cyclohexyl-ethoxy}-phenoxy)-cyclopropanecarboxylic acid In analogy to the procedure described in example 7.2, [rac]-1-(4-{2-[2-(4-chloro-phenyl)-2H-indazol-3-yl]-2-cyclohexyl-ethoxy}-phenoxy)-cyclopropanecarboxylic acid methyl ester was treated with 1 N aqueous lithium hydroxide solution in THF and MeOH to give the title compound as yellow oil. MS: m/e=533.2 [M–H]$^{-1}$.

Example 56

[rac]-1-(4-{[2-(4-Chloro-phenyl)-5,6-difluoro-2H-indazol-3-yl]-cyclohexyl-methoxy}-phenoxy)-cyclopropanecarboxylic acid

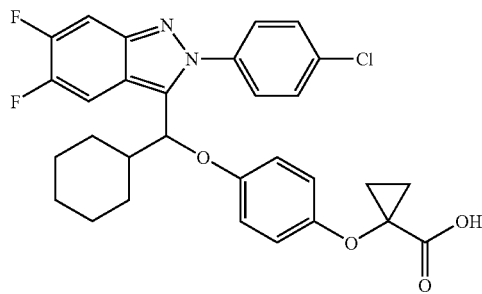

56.1 [rac]-1-(4-{[2-(4-Chloro-phenyl)-5,6-difluoro-2H-indazol-3-yl]-cyclohexyl-methoxy}-phenoxy)-cyclopropanecarboxylic acid methyl ester In analogy to the procedure described in example 29.2, [rac]-[2-(4-chloro-phenyl)-5,6-difluoro-2H-indazol-3-yl]-cyclohexyl-methanol (example 24.4) was reacted with 1-(4-hydroxy-phenoxy)-cyclopropanecarboxylic acid methyl ester (Hazeldine, Stuart T.; Polin, Lisa; Kushner, Juiwanna; White, Kathryn; Corbett, Thomas H.; Horwitz, Jerome P. Bioorganic & Medicinal Chemistry (2005), 13(12), 3910-3920) in the presence of tri-phenylphosphine and di-tert-butyl azodicarboxylate in THF to give the title compound as white solid. MS: m/e=567.4 [M+H$^+$].

56.1 [rac]-1-(4-{[2-(4-Chloro-phenyl)-5,6-difluoro-2H-indazol-3-yl]-cyclohexyl-methoxy}-phenoxy)-cyclopropanecarboxylic acid In analogy to the procedure described in example 7.2, [rac]-1-(4-{[2-(4-chloro-phenyl)-5,6-difluoro-2H-indazol-3-yl]-cyclohexyl-methoxy}-phenoxy)-cyclopropanecarboxylic acid methyl ester was treated with 1 N aqueous lithium hydroxide solution in THF and MeOH to give the title compound as colorless liquid. MS: m/e=553.3 [M+H$^+$].

Example 57

[rac]-2-[2-(4-Chloro-phenyl)-4,5,6,7-tetrahydro-2H-indazol-3-yl]-2-cyclohexyl-N[4-(1H-tetrazol-5-yl)-phenyl]-acetamide

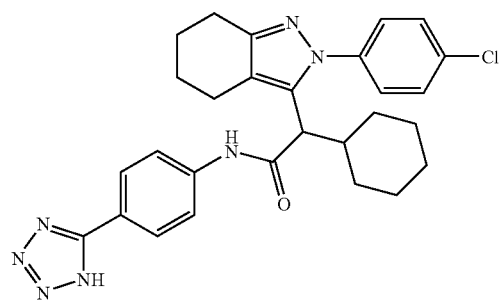

57.1 4-(1H-Tetrazol-5-yl)-phenylamine

To a stirred solution of 4-amino-benzonitrile (300 mg, 2.53 mmol; CAS Reg. No. 873-74-5) in dry DMF (6 ml) was added NH$_4$Cl (547 mg, 10.2 mmol) and NaN$_3$ (660 mg, 10.2 mmol) at room temperature. The reaction mixture was then heated at 120° C. for 12 h. After cooling, TLC shows formation of new spot, filtered the solid material by sintered funnel and washed the solid residue by EtOAc (4×5 ml). Combined organic layers were reduced under pressure at 60° C. and diluted the residue with EtOAc (25 mL). Organic layer was washed with H$_2$O (15 ml), brine (12 ml) and dried over Na$_2$SO$_4$; which was then concentrated under reduced pressure to give the crude material (300 mg). Crude product was then purified by column chromatography [SiO$_2$ (230-400 mesh), MeOH:DCM 5:95] to give the title compound (180 mg, 44.4%) as light yellow solid.

57.2 [rac]-2-[2-(4-Chloro-phenyl)-4,5,6,7-tetrahydro-2H-indazol-3-yl]-2-cyclohexyl-N[4-(1H-tetrazol-5-yl)-phenyl]-acetamide To a stirred solution of [2-(4-chloro-phenyl)-4,5,6,7-tetrahydro-2H-indazol-3-yl]-cyclohexyl-acetic acid (250 mg, 0.67 mmol; example 5.1) in dry DMF (12 mL) was added dry DIPEA (0.375 ml, 2.32 mmol) followed by HATU (510 mg, 1.34 mmol) at 0° C. Then the reaction mixture was allowed to warm to rt and stirred for 45 min at that temperature. TLC shows total consumption of acid and formation of a new spot. 4-(1H-Tetrazol-5-yl)-phenylamine (162.5 mg, 1.02 mmol) was added to this reaction mixture at 0° C. Then the cooling bath was removed and the reaction mixture was stirred at room temperature for 16 h. TLC shows total consumption of [2-(4-chloro-phenyl)-4,5,6,7-tetrahydro-2H-indazol-3-yl]-cyclohexyl-acetic acid and DMF was removed in vacuo at 50° C. It was then diluted with H$_2$O (15 ml). Aqueous layer was extracted with EtOAc (4×20 mL) and combined organic layers were washed with brine (20 ml), dried over Na$_2$SO$_4$ and concentrated in vacuo. Crude product (355.0 mg) was subjected to column chromatography [SiO$_2$ (230-400 mesh),

Example 58

[rac]-2-[2-(4-Chloro-phenyl)-4,5,6,7-tetrahydro-2H-indazol-3-yl]-2-cyclohexyl-N-[2-fluoro-4-(1H-tetrazol-5-yl)-phenyl]-acetamide

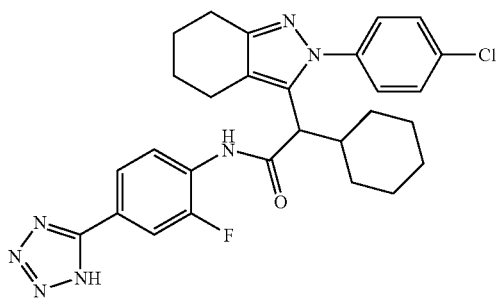

58.1 [rac]-[2-(4-Chloro-phenyl)-4,5,6,7-tetrahydro-2H-indazol-3-yl]-cyclohexyl-acetic acid methyl ester To a stirred solution of [2-(4-chloro-phenyl)-4,5,6,7-tetrahydro-2H-indazol-3-yl]-cyclohexyl-acetic acid (250 mg, 0.67 mmol; example 5.1) in dry DCM (7 mL) was added oxalyl chloride (0.14 ml, 1.67 mmol) drop wise at 0° C. followed by 1 drop DMF and the reaction mixture was stirred at that temperature for 30 min. Ice-bath was removed and stirring was continued for 3.5 h at room temperature. DCM and excess oxalyl chloride was then removed under reduced pressure and MeOH (2 ml) was then added to it at 0° C. After being stirring the reaction mixture at rt for 1 h, TLC shows formation of a new spot. MeOH was removed under vacuo and crude material was passed through a bed of silica gel (SiO$_2$, 100-200 mesh, EtOAc:hexane 30:70) to give the title compound as colorless liquid (250 mg, 95.5%).

58.2 [rac]-2-[2-(4-Chloro-phenyl)-4,5,6,7-tetrahydro-2H-indazol-3-yl]-N-(4-cyano-2-fluoro-phenyl)-2-cyclohexyl-acetamide To a stirred solution of [rac]-[2-(4-chloro-phenyl)-4,5,6,7-tetrahydro-2H-indazol-3-yl]-cyclohexyl-acetic acid methyl ester (250 mg, 0.64 mmol) in dry THF was added LiHMDS (1.0 M solution in THF; 4.5 ml, 4.5 mmol) at −30° C. and stirring continued for another 30 min at that temperature. 4-Amino-3-fluoro-benzonitrile (90.64 mg, 0.768 mmol; CAS Reg. No. 115661-37-5) in THF (1 ml) was then added at that temperature and slowly brought to room temperature. Reaction mixture was then stirred at room temperature for 13 h. TLC shows formation of a new spot. LC-MS of the crude material shows formation of desired product. Reaction mixture was quenched with saturated NH$_4$Cl and the aqueous layer was extracted with EtOAc (3×5 ml). Combined organic layers were washed with brine and concentrated under reduced pressure to give crude material (260 mg); which was then purified by column chromatography [SiO$_2$ (230-400 mesh), EtOAc:hexane 30:70] to give the title compound (130 mg, 42%) as light yellow solid.

58.3 [rac]-2-[2-(4-Chloro-phenyl)-4,5,6,7-tetrahydro-2H-indazol-3-yl]-2-cyclohexyl-N-[2-fluoro-4-(1H-tetrazol-5-yl)-phenyl]-acetamide To a stirred solution of [rac]-2-[2-(4-chloro-phenyl)-4,5,6,7-tetrahydro-2H-indazol-3-yl]-N-(4-cyano-2-fluoro-phenyl)-2-cyclohexyl-acetamide (110 mg, 0.22 mmol) in dry DMF (3 ml) was added NH$_4$Cl (48.39 mg, 0.88 mmol) and NaN$_3$ (57.2 mg, 0.88 mmol) at room temperature. The reaction mixture was then heated at 120° C. for 12 h. After cooling, TLC shows formation of new spot, filtered the solid material by sintered funnel and washed the solid residue by EtOAc (3×5 ml). Combined organic layers were reduced under pressure at 50° C. and diluted the residue with EtOAc (15 mL). Organic layer was washed with H$_2$O (10 ml), brine (10 ml) and dried over Na$_2$SO$_4$; which was then concentrated under reduced pressure to give crude material (90 mg). Crude product was then purified by column chromatography [SiO$_2$ (230-400 mesh), MeOH:DCM 0:95/5:95] to give the title compound (40 mg, 33.3%) as brown solid. MS: m/e=534.0 [M+H$^+$].

Example 59

[rac]-2-[2-(4-Chloro-phenyl)-4,5,6,7-tetrahydro-2H-indazol-3-yl]-2-cyclohexyl-(trans)-N-(4-hydroxy-cyclohexyl)-acetamide

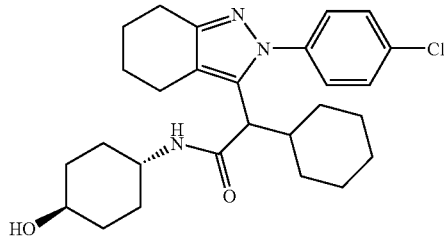

To a stirred solution of [2-(4-chloro-phenyl)-4,5,6,7-tetrahydro-2H-indazol-3-yl]-cyclohexyl-acetic acid (200 mg, 0.54 mmol; example 5.1) in dry DMF (4 mL) was added dry DIPEA (3.2 mmol) followed by HATU (1.6 mmol) at 0° C. Then the reaction mixture was allowed to warm to rt and stirred for 45 min at that temperature. TLC shows total consumption of acid and formation of a new spot. (trans)-4-Amino-cyclohexanol (0.64 mmol) was added to this reaction mixture at 0° C. Then the cooling bath was removed and the reaction mixture was stirred at room temperature for 16 h. TLC shows total consumption of [2-(4-chloro-phenyl)-4,5,6,7-tetrahydro-2H-indazol-3-yl]-cyclohexyl-acetic acid and DMF was removed in vacuo at 60° C. It was then diluted with H$_2$O (5 ml). Aqueous layer was extracted with EtOAc (5×5 mL) and combined organic layers were washed with brine (50 ml), dried over Na$_2$SO$_4$ and concentrated in vacuo. Crude product was subjected to column chromatography [SiO$_2$ (230-400 mesh), EtOAc:Hexane 10:90] to give the title compound (40 mg, 24%) as off-white solid. MS: m/e=470.0 [M+H$^+$].

Example 60

[rac]-(4-{2-[2-(4-Chloro-phenyl)-4,5,6,7-tetrahydro-2H-indazol-3-yl]-2-cyclohexyl-(trans)-acetylamino}-cyclohexyl)-acetic acid

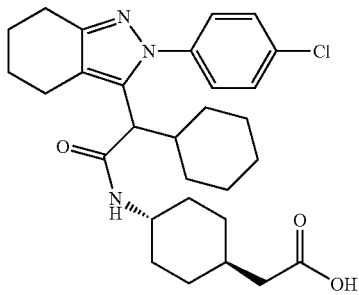

60.1 [rac]-(4-{2-[2-(4-Chloro-phenyl)-4,5,6,7-tetrahydro-2H-indazol-3-yl]-2-cyclohexyl-(trans)-acetylamino}-cyclohexyl)-acetic acid ethyl ester In analogy to the procedure described in example 59, [2-(4-chloro-phenyl)-4,5,6,7-tetrahydro-2H-indazol-3-yl]-cyclohexyl-acetic acid (example 5.1) was reacted with (trans)-(4-amino-cyclohexyl)-acetic acid ethyl ester (Gobbi, Luca; Jaeschke, Georg; Luebbers, Thomas; Roche, Olivier; Rodriguez Sarmiento, Rosa Maria; Steward, Lucinda. PCT Int. Appl. (2007), WO 2007093540) in the presence of DIPEA and HATU in DMF to give the title compound yellow solid.

60.2 [rac]-(4-{2-[2-(4-Chloro-phenyl)-4,5,6,7-tetrahydro-2H-indazol-3-yl]-2-cyclohexyl-(trans)-acetylamino}-cyclohexyl)-acetic acid To a solution of [rac]-(4-{2-[2-(4-chloro-phenyl)-4,5,6,7-tetrahydro-2H-indazol-3-yl]-2-cyclohexyl-(trans)-acetylamino}-cyclohexyl)-acetic acid ethyl ester (30 mg, 0.05 mmol) in THF (4.0 ml) was added LiOH (6.0 mg, 0.13 mmol) in $H_2O$ (1 ml) at 0° C. and the reaction mixture was stirred at room temperature for 14 hours. After the completion of the reaction (monitored through TLC), solvent was concentrated in vacuo. It was then diluted with $H_2O$ (5 ml) and the aqueous layer was washed with $Et_2O$ (2×5 ml). Aqueous layer was acidified (pH~2-3) with 2N HCl and then extracted with EtOAc (2×10 ml). Combined organic layers were washed with brine (5 mL) and dried over $Na_2SO_4$. Organic layer was evaporated under reduced pressure to give the title compound (25 mg; 87%) as colorless sticky material. MS: m/e=512.0 [M+H$^+$].

Example 61

[rac]-3-(4-{2-[2-(4-Chloro-phenyl)-4,5,6,7-tetrahydro-2H-indazol-3-yl]-2-cyclohexyl-acetylamino}-3-fluoro-phenyl)-propionic acid

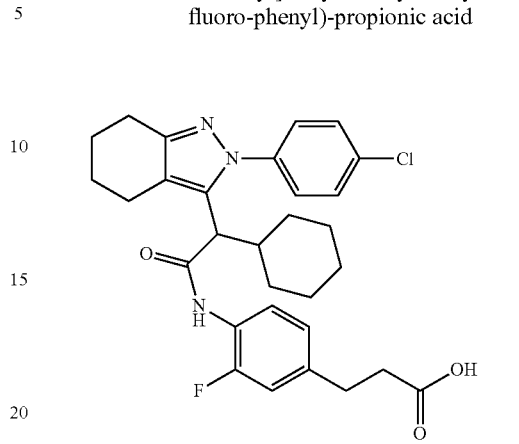

61.1 (E)-3-(3-fluoro-4-nitro-phenyl)-acrylic acid tert-butyl ester

Potassium tert-butylate (0.438 g, 3.9 mmol) was added to a suspension of tert-butoxy carbonyl methyl triphenyl phosphonium bromide (1.61 g, 3.9 mmol; CAS Reg. No. 35000-37-4) in tetrahydrofuran (10 ml). The suspension was stirred for 15 min at ambient temperature. 3-Fluoro-4-nitrobenzaldehyde (600 mg, 3.5 mmol; CAS Reg. No. 160538-51-2) was added, the mixture was stirred for 1.5 h at ambient temperature, poured onto water and extracted three times with ethyl acetate. The combined organic layers were washed with brine and dried over magnesium sulfate. The solid was filtered off and the filtrate was concentrated under reduced pressure to give a brown oil which was purified by column chromatography on silica gel using an MPLC system (CombiFlash Companion, Isco Inc.) eluting with a gradient of heptane: methyl tert-butyl ether (100:0 to 80:20 v/v) to afford the title compound as a brown oil (812 mg, 3.04 mmol; 86%).

61.2 3-(4-Amino-3-fluoro-phenyl)-propionic acid tert-butyl ester

A solution of (E)-3-(3-fluoro-4-nitro-phenyl)-acrylic acid tert-butyl ester (804 mg, 3.01 mmol) in ethyl acetate (10 ml) was hydrogenated on 10% palladium on charcoal for 30 min at 1.5 bar. The suspension was filtered, the filter cake washed with ethyl acetate and the filtrate evaporated and dried under high vacuum to give the product as light brown solid (713 mg, 3 mmol; 99%). This material was pure enough for the next step. MS: m/e=240.0 [M+H$^+$].

61.3 [rac]-3-(4-{2-[2-(4-Chloro-phenyl)-4,5,6,7-tetrahydro-2H-indazol-3-yl]-2-cyclohexyl-acetylamino}-3-fluoro-phenyl)-propionic acid tert-butyl ester In analogy to the procedure described in example 59, [2-(4-chloro-phenyl)-4,5,6,7-tetrahydro-2H-indazol-3-yl]-cyclohexyl-acetic acid (example 5.1) was reacted with 3-(4-amino-3-fluoro-phenyl)-propionic acid tert-butyl ester in the presence of DIPEA and HATU in DMF to give the title compound yellow solid.

61.4 [rac]-3-(4-{2-[2-(4-Chloro-phenyl)-4,5,6,7-tetrahydro-2H-indazol-3-yl]-2-cyclohexyl-acetylamino}-3-fluoro-phenyl)-propionic acid To a stirred solution of [rac]-3-(4-{2-[2-(4-chloro-phenyl)-4,5,6,7-tetrahydro-2H-indazol-3-yl]-2-cyclohexyl-acetylamino}-3-fluoro-phenyl)-propionic acid tert-butyl ester (150 mg, 0.25 mmol) in dry DCM (3 ml) was added trifluoroacetic acid (0.3 7 mL, 5.0 mmol) dropwise at 0° C. Then the reaction mixture was stirred at rt for 4 h, TLC shows complete consumption of the starting material. DCM and excess trifluoroacetic acid was then distilled off. Crude mixture was triturated with hexane-ether several times to give the title compound as yellow solid; yield: 75 mg, 52.8%. MS: m/e=538.0 [M+H$^+$].

Example 62

[rac]-3-Chloro-4-{2-[2-(4-chloro-phenyl)-4,5,6,7-tetrahydro-2H-indazol-3-yl]-2-cyclohexyl-acetylamino}-benzoic acid

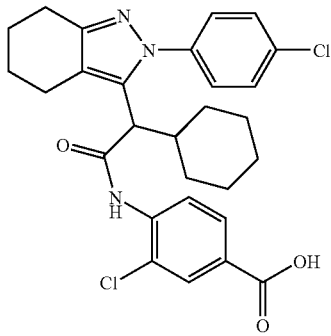

62.1 [rac]-3-Chloro-4-{2-[2-(4-chloro-phenyl)-4,5,6,7-tetrahydro-2H-indazol-3-yl]-2-cyclohexyl-acetylamino}-benzoic acid methyl ester In analogy to the procedure described in example 58.2, 2-(4-chloro-phenyl)-4,5,6,7-tetrahydro-2H-indazol-3-yl]-cyclohexyl-acetic acid pentafluorophenyl ester (example 21.4) was reacted with 4-amino-3-chloro-benzoic acid methyl ester (CAS Reg. No. 84228-44-4) in the presence of LiHMDS in THF to give the title compound as white solid.

62.2 [rac]-3-Chloro-4-{2-[2-(4-chloro-phenyl)-4,5,6,7-tetrahydro-2H-indazol-3-yl]-2-cyclohexyl-acetylamino}-benzoic acid In analogy to the procedure described in example 60.2, [rac]-3-chloro-4-{2-[2-(4-chloro-phenyl)-4,5,6,7-tetrahydro-2H-indazol-3-yl]-2-cyclohexyl-acetylamino}-benzoic acid methyl ester was treated with aqueous lithium hydroxide solution in THF to give the title compound as off-white solid. MS: m/e=526.0 [M+H$^+$].

Example 63

[rac]-4-{2-[2-(4-Chloro-phenyl)-4,5,6,7-tetrahydro-2H-indazol-3-yl]-2-cyclohexyl-ethylsulfanyl}-benzoic acid

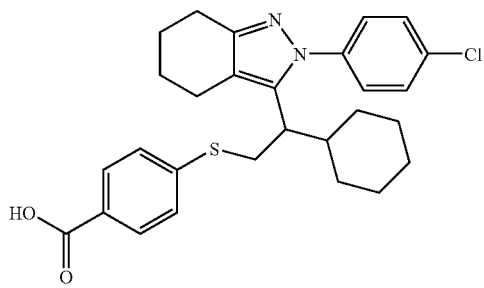

63.1 [rac]-Methanesulfonic acid 2-[2-(4-chloro-phenyl)-4,5,6,7-tetrahydro-2H-indazol-3-yl]-2-cyclohexyl-ethyl ester To a solution of [rac]-2-[2-(4-chloro-phenyl)-4,5,6,7-tetrahydro-2H-indazol-3-yl]-2-cyclohexyl-ethanol (example 37.1) (400 mg, 1.1 mmol) in dry DCM (15 ml) was added Et$_3$N (0.64 ml, 3.32 mmol) at room temperature. Mesyl chloride (0.16 ml, 2.22 mmol) was then added to this reaction mixture dropwise at 0° C.; and the reaction mixture was stirred at room temperature for 2 hours. TLC shows complete consumption of [rac]-2-[2-(4-chloro-phenyl)-4,5,6,7-tetrahydro-2H-indazol-3-yl]-2-cyclohexyl-ethanol. The reaction mixture was diluted with H$_2$O (10 ml) and the aqueous layer was extracted with DCM (3×10 ml). Combined organic layers were washed with ice water (10 ml), 10% NaHCO$_3$ (10 ml), brine (10 ml) and finally dried over Na$_2$SO$_4$. Organic layer was distilled under reduced pressure to get light yellow oil (500 mg), which was purified by column chromatography [SiO$_2$ (230-400 mesh), EtOAc:Hexane 10/90] to give the title compound (370 mg, 76%) as a light yellow liquid.

63.2 [rac]-4-{2-[2-(4-Chloro-phenyl)-4,5,6,7-tetrahydro-2H-indazol-3-yl]-2-cyclohexyl-ethylsulfanyl}-benzoic acid methyl ester To a solution of methyl 4-mercaptobenzoate (54.0 mg, 0.306 mmol; CAS Reg. No. 6302-65-4) in dry DMF (3 ml) was added K$_2$CO$_3$ (43.0 mg, 0.306 mmol) at 0° C. The reaction mixture was stirred for 15 minutes at 0° C. [rac]-Methanesulfonic acid 2-[2-(4-chloro-phenyl)-4,5,6,7-tetrahydro-2H-indazol-3-yl]-2-cyclohexyl-ethyl ester (135.0 mg, 0.306 mmol) dissolved in dry DMF (1 ml) was then added at 0° C. The reaction mixture was then heated at 100° C. in a sealed tube for 12 hours. LC-MS shows the formation of the desired compound with some starting material. 10 ml of 10% citric acid solution was then added to the reaction mixture and extracted with EtOAc (3×8 ml). Combined organic layers were washed with brine (10 ml) and finally dried over Na$_2$SO$_4$. Organic layer was distilled under reduced pressure to get light yellow oil (234 mg), which was purified by column chromatography [SiO$_2$ (230-400 mesh), EtOAc:Hexane 8/92] to give the title compound (57 mg, 36.2%) as a off white sticky solid.

63.3 [rac]-4-{2-[2-(4-Chloro-phenyl)-4,5,6,7-tetrahydro-2H-indazol-3-yl]-2-cyclohexyl-ethylsulfanyl}-benzoic acid To a stirred solution of [rac]-4-{2-[2-(4-chloro-phenyl)-4,5,6,7-tetrahydro-2H-indazol-3-yl]-2-cyclohexyl-ethylsulfanyl}-benzoic acid methyl ester (22 mg, 0.043 mmol) in MeOH (5 ml) was added NaOH (5.18 mg, 0.129 mmol) in water (2 ml) dropwise at 0° C. The reaction mixture was then stirred at rt for 14 hours. After the completion of the reaction (monitored through TLC), MeOH was concentrated in vacuo, diluted with H$_2$O (7 ml) and the aqueous layer was acidified (pH ~2-3) with 2 N HCl and then extracted with EtOAc (3×7 ml). Combined organic layers were washed with brine (8 ml) and finally dried over Na$_2$SO$_4$. Organic layer was distilled under reduced pressure to get off white solid (20 mg), which was purified by column chromatography [SiO$_2$ (230-400 mesh), DCM:MeOH 98.0/2.0] to give the title compound (18 mg, 84.1%) as a off white solid. MS: m/e=495.0 [M+H±].

Example 64

[rac]-6-{2-[2-(4-Chloro-phenyl)-4,5,6,7-tetrahydro-2H-indazol-3-yl]-2-cyclohexyl-ethoxy}-nicotinic acid

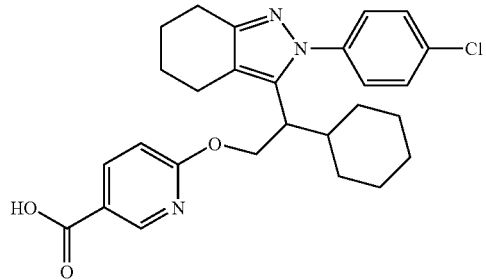

64.1 [rac]-6-{2-[2-(4-Chloro-phenyl)-4,5,6,7-tetrahydro-2H-indazol-3-yl]-2-cyclohexyl-ethoxy}-nicotinic acid methyl ester In analogy to the procedure described in example 63.2, [rac]-methanesulfonic acid 2-[2-(4-chloro-phenyl)-4,5,6,7-tetrahydro-2H-indazol-3-yl]-2-cyclohexyl-ethyl ester (example 63.1) was reacted with 6-hydroxy-nicotinic acid methyl ester (CAS Reg. No. 10128-91-3) in the presence of K$_2$CO$_3$ in DMF to give the title compound as white solid.

64.2 [rac]-6-{2-[2-(4-Chloro-phenyl)-4,5,6,7-tetrahydro-2H-indazol-3-yl]-2-cyclohexyl-ethoxy}-nicotinic acid In analogy to the procedure described in example 63.3, [rac]-6-{2-[2-(4-chloro-phenyl)-4,5,6,7-tetrahydro-2H-indazol-3-yl]-2-cyclohexyl-ethoxy}-nicotinic acid methyl ester was treated with NaOH in MeOH to give the title compound as off-white solid. MS: m/e=480.0 [M+H$^+$].

Example 65

[rac]-{2-[2-(4-Chloro-phenyl)-4,5,6,7-tetrahydro-2H-indazol-3-yl]-2-cyclohexyl-ethyl}-[4-(1H-tetrazol-5-yl)-phenyl]-amine

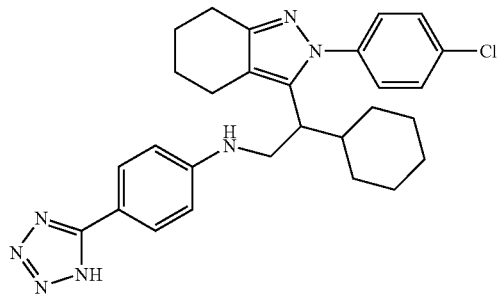

In analogy to the procedure described in example 29.1, [rac]-2-[2-(4-chloro-phenyl)-4,5,6,7-tetrahydro-2H-indazol-3-yl]-2-cyclohexyl-N-[2-fluoro-4-(1H-tetrazol-5-yl)-phenyl]-acetamide (example 58) was reduced using borane-dimethylsulfide complex in THF to give the title compound as brown solid. MS: m/e=502.0 [M+H$^{+]}$1.

Example 66

[rac]-4-{2-[2-(4-Chloro-phenyl)-4,5,6,7-tetrahydro-2H-indazol-3-yl]-2-cyclohexyl-ethanesulfonyl}-benzoic acid

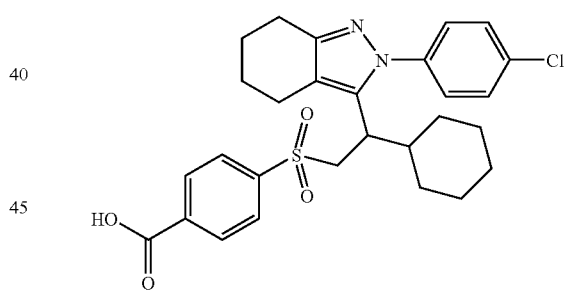

66.1 [rac]-4-{2-[2-(4-Chloro-phenyl)-4,5,6,7-tetrahydro-2H-indazol-3-yl]-2-cyclohexyl-ethanesulfonyl}-benzoic acid methyl ester To a stirred solution of [rac]-4-{2-[2-(4-chloro-phenyl)-4,5,6,7-tetrahydro-2H-indazol-3-yl]-2-cyclohexyl-ethylsulfanyl}-benzoic acid methyl ester (70 mg, 0.13 mmol; example 63.2) in DCM (5 ml) was added freshly recrystallized 3-chloroperbenzoic acid (45 mg, 0.26 mmol) at 0° C. The reaction mixture was then stirred at 25° C. for 12 h. After the completion of the reaction (monitored through TLC), the reaction mixture was diluted with DCM (15 ml). Combined DCM layers were washed with saturated aqueous solution of NaHCO$_3$ (2×10 ml), brine (1×25 ml), dried over anhydrous Na$_2$SO$_4$, filtered and concentrated under reduced pressure yielded crude solid (120 mg). The residue was purified by column chromatography over silica gel (230-400 mesh; EtOAc:hexane 2:3 to 1:1) to give the title compound (40 mg, 55.5%) as an off white solid.

66.2 [rac]-4-{2-[2-(4-Chloro-phenyl)-4,5,6,7-tetrahydro-2H-indazol-3-yl]-2-cyclohexyl-ethanesulfonyl}-benzoic acid To a stirred solution of [rac]-4-{2-[2-(4-chloro-phenyl)-4,5,6,7-tetrahydro-2H-indazol-3-yl]-2-cyclohexyl-ethanesulfonyl}-benzoic acid methyl ester (40 mg, 0.076 mmol) in MeOH (5 ml) was added NaOH (5.18 mg, 0.129 mmol) in water (2 ml) dropwise at 0° C. The reaction mixture was then stirred at 25° C. for 14 h. After the completion of the reaction (monitored through TLC), MeOH was concentrated in vacuo, diluted with $H_2O$ (5 ml) and the aqueous layer was acidified (pH ~2-3) with 2 N HCl, and then extracted with EtOAc (3×5 ml). Combined organic layers were washed with brine (10 ml) and finally dried over $Na_2SO_4$. Organic layer was distilled under reduced pressure to get crude title compound (32 mg). Purification was done by column chromatography over silica gel (230-400 mesh; 2% MeOH/DCM) to give the title compound (18 mg, 47.1%) as an off white solid. MS: m/e=527.2 $[M+H^+]$.

Example 67

[rac]-4-{(E)-3-[2-(4-Chloro-phenyl)-4,5,6,7-tetrahydro-2H-indazol-3-yl]-3-cyclohexyl-propenyl}-benzoic acid

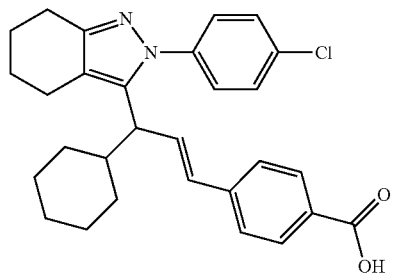

67.1 [2-(4-Chloro-phenyl)-4,5,6,7-tetrahydro-2H-indazol-3-yl]-cyclohexyl-acetaldehyde A turbid solution of 1.245 g (3.58 mmol) phosphonitrilic chloride trimer in 20 ml dichloromethane was cooled to −75° C. To this mixture 1.02 ml (14.32 mmol) DMSO were added, and stirring was continued for 1 h. Then a suspension of 1.28 g (3.58 mmol; 1 eq.; example 37.1) [rac]-2-[2-(4-chloro-phenyl)-4,5,6,7-tetrahydro-2H-indazol-3-yl]-2-cyclohexyl-ethanol in 50 ml dichloromethane was added dropwise over 10 min to the turbid reaction mixture, keeping the temperature below −60° C. The reaction mixture was then stirred 1 h at −75° C. Then the mixture was stirred in an ice-bath, and at 0° C. 2.50 ml (17.91 mmol) triethylamine were added. The solution was stirred 1.5 h at 0° C. and then at ambient temperature overnight. The reaction mixture was poured onto 120 ml water, extracted 3 times with dichloromethane. The organic layers were washed with water and brine, dried over $MgSO_4$, filtered and evaporated to give the crude product which was purified on a 20 g silica gel column using a gradient from heptane (A) and ethyl acetate (B) to give the title aldehyde.

67.2 [rac]-4-{(E)-3-[2-(4-Chloro-phenyl)-4,5,6,7-tetrahydro-2H-indazol-3-yl]-3-cyclohexyl-propenyl}-benzoic acid methyl ester To a solution of 379 mg (0.772 mmol) 4-carbomethoxy-benzyl triphenylphosphonium bromide ([1253-46-9]) in 6 ml THF was added 87 mg (0.772 mmol) potassium tert-butoxide at 0° C. The reaction mixture was stirred for 15 minutes at 0° C. [2-(4-Chloro-phenyl)-4,5,6,7-tetrahydro-2H-indazol-3-yl]-cyclohexyl-acetaldehyde (0.772 mmol; 1 eq.) was added at 0° C. The reaction mixture was stirred for 4 hours at room temperature. The reaction mixture was poured on 30 ml citric acid 10% in $H_2O$ and 30 ml EtOAc. The aqueous layer was extracted a second time with 30 ml EtOAc. The combined organic layers were washed with 30 ml brine, dried over $MgSO_4$, filtered and concentrated under vacuum. The residue was purified by column chromatography (20 g silica gel; gradient: n-heptane:EtOAc) to give the title compound.

67.3 [rac]-4-{(E)-3-[2-(4-Chloro-phenyl)-4,5,6,7-tetrahydro-2H-indazol-3-yl]-3-cyclohexyl-propenyl}-benzoic acid In analogy to the procedure described in example 63.3, [rac]-4-{(E)-3-[2-(4-chloro-phenyl)-4,5,6,7-tetrahydro-2H-indazol-3-yl]-3-cyclohexyl-propenyl}-benzoic acid methyl ester was treated with NaOH in MeOH to give the title compound.

Example 68

[rac]-4-[3-Cyclohexyl-3-(2-phenyl-4,5,6,7-tetrahydro-2H-indazol-3-yl)-propyl]-benzoic acid

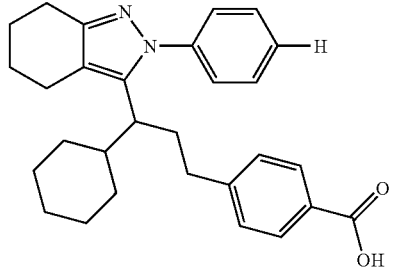

To a solution of [rac]-4-{(E)-3-[2-(4-chloro-phenyl)-4,5,6,7-tetrahydro-2H-indazol-3-yl]-3-cyclohexyl-propenyl}-benzoic acid (0.227 mmol; example 67.3) in 3 ml EtOAc was added 30 mg Pd (5%) on charcoal. 3 ml MeOH was added. The reaction mixture was vigorously stirred at room temperature under 1.5 bar $H_2$ pressure for 1 hours. The reaction mixture was filtrated over dicalite and concentrated under vacuum. The residue was purified by preparative HPLC to give the title compound.

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula I | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula I | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesiumstearate and the flavoring additives and filled into sachets.

The invention claimed is:

1. Compounds of the formula

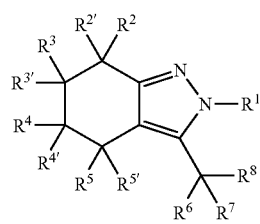

I wherein $R^1$ is a ring selected from the group consisting of phenyl, naphthyl and heteroaryl, said ring being unsubstituted or substituted with 1 to 3 substituents independently selected from the group consisting of lower alkyl, halogen, lower halogenalkyl, hydroxy, lower alkoxy, lower halogenalkoxy and cyano;

$R^2$, $R^3$, $R^4$ and $R^5$ independently from each other are selected from the group consisting of hydrogen, halogen or lower alkyl;

$R^{2'}$ and $R^{3'}$ together as well as $R^{4'}$ and $R^{5'}$ together are replaced by a double bond, or $R^{2'}$, $R^{3'}$, $R^{4'}$ and $R^{5'}$ are hydrogen;

$R^6$ is selected from the group consisting of hydrogen, methyl, ethyl, hydroxy, methoxy, fluoro, fluoromethyl, difluoromethyl and trifluoromethyl;

$R^7$ is selected from the group consisting of lower alkyl, cycloalkyl, lower cycloalkylalkyl, lower alkoxyalkyl,
unsubstituted phenyl or phenyl substituted with 1 to 3 substituents independently selected from the group consisting of lower alkyl, halogen, lower halogenalkyl, hydroxy, lower alkoxy, lower halogenalkoxy and cyano,
lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy and cyano,
unsubstituted heteroaryl or heteroaryl substituted with 1 to 3 substituents independently selected from the group consisting of lower alkyl, halogen, lower halogenalkyl, hydroxy, lower alkoxy, lower halogenalkoxy and cyano, and
heterocyclyl; and $R^8$ is selected from the group consisting of —C(O)—NH—$R^9$,
—$CR^{11}R^{12}$—$OR^{10}$, —O—$(CR^{11}R^{12})_n$—$R^{10}$;
—$CR^{11}R^{12}$—$SR^{10}$, —$CR^{11}R^{12}$—$SO_2$—$R^{10}$,
—$CR^{11}R^{12}$—$NR^{13}$—$R^{10}$; —CH=CH—$R^{10}$ and —$(CH_2)_p$—$R^{10}$,
wherein
n is 0 or 1, p is 2, $R^9$ is selected from the group consisting of
lower alkyl, cycloalkyl, lower cycloalkylalkyl,
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl,
unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl;

$R^{10}$ is selected from the group consisting of
lower alkyl, cycloalkyl, lower cycloalkylalkyl,
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl,
unsubstituted pyridyl and pyridyl substituted by carboxyl, lower alkoxycarbonyl or tetrazolyl,
unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl, and
lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl;

$R^{11}$ and $R^{12}$ independently are selected from the group consisting of hydrogen, lower alkyl and lower halogenalkyl,
or $R^{11}$ and $R^{12}$ together with the carbon atom to which they are attached form a cycloalkyl or alkoxycycloalkyl ring; and $R^{13}$ is selected from the group consisting of hydrogen, lower alkyl and lower halogenalkyl; or pharmaceutically acceptable salts thereof.

2. The compound of formula I according to claim 1, wherein $R^1$ is a phenyl ring, said ring being unsubstituted or substituted with 1 to 3 substituents independently selected from the group consisting of lower alkyl, halogen, lower halogenalkyl, hydroxy, lower alkoxy, lower halogenalkoxy and cyano.

3. The compound of formula I according to claim 2, wherein $R^1$ is phenyl or phenyl substituted with halogen.

4. The compound of formula I according to any one of claim 1, wherein $R^2$, $R^3$, $R^4$ and $R^5$ are hydrogen.

5. The compounds of formula I according to any one of claim 1, wherein $R^{2'}$ and $R^{3'}$ together as well as $R^{4'}$ and $R^{5'}$ together are replaced by a double bond.

6. The compounds of formula I according to any one of claim 1, wherein $R^{2'}$, $R^{3'}$, $R^{4'}$ and $R^{5'}$ are hydrogen.

7. The compound of formula I according to claim 1, wherein $R^6$ is selected from the group consisting of hydrogen, hydroxy and fluoro.

8. The compound of formula I according to any one of claim 7, wherein $R^6$ is hydrogen.

9. The compound of formula I according to claim 1, wherein $R^7$ is selected from the group consisting of cycloalkyl, unsubstituted phenyl and phenyl substituted with 1 to 3 substituents independently selected from the group consisting of lower alkyl, halogen, lower halogenalkyl, hydroxy, lower alkoxy, lower halogenalkoxy and cyano.

10. The compound of formula I according to claim 9, wherein $R^7$ is cycloalkyl.

11. The compound of formula I according to claim 1, wherein $R^8$ is
—C(O)—NH—$R^9$ and $R^9$ is selected from the group consisting of lower alkyl,
cycloalkyl, lower cycloalkylalkyl,
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy,
heterocyclyl,
unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy, wherein the cycloalkyl group is substituted by carboxyl, lower alkoxycarbonyl or tetrazolyl.

12. The compound of formula I according to claim 11, wherein $R^9$ is selected from the group consisting of cycloalkyl, cycloalkyl substituted by hydroxy, unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl or tetrazolyl.

13. The compound of formula I according to claim 12, wherein $R^9$ is selected from the group consisting of cycloalkyl, cycloalkyl substituted by hydroxy and phenyl substituted with 1 to 3 substituents independently selected from halogen and carboxyl.

14. The compound of formula I according to claim 13, wherein $R^9$ is cycloalkyl.

15. The compounds of formula I according to claim 1, wherein $R^8$ is —$CR^{11}R^{12}$—$OR^{10}$ or —O—$CR^{11}R^{12}$—$R^{10}$ and wherein
$R^{10}$ is selected from the group consisting of
lower alkyl, cycloalkyl, lower cycloalkylalkyl,
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl,
unsubstituted pyridyl and pyridyl substituted by carboxyl, lower alkoxycarbonyl or tetrazolyl,
unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl, and
lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl; and
$R^{11}$ and $R^{12}$ independently are selected from the group consisting of hydrogen, lower alkyl and lower halogenalkyl,
or $R^{11}$ and $R^{12}$ together with the carbon atom to which they are attached form a cycloalkyl or alkoxycycloalkyl ring.

16. The compound of formula I according to claim 1, wherein $R^8$ is selected from the group consisting of —$CR^{11}R^{12}$—$SR^{10}$, —$CR^{11}R^{12}$—$SO_2$—$R^{10}$ and —$CR^{11}R^{12}$—$NR^{13}$—$R^{10}$ and wherein
$R^{10}$ is selected from the group consisting of
lower alkyl, cycloalkyl, lower cycloalkylalkyl,
cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl,
unsubstituted pyridyl and pyridyl substituted by carboxyl, lower alkoxycarbonyl or tetrazolyl,
unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl, and
lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl, lower alkoxycarbonyl or tetrazolyl;
$R^{11}$ and $R^{12}$ independently are selected from the group consisting of hydrogen, lower alkyl and lower halogenalkyl,
or $R^{11}$ and $R^{12}$ together with the carbon atom to which they are attached form a cycloalkyl or alkoxycycloalkyl ring, and
$R^{13}$ is selected from the group consisting of hydrogen, lower alkyl and lower halogenalkyl.

17. The compound according to claim 1 having the formula

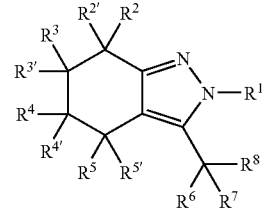

1-A wherein
$R^1$ is a ring selected from phenyl, naphthyl and heteroaryl, said ring being unsubstituted or substituted with 1 to 3 substituents independently selected from the group consisting of lower alkyl, halogen, lower halogenalkyl, hydroxy, lower alkoxy, lower halogenalkoxy and cyano;
$R^2$, $R^3$, $R^4$ and $R^5$ independently from each other are selected from the group consisting of hydrogen, halogen or lower alkyl;
$R^2$ and $R^{3'}$ together as well as $R^{4'}$ and $R^{5'}$ together are replaced by a double bond,
or $R^{2'}$, $R^{3'}$, $R^{4'}$ and $R^{5'}$ are hydrogen;
$R^6$ is selected from the group consisting of hydrogen, methyl, ethyl, hydroxy, methoxy, fluoro, fluoromethyl, difluoromethyl and trifluoromethyl;
$R^7$ is selected from the group consisting of lower alkyl, cycloalkyl, lower cycloalkylalkyl, lower alkoxyalkyl, unsubstituted phenyl or phenyl substituted with 1 to 3 substituents independently selected from the group consisting of lower alkyl, halogen, lower halogenalkyl, hydroxy, lower alkoxy, lower halogenalkoxy and cyano, lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy and cyano, unsubstituted heteroaryl or heteroaryl substituted with 1 to 3 substituents independently selected from the group consisting of lower alkyl, halogen, lower halogenalkyl, hydroxy, lower alkoxy, lower halogenalkoxy and cyano, and heterocyclyl; and $R^8$ is selected from the group consisting of —C(O)—NH—$R^9$, —$CR^{11}R^{12}$—$OR^{10}$ and —O—$CR^{11}R^{12}$—$R^{10}$; wherein $R^9$ is selected from the group consisting of lower alkyl, cycloalkyl, lower cycloalkylalkyl, cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl, unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl or tetrazolyl;

$R^{10}$ is selected from the group consisting of lower alkyl, cycloalkyl, lower cycloalkylalkyl, cycloalkyl substituted with 1 to 3 substituents independently selected from the group consisting of hydroxy, carboxyl, tetrazolyl, lower carboxylalkyl, lower alkoxycarbonyl, lower alkoxycarbonylalkyl, lower carboxylalkoxy and lower alkoxycarbonylalkoxy, heterocyclyl, unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl or tetrazolyl, and lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl or tetrazolyl; and $R^{11}$ and $R^{12}$ independently are selected from the group consisting of hydrogen, lower alkyl and lower halogenalkyl, or $R^{11}$ and $R^{12}$ together with the carbon atom to which they are attached form a cycloalkyl or alkoxycycloalkyl ring;

or pharmaceutically acceptable salts thereof.

18. A compound of formula I-A according to claim 17, selected from the group consisting of 2,N-dicyclohexyl-2-(2-phenyl-2H-indazol-3-yl)-acetamide, N-cyclohexyl-2-(3-methoxy-phenyl)-2-(2-phenyl-2H-indazol-3-yl)-acetamide, N-cyclohexyl-2-phenyl-2-(2-phenyl-2H-indazol-3-yl)-acetamide, 2-[2-(4-chloro-phenyl)-2H-indazol-3-yl]-2,N-dicyclohexyl-acetamide, 4-{2-[2-(4-chloro-phenyl)-4,5,6,7-tetrahydro-2H-indazol-3-yl]-2-cyclohexyl-2-hydroxy-acetylamino}-3-fluoro-benzoic acid, 2-[2-(4-chloro-phenyl)-4,5,6,7-tetrahydro-2H-indazol-3-yl]-2,N-dicyclohexyl-acetamide, 4-{2-[2-(4-chloro-phenyl)-4,5,6,7-tetrahydro-2H-indazol-3-yl]-2-cyclohexyl-acetylamino}-benzoic acid, 2-[2-(4-chloro-phenyl)-4,5,6,7-tetrahydro-2H-indazol-3-yl]-2-cyclohexyl-N-cyclopentyl-acetamide, 2-[2-(4-chloro-phenyl)-4,5,6,7-tetrahydro-2H-indazol-3-yl]-2-cyclohexyl-N-cyclopentyl-2-hydroxy-acetamide, 2-[2-(4-chloro-phenyl)-2H-indazol-3-yl]-2-cyclohexyl-(trans)-N-(4-hydroxy-cyclohexyl)-acetamide, 4-{2-[2-(4-chloro-phenyl)-4,5,6,7-tetrahydro-2H-indazol-3-yl]-2-cyclohexyl-acetylamino}-3-fluoro-benzoic acid, 4-{2-[2-(4-chloro-phenyl)-2H-indazol-3-yl]-2-cyclohexyl-acetylamino}-benzoic acid, 4-{2-[2-(4-chloro-phenyl)-2H-indazol-3-yl]-2-cyclohexyl-acetylamino}-3-fluoro-benzoic acid, or pharmaceutically acceptable salts thereof.

19. A compound of formula I-A according to claim 17, selected from the group consisting of 2,N-dicyclohexyl-2-(2-phenyl-2H-indazol-3-yl)-acetamide, N-cyclohexyl-2-phenyl-2-(2-phenyl-2H-indazol-3-yl)-acetamide, 4-{2-[2-(4-chloro-phenyl)-4,5,6,7-tetrahydro-2H-indazol-3-yl]-2-cyclohexyl-2-hydroxy-acetylamino}-3-fluoro-benzoic acid, 2-[2-(4-chloro-phenyl)-4,5,6,7-tetrahydro-2H-indazol-3-yl]-2,N-dicyclohexyl-acetamide, 2-[2-(4-chloro-phenyl)-2H-indazol-3-yl]-2-cyclohexyl-(trans)-N-(4-hydroxy-cyclohexyl)-acetamide, 4-{2-[2-(4-chloro-phenyl)-4,5,6,7-tetrahydro-2H-indazol-3-yl]-2-cyclohexyl-acetylamino}-3-fluoro-benzoic acid, 4-{2-[2-(4-chloro-phenyl)-2H-indazol-3-yl]-2-cyclohexyl-acetylamino}-3-fluoro-benzoic acid, and pharmaceutically acceptable salts thereof.

20. A compound of formula I-A according to claim 17, selected from the group consisting of 2-[2-(4-chloro-phenyl)-4,5,6,7-tetrahydro-2H-indazol-3-yl]-2,N-dicyclohexyl-acetamide, 4-{2-[2-(4-chloro-phenyl)-4,5,6,7-tetrahydro-2H-indazol-3-yl]-2-cyclohexyl-acetylamino}-3-fluoro-benzoic acid, and pharmaceutically acceptable salts thereof.

21. A process for the preparation of compounds of formula I according to claim 1 wherein $R^8$ is —C(O)—NH—$R^9$, which process comprises a) reacting a carboxylic acid of the formula II

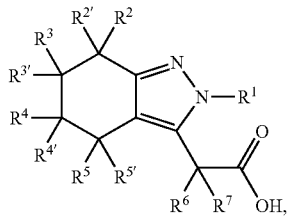

wherein $R^1$ to $R^7$ are as defined in claim 1, with an amine of the formula III

wherein $R^9$ is a defined in claim 1, in the presence of a coupling reagent under basic conditions to obtain a compound of the formula Ic

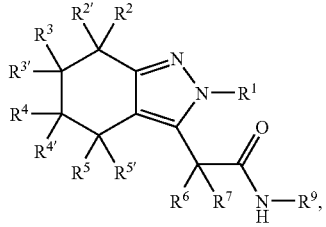

wherein $R^1$ to $R^7$ and $R^9$ are as defined above, and, if desired, b) converting the compound obtained into a pharmaceutically acceptable salt.

22. A pharmaceutical composition comprising a compound of formula I according to claim 1 and a pharmaceutically acceptable carrier and/or adjuvant.

23. A method for the therapeutic treatment of a disease which is affected by FXR modulators, wherein said disease is diabetes, which method comprises administering a compound of formula I according to claim 1 to a human being or animal.

24. A compound of formula I according to claim 1, selected from the group consisting of 2-[2-(4-chloro-phenyl)-4,5,6,7-tetrahydro-2H-indazol-3-yl]-cyclohexyl-N-2,4-difluoro-phenyl)-acetamide, 1-(4-{2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid methyl ester, 1-(4-{2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid, 4-{[2-(4-chloro-phenyl)-2H-indazol-3-yl]-cyclohexyl-methoxymethyl}-benzoic acid methyl ester, 4-{[2-(4-chloro-phenyl)-2H-indazol-3-yl]-cyclohexyl-methoxymethyl}-benzoic acid, 4-{2-[2-(4-chloro-phenyl)-4,5,6,7-tetrahydro-2H-indazol-3-yl]-2-cyclohexyl-acetylamino}-3-trifluoromethyl-benzoic acid methyl ester, 4-{2-[2-(4-chloro-phenyl)-4,5,6,7-tetrahydro-2H-indazol-3-yl]-2-cyclohexyl-acetylamino}-3-trifluoromethyl-benzoic acid, 1-(4-{(S-2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid tert-butyl ester, 1-(4-{(R)-2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid, 1-(4-{(S)-2-[2-(4-chloro-phenyl)-4,5,6,7-tetrahydro-2H-indazol-3-yl-2-cyclohexyl-acetylamino}-3-fluoro-phenoxy)-cyclopropanecarboxylic acid, 2-[2-(4-chloro-phenyl)-5,6-difluoro-2H-indazol-3-yl]-2, N-dicyclohexyl-acetamide, 2-(4-{2-[2-(4-chloro-phenyl)-5,6-difluoro-2H-indazol-3-yl]-2-cyclohexyl-acetylamino}-3-fluoro-phenoxy)-2-methyl-propionic acid ethyl ester, 2-(4-{2-[2-(4-chloro-phenyl)-5,6-difluoro-2H-indazol-3-yl]-2-cyclohexyl-acetylamino}-3-fluoro-phenoxy)-2-methyl-propionic acid, 4-{[2-(4-chloro-phenyl)-5,6-difluoro-2H-indazol-3-yl]-cyclohexyl-methoxymethyl}-benzoic acid 4-{[2-(4-chloro-phenyl)-4,5,6,7-tetrahydro-2H-indazol-3-yl]-cyclohexyl-methoxymethyl}-benzoic acid, 4-{2-[2-(4-chloro-phenyl)-2H-indazol-3-yl]-2-cyclohexyl-ethoxy}-3,5-dimethyl-benzoic acid, 4-{2-[2-(4-chloro-phenyl)-2H-indazol-3-yl]-2-cyclohexyl-ethoxy}-3-fluoro-benzonitrile, 2-(4-chloro-phenyl)-3-{1-cyclohexyl-2-[2-fluoro-4-(2H-tetrazol-5-yl)-phenoxy]-ethyl}-2H-indazole, 4-{2-[2-(4-chloro-phenyl)-5,6-difluoro-2H-indazol-3-yl]-2-cyclohexyl-acetylamino}-3-fluoro-benzoic acid, 4-{[2-(4-chloro-phenyl)-5,6-difluoro-2H-indazol-3-yl]-cyclohexyl-methoxy}-3,5-dimethyl-benzoic acid methyl ester, 4-{[2-(4-chloro-phenyl)-5,6-difluoro-2H-indazol-3-yl]-cyclohexyl-methoxy}-3,5-dimethyl-benzoic acid, 4-{[2-(4-chloro-phenyl)-5,6-difluoro-2H-indazol-3-yl]-cyclohexyl-methoxy}-3-fluoro-benzonitrile, 2-(4-chloro-phenyl)-3-{1-cyclohexyl-2-[2-fluoro-4-(2H-tetrazol-5-yl)-phenoxy]-ethyl}-5,6-difluoro-2H-indazole, 4-{2-[2-(4-chloro-phenyl)-4,5,6,7-tetrahydro-2H-indazol-3-yl]-2-cyclohexyl-ethoxy}-3-fluoro-benzonitrile, 2-(4-chloro-phenyl)-3-{1-cyclohexyl-2-[2-fluoro-4-(1H-tetrazol-5-yl)-phenoxy]-ethyl}-4,5,6,7-tetrahydro-2H-indazole, 4-{2-[2-(4-chloro-phenyl)-4,5,6,7-tetrahydro-2H-indazol-3-yl]-2-cyclohexyl-ethoxy}-3,5-dimethyl-benzoic acid methyl ester, 4-{2-[2-(4-chloro-phenyl)-4,5,6,7-tetrahydro-2H-indazol-3-yl]-2-cyclohexyl-ethoxy}-3,5-dimethyl-benzoic acid, 4-{[2-(4-chloro-phenyl)-5,6-difluoro-2H-indazol-3-yl]-cyclohexyl-methoxymethyl}-3-fluoro-benzonitrile, 2-(4-chloro-phenyl)-3-{cyclohexyl-[2-fluoro-4-(2H-tetrazol-5-yl)-benzyloxy]-methyl}-5,6-difluoro-2H-indazole, 4-{2-[2-(4-chloro-phenyl)-5,6-difluoro-2H-indazol-3-yl]-2-cyclohexyl-ethoxy}-3,5-dimethyl-benzoic acid, 4-{[2-(4-chloro-phenyl)-4,5,6,7-tetrahydro-2H-indazol-3-yl]-cyclohexyl-methoxymethyl}-benzonitrile, 4-{[2-(4-chloro-phenyl)-2H-indazol-3-yl]-cyclohexyl-methoxymethyl}-3-fluoro-benzonitrile, 4-{[2-(4-chloro-phenyl)-2H-indazol-3-yl]-cyclohexyl-methoxymethyl}-benzonitrile, 2-(4-chloro-phenyl)-3-{cyclohexyl-[4-(2H-tetrazol-5-yl)-benzyloxy]-methyl}-2H-indazole,
4-{[2-(4-chloro-phenyl)-5,6-difluoro-2H-indazol-3-yl]-cyclohexyl-methoxymethyl}-benzonitrile,
2-(4-chloro-phenyl)-3-{cyclohexyl-[4-(2H-tetrazol-5-yl)-benzyloxy]-methyl}-5,6-difluoro-2H-indazole,
2-(4-chloro-phenyl)-3-{cyclohexyl-[2-fluoro-4-(1H-tetrazol-5-yl)-phenoxy]-methyl}-5,6-difluoro-2H-indazole,
4-{2-[2-(4-chloro-phenyl)-2H-indazol-3-yl]-2-cyclohexyl-ethoxy}-3,5-dimethyl-benzonitrile,
2-(4-chloro-phenyl)-3-{1-cyclohexyl-2-[2,6-dimethyl-4-(2H-tetrazol-5-yl)-phenoxy]-ethyl}-2H-indazole,
6-{2-[2-(4-chloro-phenyl)-2H-indazol-3-yl]-2-cyclohexyl-ethoxy}-nicotinic acid,
1-(4-{2-[2-(4-chloro-phenyl)-2H-indazol-3-yl]-2-cyclohexyl-ethoxy}-phenoxy)-cyclopropanecarboxylic acid methyl ester,
1-(4-{2-[2-(4-chloro-phenyl)-4,5,6,7-tetrahydro-2H-indazol-3-yl]-2-cyclohexyl-ethoxy}-phenoxy)-cyclopropanecarboxylic acid,
1-(4-{[2-(4-chloro-phenyl)-5,6-difluoro-2H-indazol-3-yl]-cyclohexyl-methoxy}-phenoxy)-cyclopropanecarboxylic acid,
2-[2-(4-chloro-phenyl-4,5,6,7-tetrahydro-2H-indazol-3-yl]-2cyclohexyl-N-[4-(1H-tetrazol-5-yl)-phenyl]-acetamide,
2-[2-(4-chloro-phenyl)-4,5,6,7-tetrahydro-2H-indazol-3-yl]-2-cyclohexyl-N-[2-fluoro-4-(1H-tetrazol-5-yl)-phenyl]-acetamide,
2-[2-(4-chloro-phenyl)-4,5,6,7-tetrahydro-2H-indazol-3-yl]-2-cyclohexyl-(trans)-N-(4-hydroxy-cyclohexyl)-acetamide,
(4-{2-[2-(4-chloro-phenyl-4,5,6,7-tetrahydro-2H-indazol-3-yl]-2cyclohexyl-(trans)-acetylamino}-cyclohexyl)-acetic acid,
3-(4-{2-[2-(4-chloro-phenyl)-4,5,6,7-tetrahydro-2H-indazol-3-yl]-2-cyclohexyl-acetylamino}-3-fluoro-phenyl)-propionic acid,
3-chloro-4-{2-[2-(4-chloro-phenyl)-4,5,6,7-tetrahydro-2H-indazol-3-yl]-2H-cyclohexyl-acetylamino}-3-acetylamino)-benzoic acid,
4-{2-[2-(4-chloro-phenyl)-4,5,6,7-tetrahydro-2H-indazol-3-yl]-2-cyclohexyl-ethylsulfanyl}-benzoic acid,
6-{2-[2-(4-chloro-phenyl)-4,5,6,7-tetrahydro-2H-indazol-3-yl]-2-cyclohexyl-ethoxy}-nicotinic acid
{2-[2-(4-chloro-phenyl)-4,5,6,7-tetrahydro-2H-indazol-3-yl]-2-cyclohexyl-ethyl}-[4-(1H-tetrazol-5-yl)-phenyl]-amine,
4-{2-[2-(4-chloro-phenyl)-4,5,6,7-tetrahydro-2H-indazol-3-yl]-2-cyclohexyl-ethanesulfonyl}-benzoic acid,
4-{(E)-3-[2-(4-chloro-phenyl)-4,5,6,7-tetrahydro-2H-indazol-3-yl]-3-cyclohexyl-propenyl}-benzoic acid,
4-[3-cyclohexyl-3-(2-phenyl-4,5,6,7-tetrahydro-2H-indazol-3-yl)-propyl]-benzoic acid,
or pharmaceutically acceptable salts thereof.

25. A compound of formula I according to claim 1, selected from the group consisting of
1-(4-{2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid,
4-{[2-(4-chloro-phenyl)-2H-indazol-3-yl]-cyclohexyl-methoxymethyl}-benzoic acid,
4-{2-[2-(4-chloro-phenyl)-4,5,6,7-tetrahydro-2H-indazol-3-yl]-2-cyclohexyl-acetylamino}-3-trifluoromethyl-benzoic acid,
1-(4-{(S-2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid,
2-[2-(4-chloro-phenyl)-5,6-difluoro-2H-indazol-3-yl]-2,N-dicyclohexyl-acetamide,
2-(4-{2-[2-(4-chloro-phenyl)-5,6-difluoro-2H-indazol-3-yl]-2-cyclohexyl-acetylamino}-3-fluoro-phenoxy)-2-methyl-propionic acid,
4-{[2-(4-chloro-phenyl)-5,6-difluoro-2H-indazol-3-yl]-cyclohexyl-methoxymethyl}-benzoic acid,
4-{2-[2-(4-chloro-phenyl)-2H-indazol-3-yl]-2-cyclohexyl-ethoxy}-3,5-dimethyl-benzoic acid,
2-(4-chloro-phenyl)-3-{1-cyclohexyl-2-[2-fluoro-4-(2H-tetrazol-5-yl)-phenoxy]-ethyl}-2H-indazole,
4-{[2-(4-chloro-phenyl)-5,6-difluoro-2H-indazol-3-yl]-cyclohexyl-methoxy}-3-fluoro-benzonitrile,
2-(4-chloro-phenyl)-3-{1-cyclohexyl-2-[2-fluoro-4-(2H-tetrazol-5-yl)-phenoxy]-ethyl}-5,6-difluoro-2H-indazole,
2-(4-chloro-phenyl)-3-{1-cyclohexyl-2-[2-fluoro-4-(1H-tetrazol-5-yl)-phenoxy]-ethyl}-4,5,6,7-tetrahydro-2H-indazole,
4-{2-[2-(4-chloro-phenyl)-4,5,6,7-tetrahydro-2H-indazol-3-yl]-2-cyclohexyl-ethoxy}-3,5-dimethyl-benzoic acid,
2-(4-chloro-phenyl)-3-{cyclohexyl-[2-fluoro-4-(2H-tetrazol-5-yl)-benzyloxy]-methyl}-5,6-difluoro-2H-indazole,
4-{2-[2-(4-chloro-phenyl)-5,6-difluoro-2H-indazol-3-yl]-2-cyclohexyl-ethoxy}-3,5-dimethyl-benzoic acid,
2-(4-chloro-phenyl)-3-{cyclohexyl-[4-(2H-tetrazol-5-yl)-benzyloxy]-methyl}-2H-indazole,
2-(4-chloro-phenyl)-3-cyclohexyl-[4-(2H-tetrazol-5-yl)-benzyloxy]-methyl)-5,6-difluoro-2H-indazole,
2-(4-chloro-phenyl)-3-{cyclohexyl-[2-fluoro-4-(1H-tetrazol-5-yl)-phenyl]-methyl}-5,6-difluoro-2H-indazole,
2-(4-chloro-phenyl)-3-{1-cyclohexyl-2-[2,6-dimethyl-4-(2H-tetrazol-5-yl)-phenoxy]-ethyl}-2H-indazole,
6-{2-[2-(4-chloro-phenyl)-2H-indazol-3-yl]-2-cyclohexyl-ethoxy}-nicotinic acid,
1-(4-{2-[2-(4-chloro-phenyl)-4,5,6,7-tetrahydro-2H-indazol-3-yl]-2-cyclohexyl-ethoxy}-phenoxy)-cyclopropanecarboxylic acid,
1-(4-{[2-(4-chloro-phenyl)-5,6-difluoro-2H-indazol-3-yl]-cyclohexyl-methoxy}-phenoxy)-cyclopropanecarboxylic acid,
2-[2-(4-chloro-phenyl)-4,5,6,7-tetrahydro-2H-indazol-3-yl]-2-cyclohexyl-N-[2-fluoro-4-(1H-tetrazol-5-yl)-phenyl]-acetamide,
2-[2-(4-chloro-phenyl)-4,5,6,7-tetrahydro-2H-indazol-3-yl]-2-cyclohexyl-(trans)-N-(4-hydroxy-cyclohexyl)-acetamide,
(4-{2-[2-(4-chloro-phenyl-4,5,6,7-tetrahydro-2H-indazol-3-yl]-2-cyclohexyl-(trans)-acetylamino}-cyclohexyl)-acetic acid,
3-(4-{2-[2-(4-chloro-phenyl)-4,5,6,7-tetrahydro-2H-indazol-3-yl]-2-cyclohexyl-acetylamino}-3-fluoro-phenyl)-propionic acid,
3-chloro-4-{2-[2-(4-chloro-phenyl)-4,5,6,7-tetrahydro-2H-indazol-3-yl]-2-cyclohexyl-acetylamino}-benzoic acid,
4-{2-[2-(4-chloro-phenyl)-4,5,6,7-tetrahydro-2H-indazol-3-yl]-2-cyclohexyl-ethylsulfanyl}-benzoic acid,
{2-[2-(4-chloro-phenyl)-4,5,6,7-tetrahydro-2H-indazol-3-yl]-2-cyclohexyl-ethyl}-[4-(1H-tetrazol-5-yl)-phenyl]-amine, 4-{2-[2-(4-chloro-phenyl)-4,5,6,7-tetrahydro-2H-indazol-3-yl]-2-cyclohexyl-ethanesulfonyl}-benzoic acid, and pharmaceutically acceptable salts thereof.

26. A compound of formula I according to claim 1, selected from the group consisting of 1-(4-{2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid, 1-(4-{(S-2-[2-(4-chloro-phenyl)-4,5,6,7-tetrahydro-2H-indazol-3-yl]-2-cyclohexyl-acetylamino}-3-fluoro-phenoxy)-cyclopropanecarboxylic acid, 4-{2-[2-(4-chloro-phenyl)-2H-indazol-3-yl]-2-cyclohexyl-ethoxy}-3,5-dimethyl-benzoic acid, 2-(4-chloro-phenyl)-3-{1-cyclohexyl-2-[2-fluoro-4-(2H-tetrazol-5-yl)-phenoxy]-ethyl}-5,6-difluoro-2H-indazole, 2-(4-chloro-phenyl)-3-{1-cyclohexyl-2-[2-fluoro-4-(1H-tetrazol-5-yl)-phenoxy]-ethyl}-4,5,6,7-tetrahydro-2H-indazole, 2-(4-chloro-phenyl)-3-{cyclohexyl-[2-fluoro-4-(2H-tetrazol-5-yl)-benzyloxy]-methyl}-5,6-difluoro-2H-indazole, 4-{2-[2-(4-chloro-phenyl)-5,6-difluoro-2H-indazol-3-yl]-2-cyclohexyl-ethoxy}-3,5-dimethyl-benzoic acid, 2-(4-chloro-phenyl)-3-{cyclohexyl-[4-(2H-tetrazol-5-yl)-benzyloxy]-methyl}-2H-indazole, 2-(4-chloro-phenyl)-3-{1-cyclohexyl-2-[2,6-dimethyl-4-(2H-tetrazol-5-yl)-phenoxy]-ethyl}-2H-indazole, and pharmaceutically acceptable salts thereof.

27. A pharmaceutical composition comprising a compound of formula I-A according to claim 17 and a pharmaceutically acceptable carrier and/or adjuvant.

28. A method for the therapeutic treatment of a disease which is affected by FXR modulators wherein said disease is diabetes, which method comprises administering a compound of formula I-A according to claim 17 to a human being or animal.

29. The method according to claim 23, wherein diabetes is non-insulin dependent diabetes mellitus.

30. The method according to claim 28, wherein diabetes is non-insulin dependent diabetes mellitus.

* * * * *